(12) United States Patent
Tyson et al.

(10) Patent No.: US 10,344,081 B2
(45) Date of Patent: Jul. 9, 2019

(54) TAU-BINDING ANTIBODIES

(71) Applicant: UCB BIOPHARMA SPRL, Brussels (BE)

(72) Inventors: Kerry Louise Tyson, Slough (GB); Terence Seward Baker, Slough (GB); Georges Mairet-Coello, Brussels (BE); Patrick Downey, Brussels (BE); Jean-Philippe Courade, Brussels (BE); David Edward Ormonde Knight, Slough (GB)

(73) Assignee: UCB BIOPHARMA SPRL, Brussels (BE)

( * ) Notice: Subject to any disclaimer, the term of this patent is extended or adjusted under 35 U.S.C. 154(b) by 0 days.

(21) Appl. No.: 15/742,070

(22) PCT Filed: Jul. 5, 2016

(86) PCT No.: PCT/EP2016/065809
§ 371 (c)(1),
(2) Date: Jan. 5, 2018

(87) PCT Pub. No.: WO2017/005732
PCT Pub. Date: Jan. 12, 2017

(65) Prior Publication Data
US 2018/0194832 A1 Jul. 12, 2018

(30) Foreign Application Priority Data

Jul. 6, 2015 (EP) ..................... 15175519

(51) Int. Cl.
| | | |
|---|---|---|
| C07K 16/18 | (2006.01) | |
| G01N 33/68 | (2006.01) | |
| A61K 39/00 | (2006.01) | |
| C07K 14/47 | (2006.01) | |
| A61P 25/28 | (2006.01) | |

(52) U.S. Cl.
CPC .............. *C07K 16/18* (2013.01); *A61P 25/28* (2018.01); *C07K 14/4711* (2013.01); *G01N 33/6896* (2013.01); *A61K 2039/505* (2013.01); *C07K 2317/24* (2013.01); *C07K 2317/34* (2013.01); *C07K 2317/55* (2013.01); *C07K 2317/56* (2013.01); *C07K 2317/565* (2013.01); *C07K 2317/92* (2013.01); *G01N 2333/4703* (2013.01); *G01N 2800/28* (2013.01); *G01N 2800/2821* (2013.01)

(58) Field of Classification Search
None
See application file for complete search history.

(56) References Cited

U.S. PATENT DOCUMENTS

| | | |
|---|---|---|
| 4,816,397 A | 3/1989 | Boss et al. |
| 4,816,567 A | 3/1989 | Cabilly et al. |
| 5,225,539 A | 7/1993 | Winter |
| 2017/0355756 A1* | 12/2017 | Julien ............... C07K 16/18 |
| 2018/0201666 A1 | 7/2018 | Knight et al. |

FOREIGN PATENT DOCUMENTS

| | | |
|---|---|---|
| EP | 0125023 | 6/1991 |
| EP | 0519596 | 12/1992 |
| EP | 0120694 | 7/1993 |
| EP | 0194276 | 8/1993 |
| EP | 0239400 | 8/1994 |
| WO | WO 86/01533 | 3/1986 |
| WO | WO 91/09967 | 7/1991 |
| WO | WO 92/22583 | 12/1992 |
| WO | WO 2005/003169 | 1/2005 |
| WO | WO 2005/003170 | 1/2005 |
| WO | WO 2005/003171 | 1/2005 |
| WO | WO 2005/113605 | 12/2005 |
| WO | WO 2007/024715 | 3/2007 |
| WO | WO 2008/012543 | 1/2008 |
| WO | WO2008068048 | * 6/2008 |
| WO | WO 2009/040562 | 4/2009 |
| WO | WO 2010/035012 | 4/2010 |
| WO | WO 2010/142423 | 12/2010 |
| WO | WO 2011/030107 | 3/2011 |
| WO | WO 2013/068571 | 5/2013 |
| WO | WO 2013/096380 | 6/2013 |
| WO | WO 2014/008404 | 1/2014 |
| WO | WO 2014/028777 | 2/2014 |
| WO | WO 2017/005734 | 1/2017 |

OTHER PUBLICATIONS

Kussie "A Single Engineered Amino Acid Substitution Changes Antibody Fine Specificity" J immunol 152(1):146-52 (Year: 1994).*
Chen "Enhancement and destruction of antibody function by somatic mutation: unequal occurrence is controlled by V gene combinatorial associations" EMBO 14(12):2784-2794 (Year: 1995).*
Braak, H. et al. "Staging of Alzheimer's Disease-Related Neurofibrillary Changes" *Neurobiology of Aging*, May 1, 1995, pp. 271-278, vol. 16, No. 3.
Buée, L. et al. "Tau protein isoforms, phosphorylation and role in neurodegenerative disorders" *Brain Research Reviews*, Aug. 1, 2000, pp. 95-130, vol. 33, No. 1.
Clavaguera, F. et al, ""Prion-Like" Templated Misfolding in Tauopathies" *Brain Pathology*, Apr. 16, 2013, pp. 342-349, vol. 23, No. 3.
Maccioni, R. B. et al. "Anomalously phosphorylated tau and Aβ fragments in the CSF correlates with cognitive impairment in MCI subjects" *Neurobiology of Aging*, Feb. 1, 2006, pp. 237-244, vol. 27, No. 2.
Mercken, M. et al. "Monoclonal antibodies with selective specificity for Alzheimer Tau are directed against phosphatase-sensitive epitopes" *Acta Neuropathologica*, Jan. 1, 1992, pp. 265-272, vol. 84, No. 3.
Yanamandra, K. et al. "Anti-tau antibody reduces insoluble tau and decreases brain atrophy" *Annals of Clinical and Translational Neurology*, Jan. 23, 2015, pp. 278-288, vol. 2, No. 3.

(Continued)

*Primary Examiner* — Adam Weidner
(74) *Attorney, Agent, or Firm* — Saliwanchik, Lloyd & Eisenschenk

(57) ABSTRACT

The present invention relates to Tau-binding antibodies and binding fragments thereof.

38 Claims, 8 Drawing Sheets

Figure 1:
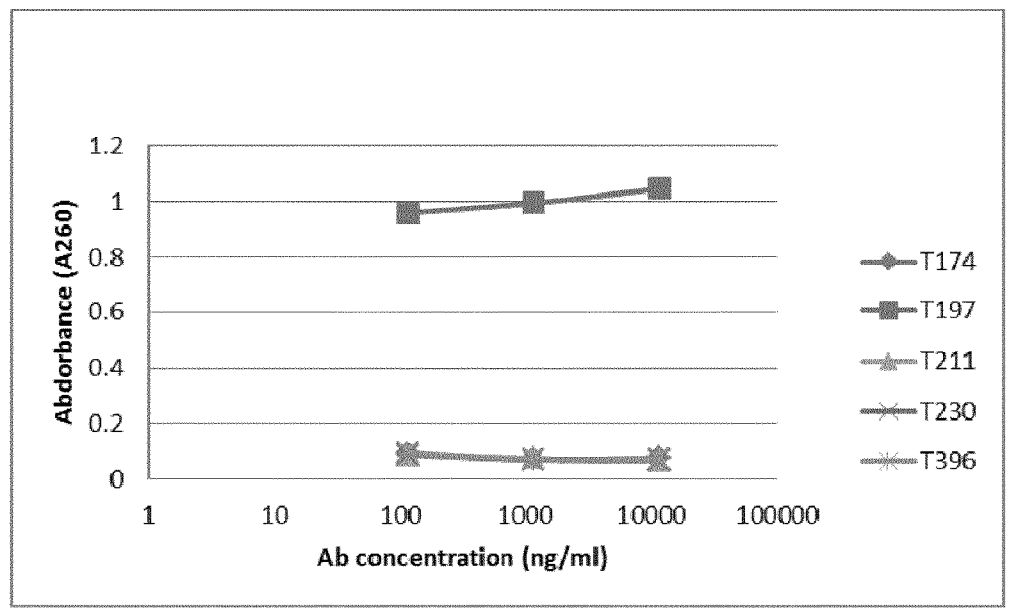

Specification includes a Sequence Listing.

(56) References Cited

OTHER PUBLICATIONS

Written Opinion in International Application No. PCT/EP2016/065809, dated Sep. 12, 2016, pp. 1-10.
Allowed claims of U.S. Appl. No. 15/742,087, 2018, pp. 1-7.
Adair, J.R. et al. "Therapeutic Antibodies" *Drug Design Reviews,* 2005, pp. 1-11, vol. 2, No. 3.
Angal, S. et al. "A Single Amino Acid Substitution Abolishes the Heterogeneity of Chimeric Mouse/Human (IgG4) Antibody" *Molecular Immunology,* 1993, pp. 105-108, vol. 30, No. 1.
Garber, E. et al. "A broad range of Fab stabilities within a host of therapeutic IgGs" *Biochemical and Biophysical Research Communications,* 2007, pp. 751-757, vol. 355.
Holliger, P. et al. "Engineered antibody fragments and the rise of single domains" *Nature Biotechnology,* Sep. 2005, pp. 1126-1136, vol. 23, No. 9.
Riechmann, L. et al. "Reshaping human antibodies for therapy" *Nature,* Mar. 24, 1988, pp. 323-327, vol. 332.
Verma, R. et al. "Antibody engineering: Comparison of bacterial, yeast, insect and mammalian expression systems" *Journal of Immunological Methods,* 1998, pp. 165-181, vol. 216.

\* cited by examiner

Figure 3
A)
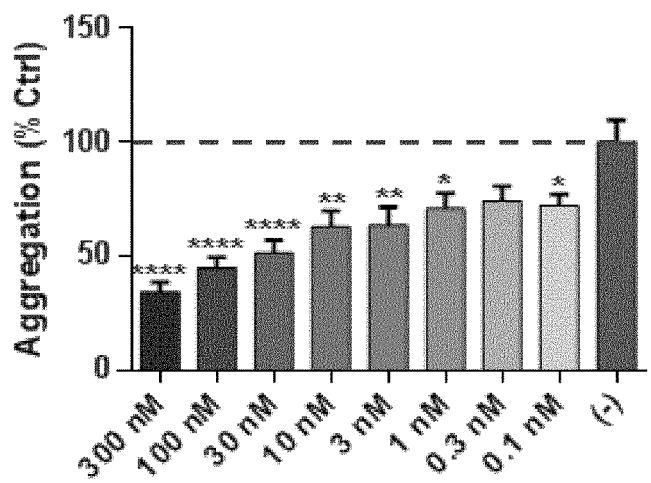
B)
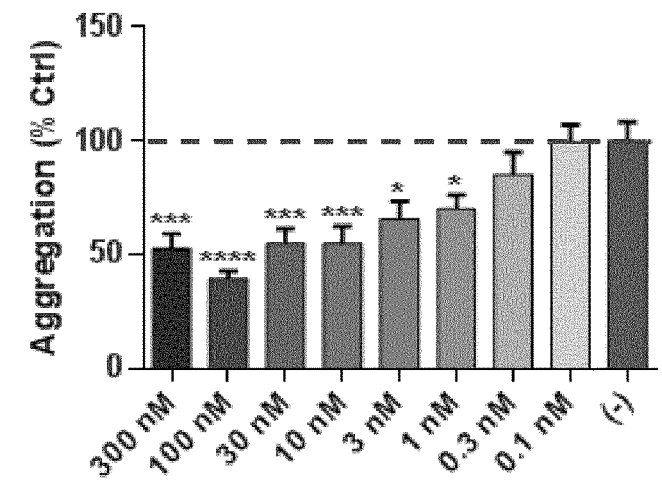
C)
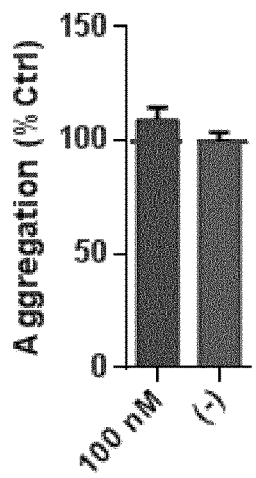

Figure 5

LIGHT CHAIN Graft AB1

```
         1       5      10      15      20      25      30      35      40      45      50      55      60      65      70      75      80      85      90    95abc   100     105
A) AB1_VL
DVVMTQTPASVEAAVGGTVTIKCQASQSVSSYYLAWYQQKPGQPPKLLIYAASYLASGVPSRFKGSGSGTEFTLTISDLECADAATYCQQGYTRTDIDNTFGGGTKVVVE B) IGKV1-39
DIQMTQSPSSLSASVGDRVTITCRASQSISSYLNWYQQKPGKAPKLLIYAASSLQSGVPSRFSGSGSGTDFTLTISSLQPEDFATYYCQQSYST---PLTFGGGTKVEIK C) gVL4_AB1
DIQMTQSPSSLSASVGDRVTITCQASQSVSSYYLAWYQQKPGKAPKLLIYAASYLASGVPSRFSGSGSGTDFTLTISSLQPEDFATYYCQQGYTRTDIDNTFGGGTKVEIK D) gVL9_AB1
DIQMTQSPSSLSASVGDRVTITCQASQSVSSYYLAWYQQKPGKAPKLLIYAASYLASGVPSRFSGSGSGTDFTLTISSLQPEDFATYYCQQAYTRTDIDNTFGGGTKVEIK
```

Figure 6

HEAVY CHAIN Graft AB1

```
       1     5    10    15    20    25    30 ab  35        40    45    50    55    60    65    70    75    80  abc 85    90    95   100abcd 105   110
A) VH_AB1
  -QSLEESGGRLVTPGTPLTLTCTVSGIDLST---WRMNWVRQAPGKGLEWIGIIGTGGRTYYANWAKGRFTISKTST---TVDLKVTSPTTEDTATYFCARLGANNNGYPLDLWGPGTLVTVSS B) IGHV4-39
  QLQLQESGPGLVKPSETLSLTCTVSGGSISISSSSYYWGWIRQPPGKGLEWIGSIYYSGSTYYNPSLKSRVTISVDTSKNQFSLKLSSVTAADTAVYYCAR----------YFDYWGQGTLVTVSS C)
gVH41_AB1
  ELQLQESGPGLVKPSETLSLTCTVSGIDLST---WRMNWIRQPPGKGLEWIGIIGTGGRTYYANWAKGRVTISRDTSKNQVSLKLSSVTAADTAVYYCARLGANNQGYPLDLWGQGTLVTVSS D) gVH49_AB1
  ELQLQESGPGLVKPSETLSLTCTVSGIDLST---WRMNWIRQPPGKGLEWIGIIGTGGRTYYANWAKGRVTISRDTSKNQVSLKLSSVTAADTAVYYCARLGANNAGYPLDLWGQGTLVTVSS
```

The N-terminal Glutamine residue is replaced with Glutamic acid, and is shown in bold and highlighted: E1.

SEQUENCE LISTING

```
<160> NUMBER OF SEQ ID NOS: 65

<210> SEQ ID NO 1
<211> LENGTH: 11
<212> TYPE: PRT
<213> ORGANISM: Artificial Sequence
<220> FEATURE:
<223> OTHER INFORMATION: CDR-L1

<400> SEQUENCE: 1

Gln Ala Ser Gln Ser Val Ser Ser Tyr Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: CDR-L2

<400> SEQUENCE: 2

Ala Ala Ser Tyr Leu Ala Ser
1               5

<210> SEQ ID NO 3
<211> LENGTH: 12
<212> TYPE: PRT
<213> ORGANISM: Artificial Sequence
<220> FEATURE:
<223> OTHER INFORMATION: CDR-L3
<220> FEATURE:
<221> NAME/KEY: MISC_FEATURE
<222> LOCATION: (3)..(3)
<223> OTHER INFORMATION: Xaa can be A or G

<400> SEQUENCE: 3

Gln Gln Xaa Tyr Thr Arg Thr Asp Ile Asp Asn Thr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: CDR-H1

<400> SEQUENCE: 4

Gly Ile Asp Leu Ser Thr Trp Arg Met Asn
1               5                   10

<210> SEQ ID NO 5
<211> LENGTH: 16
<212> TYPE: PRT
<213> ORGANISM: Artificial Sequence
<220> FEATURE:
<223> OTHER INFORMATION: CDR-H2
```

```
<400> SEQUENCE: 5

Ile Ile Gly Thr Gly Gly Arg Thr Tyr Tyr Ala Asn Trp Ala Lys Gly
1               5                   10                  15

<210> SEQ ID NO 6
<211> LENGTH: 12
<212> TYPE: PRT
<213> ORGANISM: Artificial Sequence
<220> FEATURE:
<223> OTHER INFORMATION: CDR-H3
<220> FEATURE:
<221> NAME/KEY: MISC_FEATURE
<222> LOCATION: (6)..(6)
<223> OTHER INFORMATION: Xaa can be A, Q, N, D or S

<400> SEQUENCE: 6

Leu Gly Ala Asn Asn Xaa Gly Tyr Pro Leu Asp Leu
1               5                   10

<210> SEQ ID NO 7
<211> LENGTH: 110
<212> TYPE: PRT
<213> ORGANISM: Rabbit
<220> FEATURE:
<221> NAME/KEY: MISC_FEATURE
<222> LOCATION: (91)..(91)
<223> OTHER INFORMATION: Xaa can be A or G

<400> SEQUENCE: 7

Asp Val Val Met Thr Gln Thr Pro Ala Ser Val Glu Ala Ala Val Gly
1               5                   10                  15

Gly Thr Val Thr Ile Lys Cys Gln Ala Ser Gln Ser Val Ser Ser Tyr
            20                  25                  30

Leu Ala Trp Tyr Gln Gln Lys Pro Gly Gln Pro Pro Lys Leu Leu Ile
        35                  40                  45

Tyr Ala Ala Ser Tyr Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Gln Xaa Tyr Thr Arg Thr Asp
                85                  90                  95

Ile Asp Asn Thr Phe Gly Gly Gly Thr Lys Val Val Val Glu
            100                 105                 110

<210> SEQ ID NO 8
<211> LENGTH: 117
<212> TYPE: PRT
<213> ORGANISM: Rabbit
<220> FEATURE:
<221> NAME/KEY: MISC_FEATURE
<222> LOCATION: (100)..(100)
<223> OTHER INFORMATION: Xaa can be A, Q, N, D or S

<400> SEQUENCE: 8

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Thr Trp Arg
            20                  25                  30

Met Asn Trp Val Arg Gln Ala Pro Gly Lys Gly Leu Glu Trp Ile Gly
        35                  40                  45

Ile Ile Gly Thr Gly Gly Arg Thr Tyr Tyr Ala Asn Trp Ala Lys Gly
    50                  55                  60
```

```
Arg Phe Thr Ile Ser Lys Thr Ser Thr Val Asp Leu Lys Val Thr
 65                  70                  75                  80

Ser Pro Thr Thr Glu Asp Thr Ala Thr Tyr Phe Cys Ala Arg Leu Gly
                 85                  90                  95

Ala Asn Asn Xaa Gly Tyr Pro Leu Asp Leu Trp Gly Pro Gly Thr Leu
            100                 105                 110

Val Thr Val Ser Ser
        115

<210> SEQ ID NO 9
<211> LENGTH: 110
<212> TYPE: PRT
<213> ORGANISM: Artificial Sequence
<220> FEATURE:
<223> OTHER INFORMATION: murinised

<400> SEQUENCE: 9

Asp Val Val Met Thr Gln Ser Pro Ala Ser Leu Ala Val Ser Leu Gly
 1                5                  10                  15

Gln Arg Ala Thr Ile Ser Cys Gln Ala Ser Gln Ser Val Ser Ser Tyr
                20                  25                  30

Leu Ala Trp Tyr Gln Gln Lys Pro Gly Gln Pro Pro Lys Leu Leu Ile
             35                  40                  45

Tyr Ala Ala Ser Tyr Leu Ala Ser Gly Val Pro Ser Arg Phe Lys Gly
 50                  55                  60

Ser Gly Ser Gly Thr Glu Phe Thr Leu Asn Ile His Pro Val Glu Glu
 65                  70                  75                  80

Glu Asp Ala Ala Thr Tyr Tyr Cys Gln Gln Gly Tyr Thr Arg Thr Asp
                 85                  90                  95

Ile Asp Asn Thr Phe Gly Gly Gly Thr Lys Leu Glu Ile Lys
            100                 105                 110

<210> SEQ ID NO 10
<211> LENGTH: 118
<212> TYPE: PRT
<213> ORGANISM: Artificial Sequence
<220> FEATURE:
<223> OTHER INFORMATION: murinised

<400> SEQUENCE: 10

Gln Val Gln Leu Lys Glu Ser Gly Pro Gly Leu Val Ala Pro Ser Gln
 1                5                  10                  15

Ser Leu Ser Ile Thr Cys Thr Val Ser Gly Ile Asp Leu Ser Thr Trp
                20                  25                  30

Arg Met Asn Trp Val Arg Gln Pro Pro Gly Lys Gly Leu Glu Trp Ile
             35                  40                  45

Gly Ile Ile Gly Thr Gly Gly Arg Thr Tyr Tyr Ala Asn Trp Ala Lys
 50                  55                  60

Gly Arg Phe Ser Ile Ser Lys Asp Ser Thr Gln Val Phe Leu Lys Met
 65                  70                  75                  80

Asn Ser Leu Gln Thr Glu Asp Thr Ala Thr Tyr Phe Cys Ala Arg Leu
                 85                  90                  95

Gly Ala Asn Asn Asn Gly Tyr Pro Leu Asp Leu Trp Gly Ala Gly Thr
            100                 105                 110

Thr Val Thr Val Ser Ser
        115
```

```
<210> SEQ ID NO 11
<211> LENGTH: 110
<212> TYPE: PRT
<213> ORGANISM: Artificial Sequence
<220> FEATURE:
<223> OTHER INFORMATION: humanized

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Val Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Tyr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Arg Thr Asp
                85                  90                  95

Ile Asp Asn Thr Phe Gly Gly Gly Thr Lys Val Glu Ile Lys
            100                 105                 110

<210> SEQ ID NO 12
<211> LENGTH: 110
<212> TYPE: PRT
<213> ORGANISM: Artificial Sequence
<220> FEATURE:
<223> OTHER INFORMATION: humanized

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Val Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Tyr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Thr Arg Thr Asp
                85                  90                  95

Ile Asp Asn Thr Phe Gly Gly Gly Thr Lys Val Glu Ile Lys
            100                 105                 110

<210> SEQ ID NO 13
<211> LENGTH: 110
<212> TYPE: PRT
<213> ORGANISM: Artificial Sequence
<220> FEATURE:
<223> OTHER INFORMATION: humanized
<220> FEATURE:
<221> NAME/KEY: MISC_FEATURE
<222> LOCATION: (91)..(91)
<223> OTHER INFORMATION: Xaa can be A or G

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Val Ser Ser Tyr
```

```
                    20                  25                  30

Leu Ala Trp Tyr Gln Gln Lys Pro Gly Lys Ala Pro Lys Leu Leu Ile
             35                  40                  45

Tyr Ala Ala Ser Tyr Leu Ala Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Xaa Tyr Thr Arg Thr Asp
                 85                  90                  95

Ile Asp Asn Thr Phe Gly Gly Gly Thr Lys Val Glu Ile Lys
                100                 105                 110

<210> SEQ ID NO 14
<211> LENGTH: 120
<212> TYPE: PRT
<213> ORGANISM: Artificial Sequence
<220> FEATURE:
<223> OTHER INFORMATION: humanized

<400> SEQUENCE: 14

Glu Leu Gln Leu Gln Glu Ser Gly Pro Gly Leu Val Lys Pro Ser Glu
 1               5                  10                  15

Thr Leu Ser Leu Thr Cys Thr Val Ser Gly Ile Asp Leu Ser Thr Trp
                20                  25                  30

Arg Met Asn Trp Ile Arg Gln Pro Pro Gly Lys Gly Leu Glu Trp Ile
             35                  40                  45

Gly Ile Ile Gly Thr Gly Gly Arg Thr Tyr Tyr Ala Asn Trp Ala Lys
         50                  55                  60

Gly Arg Val Thr Ile Ser Lys Asp Thr Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Arg Leu Gly Ala Asn Asn Gln Gly Tyr Pro Leu Asp Leu Trp Gly Gln
                100                 105                 110

Gly Thr Leu Val Thr Val Ser Ser
         115                 120

<210> SEQ ID NO 15
<211> LENGTH: 120
<212> TYPE: PRT
<213> ORGANISM: Artificial Sequence
<220> FEATURE:
<223> OTHER INFORMATION: humanized

<400> SEQUENCE: 15

Glu Leu Gln Leu Gln Glu Ser Gly Pro Gly Leu Val Lys Pro Ser Glu
 1               5                  10                  15

Thr Leu Ser Leu Thr Cys Thr Val Ser Gly Ile Asp Leu Ser Thr Trp
                20                  25                  30

Arg Met Asn Trp Ile Arg Gln Pro Pro Gly Lys Gly Leu Glu Trp Ile
             35                  40                  45

Gly Ile Ile Gly Thr Gly Gly Arg Thr Tyr Tyr Ala Asn Trp Ala Lys
         50                  55                  60

Gly Arg Val Thr Ile Ser Lys Asp Thr Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95
```

Arg Leu Gly Ala Asn Asn Ala Gly Tyr Pro Leu Asp Leu Trp Gly Gln
            100                 105                 110

Gly Thr Leu Val Thr Val Ser Ser
        115                 120

<210> SEQ ID NO 16
<211> LENGTH: 120
<212> TYPE: PRT
<213> ORGANISM: Artificial Sequence
<220> FEATURE:
<223> OTHER INFORMATION: humanized
<220> FEATURE:
<221> NAME/KEY: MISC_FEATURE
<222> LOCATION: (103)..(103)
<223> OTHER INFORMATION: Xaa can be  A, Q, N, D or S

<400> SEQUENCE: 16

Glu Leu Gln Leu Gln Glu Ser Gly Pro Gly Leu Val Lys Pro Ser Glu
1               5                   10                  15

Thr Leu Ser Leu Thr Cys Thr Val Ser Gly Ile Asp Leu Ser Thr Trp
            20                  25                  30

Arg Met Asn Trp Ile Arg Gln Pro Pro Gly Lys Gly Leu Glu Trp Ile
        35                  40                  45

Gly Ile Ile Gly Thr Gly Gly Arg Thr Tyr Tyr Ala Asn Trp Ala Lys
    50                  55                  60

Gly Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Leu Gly Ala Asn Asn Xaa Gly Tyr Pro Leu Asp Leu Trp Gly Gln
            100                 105                 110

Gly Thr Leu Val Thr Val Ser Ser
        115                 120

<210> SEQ ID NO 17
<211> LENGTH: 217
<212> TYPE: PRT
<213> ORGANISM: Artificial Sequence
<220> FEATURE:
<223> OTHER INFORMATION: humanized

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Val Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Tyr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Arg Thr Asp
                85                  90                  95

Ile Asp Asn Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro

```
Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 18
<211> LENGTH: 217
<212> TYPE: PRT
<213> ORGANISM: Artificial Sequence
<220> FEATURE:
<223> OTHER INFORMATION: humanized

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Val Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Tyr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Thr Arg Thr Asp
                85                  90                  95

Ile Asp Asn Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 19
<211> LENGTH: 217
<212> TYPE: PRT
<213> ORGANISM: Artificial Sequence
<220> FEATURE:
<223> OTHER INFORMATION: humanized
<220> FEATURE:
<221> NAME/KEY: MISC_FEATURE
<222> LOCATION: (91)..(91)
```

<223> OTHER INFORMATION: Xaa can be A or G

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Val Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Tyr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Xaa Tyr Thr Arg Thr Asp
                85                  90                  95

Ile Asp Asn Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 20
<211> LENGTH: 447
<212> TYPE: PRT
<213> ORGANISM: Artificial Sequence
<220> FEATURE:
<223> OTHER INFORMATION: humanized

<400> SEQUENCE: 20

Glu Leu Gln Leu Gln Glu Ser Gly Pro Gly Leu Val Lys Pro Ser Glu
1               5                   10                  15

Thr Leu Ser Leu Thr Cys Thr Val Ser Gly Ile Asp Leu Ser Thr Trp
            20                  25                  30

Arg Met Asn Trp Ile Arg Gln Pro Pro Gly Lys Gly Leu Glu Trp Ile
        35                  40                  45

Gly Ile Ile Gly Thr Gly Gly Arg Thr Tyr Tyr Ala Asn Trp Ala Lys
50                  55                  60

Gly Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Leu Gly Ala Asn Asn Gln Gly Tyr Pro Leu Asp Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 21
<211> LENGTH: 447
<212> TYPE: PRT
<213> ORGANISM: Artificial Sequence
<220> FEATURE:
<223> OTHER INFORMATION: humanized

<400> SEQUENCE: 21

Glu Leu Gln Leu Gln Glu Ser Gly Pro Gly Leu Val Lys Pro Ser Glu
1               5                   10                  15

Thr Leu Ser Leu Thr Cys Thr Val Ser Gly Ile Asp Leu Ser Thr Trp
            20                  25                  30

Arg Met Asn Trp Ile Arg Gln Pro Pro Gly Lys Gly Leu Glu Trp Ile
        35                  40                  45

Gly Ile Ile Gly Thr Gly Arg Thr Tyr Tyr Ala Asn Trp Ala Lys
50              55                  60

Gly Arg Val Thr Ile Ser Lys Asp Thr Ser Lys Asn Gln Val Ser Leu
65              70                  75                  80

Lys Leu Ser Ser Val Thr Ala Ala Asp Thr Ala Val Tyr Tyr Cys Ala
                85                  90                  95

Arg Leu Gly Ala Asn Asn Ala Gly Tyr Pro Leu Asp Leu Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 22
<211> LENGTH: 447

<212> TYPE: PRT
<213> ORGANISM: Artificial Sequence
<220> FEATURE:
<223> OTHER INFORMATION: humanized
<220> FEATURE:
<221> NAME/KEY: MISC_FEATURE
<222> LOCATION: (103)..(103)
<223> OTHER INFORMATION: Xaa can be  A, Q, N, D or S

<400> SEQUENCE: 22

Glu Leu Gln Leu Gln Glu Ser Gly Pro Gly Leu Val Lys Pro Ser Glu
1               5                   10                  15

Thr Leu Ser Leu Thr Cys Thr Val Ser Gly Ile Asp Leu Ser Thr Trp
            20                  25                  30

Arg Met Asn Trp Ile Arg Gln Pro Pro Gly Lys Gly Leu Glu Trp Ile
        35                  40                  45

Gly Ile Ile Gly Thr Gly Gly Arg Thr Tyr Tyr Ala Asn Trp Ala Lys
    50                  55                  60

Gly Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Leu Gly Ala Asn Asn Xaa Gly Tyr Pro Leu Asp Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

```
Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 23
<211> LENGTH: 450
<212> TYPE: PRT
<213> ORGANISM: Artificial Sequence
<220> FEATURE:
<223> OTHER INFORMATION: humanized

<400> SEQUENCE: 23

Glu Leu Gln Leu Gln Glu Ser Gly Pro Gly Leu Val Lys Pro Ser Glu
1               5                   10                  15

Thr Leu Ser Leu Thr Cys Thr Val Ser Gly Ile Asp Leu Ser Thr Trp
            20                  25                  30

Arg Met Asn Trp Ile Arg Gln Pro Pro Gly Lys Gly Leu Glu Trp Ile
        35                  40                  45

Gly Ile Ile Gly Thr Gly Gly Arg Thr Tyr Tyr Ala Asn Trp Ala Lys
    50                  55                  60

Gly Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Leu Gly Ala Asn Asn Gln Gly Tyr Pro Leu Asp Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 24
<211> LENGTH: 450
<212> TYPE: PRT
<213> ORGANISM: Artificial Sequence
<220> FEATURE:
<223> OTHER INFORMATION: humanized

<400> SEQUENCE: 24

Glu Leu Gln Leu Gln Glu Ser Gly Pro Gly Leu Val Lys Pro Ser Glu
1               5                   10                  15

Thr Leu Ser Leu Thr Cys Thr Val Ser Gly Ile Asp Leu Ser Thr Trp
            20                  25                  30

Arg Met Asn Trp Ile Arg Gln Pro Pro Gly Lys Gly Leu Glu Trp Ile
        35                  40                  45

Gly Ile Ile Gly Thr Gly Gly Arg Thr Tyr Tyr Ala Asn Trp Ala Lys
    50                  55                  60

Gly Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Leu Gly Ala Asn Asn Ala Gly Tyr Pro Leu Asp Leu Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

```
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 25
<211> LENGTH: 450
<212> TYPE: PRT
<213> ORGANISM: Artificial Sequence
<220> FEATURE:
<223> OTHER INFORMATION: humanized
<220> FEATURE:
<221> NAME/KEY: MISC_FEATURE
<222> LOCATION: (103)..(103)
<223> OTHER INFORMATION: Xaa can be A, Q, N, D or S

<400> SEQUENCE: 25

Glu Leu Gln Leu Gln Glu Ser Gly Pro Gly Leu Val Lys Pro Ser Glu
1               5                   10                  15

Thr Leu Ser Leu Thr Cys Thr Val Ser Gly Ile Asp Leu Ser Thr Trp
            20                  25                  30

Arg Met Asn Trp Ile Arg Gln Pro Pro Gly Lys Gly Leu Glu Trp Ile
        35                  40                  45

Gly Ile Ile Gly Thr Gly Gly Arg Thr Tyr Tyr Ala Asn Trp Ala Lys
    50                  55                  60

Gly Arg Val Thr Ile Ser Lys Asp Thr Ser Lys Asn Gln Val Ser Leu
```

```
            65                  70                  75                  80
        Lys Leu Ser Ser Val Thr Ala Ala Asp Thr Ala Val Tyr Tyr Cys Ala
                        85                  90                  95

Arg Leu Gly Ala Asn Asn Xaa Gly Tyr Pro Leu Asp Leu Trp Gly Gln
                    100                 105                 110

Gly Thr Leu Val Thr Val Ser Ala Ser Thr Lys Gly Pro Ser Val
                115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
        145                 150                 155                 160

Trp Asn Ser Gly Ala Leu Thr Ser Gly Val His Thr Phe Pro Ala Val
                        165                 170                 175

Leu Gln Ser Ser Gly Leu Tyr Ser Leu Ser Ser Val Val Thr Val Pro
                    180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
        225                 230                 235                 240

Pro Ser Val Phe Leu Phe Pro Pro Lys Pro Lys Asp Thr Leu Met Ile
                        245                 250                 255

Ser Arg Thr Pro Glu Val Thr Cys Val Val Val Asp Val Ser His Glu
                    260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
        305                 310                 315                 320

Glu Tyr Lys Cys Lys Val Ser Asn Lys Ala Leu Pro Ala Pro Ile Glu
                        325                 330                 335

Lys Thr Ile Ser Lys Ala Lys Gly Gln Pro Arg Glu Pro Gln Val Tyr
                    340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
        385                 390                 395                 400

Leu Asp Ser Asp Gly Ser Phe Phe Leu Tyr Ser Lys Leu Thr Val Asp
                        405                 410                 415

Lys Ser Arg Trp Gln Gln Gly Asn Val Phe Ser Cys Ser Val Met His
                    420                 425                 430

Glu Ala Leu His Asn His Tyr Thr Gln Lys Ser Leu Ser Leu Ser Pro
                435                 440                 445

Gly Lys
            450

<210> SEQ ID NO 26
<211> LENGTH: 330
<212> TYPE: DNA
<213> ORGANISM: Rabbit
```

```
<400> SEQUENCE: 26
gatgttgtga tgacccagac tccagcctcc gtggaggcag ctgtgggagg cacagtcacc    60
atcaagtgcc aggccagtca gagcgttagt agttacttag cctggtatca gcagaaacca   120
gggcagcctc ccaagctcct gatctatgct gcatcctatc tggcatccgg ggtcccatca   180
cggttcaaag gcagtggatc tgggacagag ttcactctca ccatcagcga cctggagtgt   240
gccgatgctg ccacttatta ctgtcaacag ggttatacta ggactgatat tgataatact   300
ttcggcggag ggaccaaggt ggtggtcgaa                                    330

<210> SEQ ID NO 27
<211> LENGTH: 351
<212> TYPE: DNA
<213> ORGANISM: Rabbit

<400> SEQUENCE: 27
cagtcgctgg aggagtccgg gggtcgcctg gtcacgcctg gacacccct gacactcacc     60 tgcacagtct ctggaatcga cctcagtact tggagaatga actgggtccg ccaggctcca   120
gggaaggggc tggaatggat cggaatcatt ggtactggtg gtagaacata ctacgcgaac   180
tgggcaaaag gccgattcac catctccaaa acctcgacca cggtggatct gaaggtcacc   240
agtccgacaa ccgaggacac ggccacctat ttctgtgcca gattgggtgc taataataat   300
ggttatcctt tggacttgtg gggcccgggg accctggtca ccgtctcgag t            351

<210> SEQ ID NO 28
<211> LENGTH: 330
<212> TYPE: DNA
<213> ORGANISM: Artificial Sequence
<220> FEATURE:
<223> OTHER INFORMATION: murinised

<400> SEQUENCE: 28
gatgtcgtga tgactcagtc acccgcaagc ctggctgtgt cgctgggaca gcgggctact    60
atctcgtgcc aagcgtccca gtctgtctcc tcgtacttgg cctggtatca gcagaagcca   120
ggacagccgc cgaaactcct catctacgcc gcctcatacc ttgcgtccgg agtgccttcg   180
agattcaaag gaagcggaag cggcactgag tttaccctga acatccaccc ggtggaagaa   240
gaggacgcag ccacgtacta ctgtcaacaa gggtacaccc gcaccgatat tgacaatacc   300
ttcggtggcg ggactaagct ggaaatcaag                                    330

<210> SEQ ID NO 29
<211> LENGTH: 354
<212> TYPE: DNA
<213> ORGANISM: Artificial Sequence
<220> FEATURE:
<223> OTHER INFORMATION: murinised

<400> SEQUENCE: 29
caagtgcagc tgaaagaatc aggaccggga ctggtggcac caagccagtc cctgtcgatc    60
acctgtactg tgtccggaat cgacctctcc acctggcgca tgaattgggt ccggcagcct   120
cccggaaagg gcctcgaatg gattggcatc atcggtactg ggggcagaac ttactacgcc   180
aattgggcga aggggcgctt ctcaatctcg aaagactcga cccaagtgtt cttgaagatg   240
aacagccttc agaccgagga taccgctacc tactttttgcg cgaggctggg agccaacaac   300
aacggttacc cgctcgatct gtggggagcc ggaacgactg tgactgtctc gagc          354
```

<210> SEQ ID NO 30
<211> LENGTH: 330
<212> TYPE: DNA
<213> ORGANISM: Artificial Sequence
<220> FEATURE:
<223> OTHER INFORMATION: humanized

<400> SEQUENCE: 30

```
gatatccaaa tgacccagtc cccatcctcc ctgtccgctt ctgtcggtga ccgcgtgacc      60
attacttgtc aagccagcca gtcggtgtcc tcatacctcg cctggtatca gcagaagccg     120
ggaaaggcgc ccaaactttt gatctacgcc gcctcgtacc tggcatccgg cgtgccgtca     180
agattcagcg ggtcgggctc cggaactgac ttcaccctga ccatcagcag cctgcagcct     240
gaggactttg ccacttacta ctgccagcag ggatacaccc ggaccgatat tgacaacacc     300
ttcggcgggg gaactaaggt cgaaatcaag                                      330
```

<210> SEQ ID NO 31
<211> LENGTH: 330
<212> TYPE: DNA
<213> ORGANISM: Artificial Sequence
<220> FEATURE:
<223> OTHER INFORMATION: humanized

<400> SEQUENCE: 31

```
gatatccaaa tgacccagtc cccatcctcc ctgtccgctt ctgtcggtga ccgcgtgacc      60
attacttgtc aagccagcca gtcggtgtcc tcatacctcg cctggtatca gcagaagccg     120
ggaaaggcgc ccaaactttt gatctacgcc gcctcgtacc tggcatccgg cgtgccgtca     180
agattcagcg ggtcgggctc cggaactgac ttcaccctga ccatcagcag cctgcagcct     240
gaggactttg ccacttacta ctgccagcag gcctacaccc ggaccgatat tgacaacacc     300
ttcggcgggg gaactaaggt cgaaatcaag                                      330
```

<210> SEQ ID NO 32
<211> LENGTH: 360
<212> TYPE: DNA
<213> ORGANISM: Artificial Sequence
<220> FEATURE:
<223> OTHER INFORMATION: humanized

<400> SEQUENCE: 32

```
gagctccaac tgcaagaatc cggccctggt ctggtcaagc cctccgaaac cctgagcctc      60
acctgtactg tgtccgggat cgacttgagc acctggagga tgaactggat tcgccagcca     120
ccgggaaagg gactggagtg gatcggcatt atcggtactg ggggacggac ctactacgcc     180
aattgggcaa agggcagagt gacgatttca aaggacacct cgaagaacca ggtgtccctg     240
aaactgtcct ccgtgactgc ggctgacacc gccgtgtact attgcgcccg gctggggagcc    300
aacaaccagg gctacccgct ggatctttgg ggacagggaa ccctcgtgac tgtctcgagt     360
```

<210> SEQ ID NO 33
<211> LENGTH: 360
<212> TYPE: DNA
<213> ORGANISM: Artificial Sequence
<220> FEATURE:
<223> OTHER INFORMATION: humanized

<400> SEQUENCE: 33

```
gagctccaac tgcaagaatc cggccctggt ctggtcaagc cctccgaaac cctgagcctc      60
acctgtactg tgtccgggat cgacttgagc acctggagga tgaactggat tcgccagcca     120
```

```
ccgggaaagg gactggagtg gatcggcatt atcggtactg ggggacggac ctactacgcc    180
aattgggcaa agggcagagt gacgatttca aggacacctc gaagaacca ggtgtccctg     240 aaactgtcct ccgtgactgc ggctgacacc gccgtgtact attgcgcccg gctgggagcc    300
aacaacgccg gctacccgct ggatctttgg ggacagggaa ccctcgtgac tgtctcgagt    360
```

<210> SEQ ID NO 34
<211> LENGTH: 651
<212> TYPE: DNA
<213> ORGANISM: Artificial Sequence
<220> FEATURE:
<223> OTHER INFORMATION: humanized

<400> SEQUENCE: 34

```
gatatccaaa tgacccagtc cccatcctcc ctgtccgctt ctgtcggtga ccgcgtgacc     60
attacttgtc aagccagcca gtcggtgtcc tcatacctcg cctggtatca gcagaagccg    120
ggaaaggcgc ccaaacttt gatctacgcc gcctcgtacc tggcatccgg cgtgccgtca     180
agattcagcg ggtcgggctc cggaactgac ttcaccctga ccatcagcag cctgcagcct    240
gaggactttg ccacttacta ctgccagcag ggatacaccc ggaccgatat tgacaacacc    300
ttcggcgggg gaactaaggt cgaaatcaag cggaccgtgg ccgctccctc cgtgttcatc    360
ttcccacccc tccgacgagca gcttaagtcc ggcaccgcct ccgtcgtgtg cctgctgaac    420
aacttctacc ccgcgaggc caaggtgcag tggaaggtgg acaacgccct gcagtccggc    480
aactcccagg aatccgtcac cgagcaggac tccaaggaca gcacctactc cctgtcctcc    540
accctgaccc tgtccaaggc cgactacgag aagcacaagg tgtacgcctg cgaagtgacc    600
caccagggcc tgtccagccc cgtgaccaag tccttcaacc ggggcgagtg c             651
```

<210> SEQ ID NO 35
<211> LENGTH: 651
<212> TYPE: DNA
<213> ORGANISM: Artificial Sequence
<220> FEATURE:
<223> OTHER INFORMATION: humanized

<400> SEQUENCE: 35

```
gatatccaaa tgacccagtc cccatcctcc ctgtccgctt ctgtcggtga ccgcgtgacc     60
attacttgtc aagccagcca gtcggtgtcc tcatacctcg cctggtatca gcagaagccg    120
ggaaaggcgc ccaaacttt gatctacgcc gcctcgtacc tggcatccgg cgtgccgtca     180
agattcagcg ggtcgggctc cggaactgac ttcaccctga ccatcagcag cctgcagcct    240
gaggactttg ccacttacta ctgccagcag gcctacaccc ggaccgatat tgacaacacc    300
ttcggcgggg gaactaaggt cgaaatcaag cgtacggtag cggccccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg t             651
```

<210> SEQ ID NO 36
<211> LENGTH: 1341
<212> TYPE: DNA
<213> ORGANISM: Artificial Sequence
<220> FEATURE:

<223> OTHER INFORMATION: humanized

<400> SEQUENCE: 36

| | |
|---|---|
| gagctccaac tgcaagaatc cggccctggt ctggtcaagc cctccgaaac cctgagcctc | 60 |
| acctgtactg tgtccgggat cgacttgagc acctggagga tgaactggat tcgccagcca | 120 |
| ccgggaaagg gactggagtg gatcggcatt atcggtactg ggggacggac ctactacgcc | 180 |
| aattgggcaa agggcagagt gacgatttca aggacacct cgaagaacca ggtgtccctg | 240 |
| aaactgtcct ccgtgactgc ggctgacacc gccgtgtact attgcgcccg gctgggagcc | 300 |
| aacaaccagg ctacccgct ggatctttgg ggacagggaa ccctcgtgac tgtctcgagt | 360 |
| gcctccacca agggcccctc cgtgttccct ctggccccctt gctccggtc cacctccgag | 420 |
| tctaccgccg ctctgggctg cctggtcaag gactacttcc ccgagccgt gacagtgtcc | 480 |
| tggaactctg gcgccctgac ctccggcgtg cacaccttcc ctgccgtgct gcagtcctcc | 540 |
| ggcctgtact ccctgtcctc cgtcgtgacc gtgccctcct ccagcctggg caccaagacc | 600 |
| tacacctgta acgtggacca caagccctcc aacaccaagg tggacaagcg ggtggaatct | 660 |
| aagtacggcc ctcccctgccc ccctgccct gccctgaat ttctgggcgg accttccgtg | 720 |
| ttcctgttcc cccaaagcc aaggacacc ctgatgatct cccggaccc cgaagtgacc | 780 |
| tgcgtggtgg tggacgtgtc ccaggaagat cccgaggtcc agttcaattg gtacgtggac | 840 |
| ggcgtggaag tgcacaatgc caagaccaag cccagagagg aacagttcaa ctccacctac | 900 |
| cgggtggtgt ccgtgctgac cgtgctgcac caggactggc tgaacggcaa agagtacaag | 960 |
| tgcaaggtgt ccaacaaggg cctgcccctcc agcatcgaaa agaccatctc caaggccaag | 1020 |
| ggccagcccc gcgagcccca ggtgtacacc ctgcccccta gccaggaaga tgaccaag | 1080 |
| aaccaggtgt ccctgacctg tctggtcaag ggcttctacc cctccgacat tgccgtggaa | 1140 |
| tgggagtcca acggccagcc cgagaacaac tacaagacca ccccccctgt gctggacagc | 1200 |
| gacggctcct tcttcctgta ctctcggctg accgtggaca gtccggtg caggaaggc | 1260 |
| aacgtcttct cctgctccgt gatgcacgag gccctgcaca accactacac ccagaagtcc | 1320 |
| ctgtccctga gcctgggcaa g | 1341 |

<210> SEQ ID NO 37
<211> LENGTH: 1341
<212> TYPE: DNA
<213> ORGANISM: Artificial Sequence
<220> FEATURE:
<223> OTHER INFORMATION: humanized

<400> SEQUENCE: 37

| | |
|---|---|
| gagctccaac tgcaagaatc cggccctggt ctggtcaagc cctccgaaac cctgagcctc | 60 |
| acctgtactg tgtccgggat cgacttgagc acctggagga tgaactggat tcgccagcca | 120 |
| ccgggaaagg gactggagtg gatcggcatt atcggtactg ggggacggac ctactacgcc | 180 |
| aattgggcaa agggcagagt gacgatttca aggacacct cgaagaacca ggtgtccctg | 240 |
| aaactgtcct ccgtgactgc ggctgacacc gccgtgtact attgcgcccg gctgggagcc | 300 |
| aacaacgccg ctacccgct ggatctttgg ggacagggaa ccctcgtgac tgtctcgagt | 360 |
| gcctccacca agggcccctc cgtgttccct ctggccccctt gctccggtc cacctccgag | 420 |
| tctaccgccg ctctgggctg cctggtcaag gactacttcc ccgagccgt gacagtgtcc | 480 |
| tggaactctg gcgccctgac ctccggcgtg cacaccttcc ctgccgtgct gcagtcctcc | 540 |
| ggcctgtact ccctgtcctc cgtcgtgacc gtgccctcct ccagcctggg caccaagacc | 600 |

| | |
|---|---|
| tacacctgta acgtggacca caagcccctcc aacaccaagg tggacaagcg ggtggaatct | 660 |
| aagtacggcc ctccctgccc ccctgccct gcccctgaat ttctgggcgg accttccgtg | 720 |
| ttcctgttcc ccccaaagcc caaggacacc ctgatgatct cccggacccc cgaagtgacc | 780 |
| tgcgtggtgg tggacgtgtc ccaggaagat cccgaggtcc agttcaattg gtacgtggac | 840 |
| ggcgtggaag tgcacaatgc caagaccaag cccagagagg aacagttcaa ctccacctac | 900 |
| cgggtggtgt ccgtgctgac cgtgctgcac caggactggc tgaacggcaa agagtacaag | 960 |
| tgcaaggtgt ccaacaaggg cctgccctcc agcatcgaaa agaccatctc caaggccaag | 1020 |
| ggccagcccc gcgagcccca ggtgtacacc ctgcccccta gccaggaaga gatgaccaag | 1080 |
| aaccaggtgt ccctgacctg tctggtcaag ggcttctacc cctccgacat tgccgtggaa | 1140 |
| tgggagtcca acggccagcc cgagaacaac tacaagacca cccccctgt gctggacagc | 1200 |
| gacggctcct tcttcctgta ctctcggctg accgtggaca agtcccggtg gcaggaaggc | 1260 |
| aacgtcttct cctgctccgt gatgcacgag gccctgcaca accactacac ccagaagtcc | 1320 |
| ctgtccctga gcctgggcaa g | 1341 |

<210> SEQ ID NO 38  
<211> LENGTH: 1350  
<212> TYPE: DNA  
<213> ORGANISM: Artificial Sequence  
<220> FEATURE:  
<223> OTHER INFORMATION: humanized

<400> SEQUENCE: 38

| | |
|---|---|
| gagctccaac tgcaagaatc cggccctggt ctggtcaagc cctccgaaac cctgagcctc | 60 |
| acctgtactg tgtccgggat cgacttgagc acctggagga tgaactggat tcgccagcca | 120 |
| ccgggaaagg gactggagtg gatcggcatt atcggtactg ggggacggac ctactacgcc | 180 |
| aattgggcaa agggcagagt gacgatttca aggacacct gaagaaccag gtgtccctg | 240 |
| aaactgtcct ccgtgactgc ggctgacacc gccgtgtact attgcgcccg gctgggagcc | 300 |
| aacaaccagg gctacccgct ggatctttgg ggacagggaa ccctcgtgac tgtctcgagt | 360 |
| gcctccacca agggcccctc cgtgttcccg ctcgctccat catcgaagtc taccagcgga | 420 |
| ggcactgcgg ctctcggttg cctcgtgaag gactacttcc cggagccggt gaccgtgtcg | 480 |
| tggaacagcg gagccctgac cagcggggtg cacacctttc cggccgtctt gcagtcaagc | 540 |
| ggcctttact ccctgtcatc agtggtgact gtcccgtcca gctcattggg aacccaaacc | 600 |
| tacatctgca atgtgaatca caaacctagc aacaccaagg ttgacaagaa agtcgagccc | 660 |
| aaatcgtgtg acaagactca cacttgtccg ccgtgcccgg cacccgaact gctgggaggt | 720 |
| cccagcgtct ttctgttccc tccaaagccg aaagacacgc tgatgatctc cgcacccccg | 780 |
| gaggtcactt gcgtggtcgt ggacgtgtca catgaggacc cagaggtgaa gttcaattgg | 840 |
| tacgtggatg gcgtcgaagt ccacaatgcc aaaactaagc ccagagaaga acagtacaat | 900 |
| tcgacctacc gcgtcgtgtc cgtgctcacg gtgttgcatc aggattggct gaacgggaag | 960 |
| gaatacaagt gcaaagtgtc caacaaggcg ctgccggcac cgatcgagaa aactatctcc | 1020 |
| aaagcgaagg gacagcctag ggaacctcaa gtctacacgc tgccaccatc acgggatgaa | 1080 |
| ctgactaaga atcaagtctc actgacttgt ctggtgaagg gttttaccc tagcgacatt | 1140 |
| gccgtggagt gggaatccaa cggccagcca gagaacaact acaagactac ccctccagtg | 1200 |
| ctcgactcgg atggatcgtt cttcctttac tcgaagctca ccgtggataa gtcccggtgg | 1260 |

```
cagcagggaa acgtgttctc ctgctcggtg atgcatgaag ccctccataa ccactatacc   1320
caaaagtcgc tgtccctgtc gccgggaaag                                    1350

<210> SEQ ID NO 39
<211> LENGTH: 1350
<212> TYPE: DNA
<213> ORGANISM: Artificial Sequence
<220> FEATURE:
<223> OTHER INFORMATION: humanized

<400> SEQUENCE: 39
gagctccaac tgcaagaatc cggccctggt ctggtcaagc cctccgaaac cctgagcctc     60
acctgtactg tgtccgggat cgacttgagc acctggagga tgaactggat tcgccagcca   120
ccgggaaagg gactggagtg gatcggcatt atcggtactg ggggacggac ctactacgcc   180
aattgggcaa agggcagagt gacgatttca aggacacctc gaagaaccag gtgtccctg   240 aaactgtcct ccgtgactgc ggctgacacc gccgtgtact attgcgcccg gctgggagcc   300
aacaacgccg gctacccgct ggatctttgg ggacaggaa ccctcgtgac tgtctcgagt   360
gcctccacca agggcccctc cgtgttcccg ctcgctccat catcgaagtc taccagcgga   420
ggcactgcgg ctctcggttg cctcgtgaag gactacttcc cggagccggt gaccgtgtcg   480
tggaacagcg gagccctgac cagcggggtg cacaccttc cggccgtctt gcagtcaagc   540
ggcctttact ccctgtcatc agtggtgact gtccccgtcca gctcattggg aacccaaacc   600
tacatctgca atgtgaatca caaacctagc aacaccaagg ttgacaagaa agtcgagccc   660
aaatcgtgtg acaagactca cacttgtccg ccgtgcccgg cacccgaact gctgggaggt   720
cccagcgtct ttctgttccc tccaaagccg aagacacgc tgatgatctc ccgcacccg   780 gaggtcactt gcgtggtcgt ggacgtgtca catgaggacc cagaggtgaa gttcaattgg   840
tacgtggatg gcgtcgaagt ccacaatgcc aaaactaagc ccagagaaga acagtacaat   900
tcgacctacc gcgtcgtgtc cgtgctcacg gtgttgcatc aggattggct gaacgggaag   960
gaatacaagt gcaaagtgtc caacaaggcg ctgccggcac cgatcgagaa aactatctcc  1020
aaagcgaagg gacagcctag ggaacctcaa gtctacacgc tgccaccatc acgggatgaa  1080
ctgactaaga atcaagtctc actgacttgt ctggtgaagg ggttttaccc tagcgacatt  1140
gccgtggagt gggaatccaa cggccagcca gagaacaact acaagactac ccctccagtg  1200
ctcgactcgg atggatcgtt cttcctttac tcgaagctca ccgtggataa gtcccggtgg  1260
cagcagggaa acgtgttctc ctgctcggtg atgcatgaag ccctccataa ccactatacc  1320
caaaagtcgc tgtccctgtc gccgggaaag                                   1350

<210> SEQ ID NO 40
<211> LENGTH: 132
<212> TYPE: PRT
<213> ORGANISM: Rabbit
<220> FEATURE:
<221> NAME/KEY: MISC_FEATURE
<222> LOCATION: (1)..(22)
<223> OTHER INFORMATION: Signal sequence

<400> SEQUENCE: 40

Met Asp Met Arg Ala Pro Thr Gln Leu Leu Gly Leu Leu Leu Leu Trp
1               5                   10                  15

Leu Pro Gly Ala Arg Cys Asp Val Val Met Thr Gln Thr Pro Ala Ser
            20                  25                  30

Val Glu Ala Ala Val Gly Gly Thr Val Thr Ile Lys Cys Gln Ala Ser
```

```
                    35                  40                  45
Gln Ser Val Ser Ser Tyr Leu Ala Trp Tyr Gln Gln Lys Pro Gly Gln
 50                  55                  60

Pro Pro Lys Leu Leu Ile Tyr Ala Ala Ser Tyr Leu Ala Ser Gly Val
 65                  70                  75                  80

Pro Ser Arg Phe Lys Gly Ser Gly Ser Gly Thr Glu Phe Thr Leu Thr
                 85                  90                  95

Ile Ser Asp Leu Glu Cys Ala Asp Ala Ala Thr Tyr Tyr Cys Gln Gln
                100                 105                 110

Gly Tyr Thr Arg Thr Asp Ile Asp Asn Thr Phe Gly Gly Gly Thr Lys
                115                 120                 125

Val Val Val Glu
            130

<210> SEQ ID NO 41
<211> LENGTH: 136
<212> TYPE: PRT
<213> ORGANISM: Rabbit
<220> FEATURE:
<221> NAME/KEY: MISC_FEATURE
<222> LOCATION: (1)..(19)
<223> OTHER INFORMATION: Signal sequence

<400> SEQUENCE: 41

Met Glu Thr Gly Leu Arg Trp Leu Leu Leu Val Ala Val Leu Lys Gly
  1               5                  10                  15

Val Gln Cys Gln Ser Leu Glu Glu Ser Gly Gly Arg Leu Val Thr Pro
                 20                  25                  30

Gly Thr Pro Leu Thr Leu Thr Cys Thr Val Ser Gly Ile Asp Leu Ser
                 35                  40                  45

Thr Trp Arg Met Asn Trp Val Arg Gln Ala Pro Gly Lys Gly Leu Glu
 50                  55                  60

Trp Ile Gly Ile Ile Gly Thr Gly Gly Arg Thr Tyr Tyr Ala Asn Trp
 65                  70                  75                  80

Ala Lys Gly Arg Phe Thr Ile Ser Lys Thr Ser Thr Thr Val Asp Leu
                 85                  90                  95

Lys Val Thr Ser Pro Thr Thr Glu Asp Thr Ala Thr Tyr Phe Cys Ala
                100                 105                 110

Arg Leu Gly Ala Asn Asn Asn Gly Tyr Pro Leu Asp Leu Trp Gly Pro
                115                 120                 125

Gly Thr Leu Val Thr Val Ser Ser
            130                 135

<210> SEQ ID NO 42
<211> LENGTH: 396
<212> TYPE: DNA
<213> ORGANISM: Rabbit
<220> FEATURE:
<221> NAME/KEY: misc_feature
<222> LOCATION: (1)..(66)
<223> OTHER INFORMATION: Signal sequence

<400> SEQUENCE: 42
atggacatga gggcccccac tcagctgctg gggctcctgc tgctctggct cccaggtgcc      60
agatgtgatg ttgtgatgac ccagactcca gcctccgtgg aggcagctgt gggaggcaca     120
gtcaccatca gtgccaggc cagtcagagc gttagtagtt acttagcctg gtatcagcag     180
aaaccagggc agcctcccaa gctcctgatc tatgctgcat cctatctggc atccggggtc     240
```

```
ccatcacggt tcaaaggcag tggatctggg acagagttca ctctcaccat cagcgacctg    300
gagtgtgccg atgctgccac ttattactgt caacagggtt atactaggac tgatattgat    360
aatactttcg gcggagggac caaggtggtg gtcgaa                              396
```

<210> SEQ ID NO 43
<211> LENGTH: 408
<212> TYPE: DNA
<213> ORGANISM: Rabbit
<220> FEATURE:
<221> NAME/KEY: misc_feature
<222> LOCATION: (1)..(57)
<223> OTHER INFORMATION: Signal sequence

<400> SEQUENCE: 43

```
atggagactg ggctgcgctg gcttctcctg gtcgctgtgc tcaaaggtgt ccagtgtcag    60
tcgctggagg agtccggggg tcgcctggtc acgcctggga cacccctgac actcacctgc    120
acagtctctg gaatcgacct cagtacttgg agaatgaact gggtccgcca ggctccaggg    180
aaggggctgg aatggatcgg aatcattggt actggtggta aacatacta cgcgaactgg    240 gcaaaaggcc gattcaccat ctccaaaacc tcgaccacgg tggatctgaa ggtcaccagt    300
ccgacaaccg aggacacggc cacctatttc tgtgccagat ggggtgctaa taataatggt    360
tatcctttgg acttgtgggg cccggggacc ctggtcaccg tctcgagt                 408
```

<210> SEQ ID NO 44
<211> LENGTH: 107
<212> TYPE: PRT
<213> ORGANISM: Homo sapiens

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 45
<211> LENGTH: 114
<212> TYPE: PRT
<213> ORGANISM: Homo sapiens

<400> SEQUENCE: 45

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser

```
                   50                  55                  60
Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Tyr Phe Asp Tyr Trp Gly Gln Gly Thr Leu Val Thr Val
            100                 105                 110

Ser Ser
```

```
<210> SEQ ID NO 46
<211> LENGTH: 321
<212> TYPE: DNA
<213> ORGANISM: Homo sapiens

<400> SEQUENCE: 46
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctctcac tttcggcgga   300
gggaccaagg tggagatcaa a                                             321

<210> SEQ ID NO 47
<211> LENGTH: 342
<212> TYPE: DNA
<213> ORGANISM: Homo sapiens

<400> SEQUENCE: 47
cagctgcagc tgcaggagtc gggcccagga ctggtgaagc cttcggagac cctgtccctc    60
acctgcactg tctctggtgg ctccatcagc agtagtagtt actactgggg ctggatccgc   120
cagcccccag ggaaggggct ggagtggatt gggagtatct attatagtgg gagcacctac   180
tacaacccgt ccctcaagag tcgagtcacc atatccgtag acacgtccaa gaaccagttc   240
tccctgaagc tgagctctgt gaccgccgca gacacggctg tgtattactg tgcgagatac   300
tttgactact ggggccaagg aaccctggtc accgtctcct ca                      342

<210> SEQ ID NO 48
<211> LENGTH: 12
<212> TYPE: PRT
<213> ORGANISM: Rabbit

<400> SEQUENCE: 48

Leu Gly Ala Asn Asn Asn Gly Tyr Pro Leu Asp Leu
 1               5                  10

<210> SEQ ID NO 49
<211> LENGTH: 12
<212> TYPE: PRT
<213> ORGANISM: Artificial Sequence
<220> FEATURE:
<223> OTHER INFORMATION: humanized

<400> SEQUENCE: 49

Leu Gly Ala Asn Asn Gln Gly Tyr Pro Leu Asp Leu
 1               5                  10

<210> SEQ ID NO 50
```

-continued

```
<211> LENGTH: 12
<212> TYPE: PRT
<213> ORGANISM: Artificial Sequence
<220> FEATURE:
<223> OTHER INFORMATION: humanized

<400> SEQUENCE: 50

Leu Gly Ala Asn Asn Ala Gly Tyr Pro Leu Asp Leu
1               5                   10

<210> SEQ ID NO 51
<211> LENGTH: 12
<212> TYPE: PRT
<213> ORGANISM: Artificial Sequence
<220> FEATURE:
<223> OTHER INFORMATION: humanized

<400> SEQUENCE: 51

Leu Gly Ala Asn Asn Asp Gly Tyr Pro Leu Asp Leu
1               5                   10

<210> SEQ ID NO 52
<211> LENGTH: 12
<212> TYPE: PRT
<213> ORGANISM: Artificial Sequence
<220> FEATURE:
<223> OTHER INFORMATION: humanized

<400> SEQUENCE: 52

Leu Gly Ala Asn Asn Ser Gly Tyr Pro Leu Asp Leu
1               5                   10

<210> SEQ ID NO 53
<211> LENGTH: 12
<212> TYPE: PRT
<213> ORGANISM: Rabbit

<400> SEQUENCE: 53

Gln Gln Gly Tyr Thr Arg Thr Asp Ile Asp Asn Thr
1               5                   10

<210> SEQ ID NO 54
<211> LENGTH: 12
<212> TYPE: PRT
<213> ORGANISM: Artificial Sequence
<220> FEATURE:
<223> OTHER INFORMATION: humanized

<400> SEQUENCE: 54

Gln Gln Ala Tyr Thr Arg Thr Asp Ile Asp Asn Thr
1               5                   10

<210> SEQ ID NO 55
<211> LENGTH: 441
<212> TYPE: PRT
<213> ORGANISM: Homo sapiens

<400> SEQUENCE: 55

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
```

```
                 50                  55                  60
Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
                 85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
                115                 120                 125

Ser Lys Ser Lys Asp Gly Thr Gly Ser Asp Lys Lys Ala Lys Gly
                130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
                180                 185                 190

Asp Arg Ser Gly Tyr Ser Ser Pro Gly Ser Pro Gly Thr Pro Gly Ser
                195                 200                 205

Arg Ser Arg Thr Pro Ser Leu Pro Thr Pro Pro Thr Arg Glu Pro Lys
                210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
                260                 265                 270

Gly Lys Val Gln Ile Ile Asn Lys Lys Leu Asp Leu Ser Asn Val Gln
                275                 280                 285

Ser Lys Cys Gly Ser Lys Asp Asn Ile Lys His Val Pro Gly Gly Gly
                290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
                340                 345                 350

Lys Ile Gly Ser Leu Asp Asn Ile Thr His Val Pro Gly Gly Gly Asn
                355                 360                 365

Lys Lys Ile Glu Thr His Lys Leu Thr Phe Arg Glu Asn Ala Lys Ala
                370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu
                435                 440

<210> SEQ ID NO 56
<211> LENGTH: 10
<212> TYPE: PRT
<213> ORGANISM: Artificial Sequence
```

-continued

```
<220> FEATURE:
<223> OTHER INFORMATION: modified
<220> FEATURE:
<221> NAME/KEY: MISC_FEATURE
<222> LOCATION: (1)..(1)
<223> OTHER INFORMATION: ACETYLATION and NYTROSYLATION
<220> FEATURE:
<221> NAME/KEY: MISC_FEATURE
<222> LOCATION: (1)..(1)
<223> OTHER INFORMATION: NYTROSYLATION
<220> FEATURE:
<221> NAME/KEY: MISC_FEATURE
<222> LOCATION: (2)..(2)
<223> OTHER INFORMATION: PHOSPHORYLATION
<220> FEATURE:
<221> NAME/KEY: MISC_FEATURE
<222> LOCATION: (3)..(3)
<223> OTHER INFORMATION: PHOSPHORYLATION
<220> FEATURE:
<221> NAME/KEY: MISC_FEATURE
<222> LOCATION: (5)..(6)
<223> OTHER INFORMATION: Position of Biotin Conjugation
<220> FEATURE:
<221> NAME/KEY: MISC_FEATURE
<222> LOCATION: (6)..(6)
<223> OTHER INFORMATION: PHOSPHORYLATION
<220> FEATURE:
<221> NAME/KEY: MISC_FEATURE
<222> LOCATION: (9)..(9)
<223> OTHER INFORMATION: PHOSPHORYLATION
<220> FEATURE:
<221> NAME/KEY: MISC_FEATURE
<222> LOCATION: (10)..(10)
<223> OTHER INFORMATION: AMIDATION

<400> SEQUENCE: 56

Tyr Ser Ser Pro Cys Ser Pro Gly Thr Pro
1               5                   10

<210> SEQ ID NO 57
<211> LENGTH: 10
<212> TYPE: PRT
<213> ORGANISM: Artificial Sequence
<220> FEATURE:
<223> OTHER INFORMATION: modified
<220> FEATURE:
<221> NAME/KEY: MISC_FEATURE
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: PHOSPHORYLATION
<220> FEATURE:
<221> NAME/KEY: MISC_FEATURE
<222> LOCATION: (6)..(6)
<223> OTHER INFORMATION: PHOSPHORYLATION
<220> FEATURE:
<221> NAME/KEY: MISC_FEATURE
<222> LOCATION: (8)..(8)
<223> OTHER INFORMATION: PHOSPHORYLATION
<220> FEATURE:
<221> NAME/KEY: MISC_FEATURE
<222> LOCATION: (10)..(10)
<223> OTHER INFORMATION: Position of Biotin Conjugation
<220> FEATURE:
<221> NAME/KEY: MISC_FEATURE
<222> LOCATION: (10)..(10)
<223> OTHER INFORMATION: AMIDATION

<400> SEQUENCE: 57

Arg Thr Pro Pro Lys Ser Pro Ser Ser Cys
1               5                   10

<210> SEQ ID NO 58
```

```
<211> LENGTH: 217
<212> TYPE: PRT
<213> ORGANISM: Mouse

<400> SEQUENCE: 58
```

Asp Val Val Met Thr Gln Ser Pro Ala Ser Leu Ala Val Ser Leu Gly
1               5                   10                  15

Gln Arg Ala Thr Ile Ser Cys Gln Ala Ser Gln Ser Val Ser Ser Tyr
            20                  25                  30

Leu Ala Trp Tyr Gln Gln Lys Pro Gly Gln Pro Pro Lys Leu Leu Ile
        35                  40                  45

Tyr Ala Ala Ser Tyr Leu Ala Ser Gly Val Pro Ser Arg Phe Lys Gly
    50                  55                  60

Ser Gly Ser Gly Thr Glu Phe Thr Leu Asn Ile His Pro Val Glu Glu
65                  70                  75                  80

Glu Asp Ala Ala Thr Tyr Tyr Cys Gln Gln Gly Tyr Thr Arg Thr Asp
                85                  90                  95

Ile Asp Asn Thr Phe Gly Gly Gly Thr Lys Leu Glu Ile Lys Arg Thr
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
    130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215

```
<210> SEQ ID NO 59
<211> LENGTH: 442
<212> TYPE: PRT
<213> ORGANISM: Mouse

<400> SEQUENCE: 59
```

Gln Val Gln Leu Lys Glu Ser Gly Pro Gly Leu Val Ala Pro Ser Gln
1               5                   10                  15

Ser Leu Ser Ile Thr Cys Thr Val Ser Gly Ile Asp Leu Ser Thr Trp
            20                  25                  30

Arg Met Asn Trp Val Arg Gln Pro Pro Gly Lys Gly Leu Glu Trp Ile
        35                  40                  45

Gly Ile Ile Gly Thr Gly Gly Arg Thr Tyr Tyr Ala Asn Trp Ala Lys
    50                  55                  60

Gly Arg Phe Ser Ile Ser Lys Asp Ser Thr Gln Val Phe Leu Lys Met
65                  70                  75                  80

Asn Ser Leu Gln Thr Glu Asp Thr Ala Thr Tyr Phe Cys Ala Arg Leu
                85                  90                  95

Gly Ala Asn Asn Asn Gly Tyr Pro Leu Asp Leu Trp Gly Ala Gly Thr
            100                 105                 110

Thr Val Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly Lys
        435                 440

<210> SEQ ID NO 60
<211> LENGTH: 651
<212> TYPE: DNA
<213> ORGANISM: Mouse

<400> SEQUENCE: 60
gatgtcgtga tgactcagtc acccgcaagc ctggctgtgt cgctgggaca gcgggctact    60
atctcgtgcc aagcgtccca gtctgtctcc tcgtacttgg cctggtatca gcagaagcca   120
ggacagccgc cgaaactcct catctacgcc gcctcatacc ttgcgtccgg agtgccttcg   180
agattcaaag gaagcggaag cggcactgag tttacccctga acatccaccc ggtgaagaa   240 gaggacgcag ccacgtacta ctgtcaacaa gggtacaccc gcaccgatat tgacaatacc   300

```
ttcggtggcg ggactaagct ggaaatcaag cgtacggatg ctgcaccaac tgtatccatc    360
ttcccaccat ccagtgagca gttaacatct ggaggtgcct cagtcgtgtg cttcttgaac    420
aacttctacc ccaaagacat caatgtcaag tggaagattg atggcagtga acgacaaaat    480
ggcgtcctga acagttggac tgatcaggac agcaaagaca gcacctacag catgagcagc    540
accctcacgt tgaccaagga cgagtatgaa cgacataaca gctatacctg tgaggccact    600
cacaagacat caacttcacc cattgtcaag agcttcaaca ggaatgagtg t             651
```

<210> SEQ ID NO 61
<211> LENGTH: 1326
<212> TYPE: DNA
<213> ORGANISM: Mouse

<400> SEQUENCE: 61

```
caagtgcagc tgaaagaatc aggaccggga ctggtggcac aagccagtc cctgtcgatc     60 acctgtactg tgtccggaat cgacctctcc acctggcgca tgaattgggt ccggcagcct   120
cccggaaagg gcctcgaatg gattggcatc atcggtactg ggggcagaac ttactacgcc   180
aattgggcga aggggcgctt ctcaatctcg aaagactcga cccaagtgtt cttgaagatg   240
aacagccttc agaccgagga taccgctacc tactttgcg cgaggctggg agccaacaac   300
aacggttacc cgctcgatct gtggggagcc ggaacgactg tgactgtctc gagtgccaaa   360
acgacacccc catctgtcta ccactggccc ctggatctg ctgcccaaac taactccatg    420
gtgaccctgg atgcctggt caagggctat ttccctgagc cagtgacagt gacctggaac   480
tctggatccc tgtccagcgg tgtgcacacc ttcccagctg tcctgcagtc tgacctctac   540
actctgagca gctcagtgac tgtcccctcc agcacctggc ccagcgagac cgtcacctgc   600
aacgttgccc accggccag cagcaccaag gtggacaaga aaattgtgcc cagggattgt   660
ggttgtaagc cttgcatatg tacagtccca gaagtatcat ctgtcttcat cttcccccca   720
aagcccaagg atgtgctcac cattactctg actcctaagg tcacgtgtgt tgtggtagac   780
atcagcaagg atgatcccga ggtccagttc agctggtttg tagatgatgt ggaggtgcac   840
acagctcaga cgcaaccccg ggaggagcag ttcaacagca ctttccgctc agtcagtgaa   900
cttcccatca tgcaccagga ctggctcaat ggcaaggagt tcaaatgcag ggtcaacagt   960
gcagctttcc ctgcccccat cgagaaaacc atctccaaaa ccaaaggcag accgaaggct  1020
ccacaggtgt acaccattcc acctcccaag gagcagatgg ccaaggataa agtcagtctg  1080
acctgcatga taacagactt cttccctgaa gacattactg tggagtggca gtggaatggg  1140
cagccagcgg agaactacaa gaacactcag cccatcatgg acacagatgg ctcttacttc  1200
gtctacagca agctcaatgt gcagaagagc aactgggagg caggaaatac tttcacctgc  1260
tctgtgttac atgagggcct gcacaaccac catactgaga agagcctctc ccactctcct  1320
ggtaaa                                                              1326
```

<210> SEQ ID NO 62
<211> LENGTH: 11
<212> TYPE: PRT
<213> ORGANISM: Artificial Sequence
<220> FEATURE:
<223> OTHER INFORMATION: modified
<220> FEATURE:
<221> NAME/KEY: MISC_FEATURE
<222> LOCATION: (1)..(1)
<223> OTHER INFORMATION: ACETYLATION

```
<220> FEATURE:
<221> NAME/KEY: MISC_FEATURE
<222> LOCATION: (1)..(2)
<223> OTHER INFORMATION: Position of Biotin Conjugation
<220> FEATURE:
<221> NAME/KEY: MISC_FEATURE
<222> LOCATION: (3)..(3)
<223> OTHER INFORMATION: PHOSPHORYLATION
<220> FEATURE:
<221> NAME/KEY: MISC_FEATURE
<222> LOCATION: (9)..(9)
<223> OTHER INFORMATION: PHOSPHORYLATION
<220> FEATURE:
<221> NAME/KEY: MISC_FEATURE
<222> LOCATION: (11)..(11)
<223> OTHER INFORMATION: AMIDATION

<400> SEQUENCE: 62

Cys Lys Thr Pro Pro Ala Pro Lys Thr Pro Pro
1               5                   10

<210> SEQ ID NO 63
<211> LENGTH: 9
<212> TYPE: PRT
<213> ORGANISM: Artificial Sequence
<220> FEATURE:
<223> OTHER INFORMATION: modified
<220> FEATURE:
<221> NAME/KEY: MISC_FEATURE
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: PHOSPHORYLATION
<220> FEATURE:
<221> NAME/KEY: MISC_FEATURE
<222> LOCATION: (4)..(4)
<223> OTHER INFORMATION: PHOSPHORYLATION
<220> FEATURE:
<221> NAME/KEY: MISC_FEATURE
<222> LOCATION: (7)..(7)
<223> OTHER INFORMATION: PHOSPHORYLATION
<220> FEATURE:
<221> NAME/KEY: MISC_FEATURE
<222> LOCATION: (9)..(9)
<223> OTHER INFORMATION: Position of Biotin Conjugation
<220> FEATURE:
<221> NAME/KEY: MISC_FEATURE
<222> LOCATION: (9)..(9)
<223> OTHER INFORMATION: AMIDATION

<400> SEQUENCE: 63

Arg Thr Pro Ser Leu Pro Thr Pro Cys
1               5

<210> SEQ ID NO 64
<211> LENGTH: 10
<212> TYPE: PRT
<213> ORGANISM: Artificial Sequence
<220> FEATURE:
<223> OTHER INFORMATION: modified
<220> FEATURE:
<221> NAME/KEY: MISC_FEATURE
<222> LOCATION: (1)..(1)
<223> OTHER INFORMATION: ACETYLATION
<220> FEATURE:
<221> NAME/KEY: MISC_FEATURE
<222> LOCATION: (1)..(2)
<223> OTHER INFORMATION: Position of Biotin Conjugation
<220> FEATURE:
<221> NAME/KEY: MISC_FEATURE
<222> LOCATION: (2)..(2)
<223> OTHER INFORMATION: PHOSPHORYLATION
```

```
<220> FEATURE:
<221> NAME/KEY: MISC_FEATURE
<222> LOCATION: (6)..(6)
<223> OTHER INFORMATION: PHOSPHORYLATION
<220> FEATURE:
<221> NAME/KEY: MISC_FEATURE
<222> LOCATION: (9)..(9)
<223> OTHER INFORMATION: PHOSPHORYLATION
<220> FEATURE:
<221> NAME/KEY: MISC_FEATURE
<222> LOCATION: (10)..(10)
<223> OTHER INFORMATION: PHOSPHORYLATION
<220> FEATURE:
<221> NAME/KEY: MISC_FEATURE
<222> LOCATION: (10)..(10)
<223> OTHER INFORMATION: AMIDATION

<400> SEQUENCE: 64

Cys Ser Pro Val Val Ser Gly Asp Thr Ser
1               5                   10

<210> SEQ ID NO 65
<211> LENGTH: 10
<212> TYPE: PRT
<213> ORGANISM: Artificial Sequence
<220> FEATURE:
<223> OTHER INFORMATION: residues 196-206 of Tau protein

<400> SEQUENCE: 65

Tyr Ser Ser Pro Gly Ser Pro Gly Thr Pro
1               5                   10
```

TAU-BINDING ANTIBODIES

CROSS-REFERENCE TO RELATED APPLICATION

This application is the U.S. national stage application of International Patent Application No. PCT/EP2016/065809, filed Jul. 5, 2016.

The Sequence Listing for this application is labeled "Seq-List.txt" which was created on Jan. 4, 2018 and is 79 KB. The entire content of the sequence listing is incorporated herein by reference in its entirety.

FIELD OF THE INVENTION

The present invention relates inter alia to therapeutic and diagnostic Tau-binding antibodies and binding fragments thereof, methods of making such antibodies and their use for treating and/or diagnosing tauopathies such as Alzheimer's disease; Amyotrophic lateral sclerosis/parkinsonism-dementia complex; Argyrophilic grain disease; Chronic traumatic encephalopathy; Corticobasal degeneration; Diffuse neurofibrillary tangles with calcification; Down syndrome; Familial British dementia; Familial Danish dementia; Frontotemporal dementia and parkinsonism linked to chromosome 17 caused by MAPT mutations; Gerstmann-Sträussler-Scheinker disease; Guadeloupean parkinsonism; Myotonic dystrophy; Neurodegeneration with brain iron accumulation; Niemann-Pick disease, type C; Non-Guamanian motor neuron disease with neurofibrillary tangles; Pick disease; Postencephalitic parkinsonism; Prion protein cerebral amyloid angiopathy; Progressive subcortical gliosis; Progressive supranuclear palsy; SLC9A6-related mental retardation; Subacute sclerosing panencephalitis; Tangle-only dementia; White matter tauopathy with globular glial inclusions (Clavaguera et al. Brain Pathology 23 (2013) 342-349). The present invention also relates to methods of treating a human subject suffering from or being suspected to be prone to tauopathies described above, in particular tauopathies such as Alzheimer's disease and progressive supranuclear palsy.

BACKGROUND OF THE INVENTION

Alzheimer's disease (AD) and progressive supranuclear (PSP) are neurodegenerative diseases with high medical unmet needs, high cost for the societies' health systems, and high burden for the families affected. AD clinical signs include loss of memory, cognition, reasoning, judgment and emotional stability and ultimately death. PSP involves serious and progressive gait control and balance issues, falls, vertical eyes movement disturbances, cognitive problems, depression, apathy, and mild dementia. Late symptoms include blurring of vision, uncontrolled eye movement, slurred speech, difficulty swallowing and death.

For more than a decade AD disease modification programs have targeted the amyloid-beta-peptide through various mechanisms. In contrast, much less progress has been made in addressing intracellular Tau pathology, the second major hallmark for AD. Neurofibrillary inclusions or tangles containing aggregated, hyperphosphorylated Tau are defining characteristics of AD pathology and a number of other tauopathies, including PSP.

In these diseases there is a strong correlation between symptomatic progression and the level and distribution of intraneural Tau aggregates. In AD neuronal Tau tangles first appear in the transentorhinal cortex, from where they spread to the hippocampus and neocortex. The tangles observed in AD neurons consist of hyperphosphorylated, aggregated insoluble Tau. Direct toxic effects of the pathological Tau species and/or loss of axonal transport due to sequestration of functional Tau into hyperphosphorylated and aggregated forms, which are no longer capable of supporting axonal transport, have been proposed to contribute to the disease.

In its non-pathological state, Tau is a highly soluble cytoplasmic microtubule-binding protein, which occurs in the human central nervous system (CNS) in 6 main isoforms due to alternative splicing, ranging from 352 to 441 amino acids in length. These isoforms can have zero, one or two N-terminal inserts (0N, 1N, 2N), and either three or four C-terminal "repeat" sequences (3R or 4R). These 30-32 amino acid C-terminal repeat sequences, R1, R2, R3 and R4, together constitute the Tau microtubule-binding region (MTBR). Indeed the main role of Tau is believed to be in the assembly and stabilization of axonal microtubules. Microtubules form tracks for axonal transport and cytoskeletal elements for cell growth (Clavaguera et al., Brain Pathology 23 (2013) 342-349). Three Tau isoforms have been demonstrated to contain three microtubule binding regions (MTBR):

isoform 4, also referred to as 3R0N, NCBI Reference Sequence NP 058525.1 (352 amino acid),
isoform 7, also referred to as 3R1N, NCBI Reference Sequence NP 001190180.1 (381 amino acid)
isoform 8, also referred to as 3R2N, NCBI Reference Sequence NP 001190181.1 (410 amino acid).

Whereas the other three Tau isoforms contain four MTBRs:

isoform 2, also referred to as 4R2N, NCBI Reference Sequence NP 005901.2 (441 amino acid),
isoform 3, also referred to as 4R0N, NCBI Reference Sequence NP 058518.1 (383 amino acid), and
isoform 5, also referred to as 4R1N, NCBI Reference Sequence NP 001116539.1 (412 amino acid).

Tau contains 85 potential serine (S), threonine (T), and tyrosine (Y) phosphorylation sites. Many of the phosphorylated residues on Tau are found in the proline-rich domain of Tau, flanking the microtubule-binding domain. All six Tau isoforms are present in normal mature human brain, and at this stage Tau phosphorylation is relatively reduced (Noble et al., 2013 Front Neurol. 2013; 4: 83). In the various tauopathies, deposited Tau in pathological lesions is invariably highly phosphorylated. Phospho-Serine202 and phosphor-Threonine205 have been detected in aggregated Tau from brain samples and cerebrospinal fluid from PSP and AD patients (Buée et al., Brain Research Reviews 33 (2000) 95-130; Wray et al J Neurochem. 2008 Jun. 1; 105(6):2343-52; Hanger et al., J Biol Chem. 2007 Aug. 10; 282(32): 23645-54; Maccioni et al Neurobiol Aging. 2006 February; 27(2):237-44).

Only symptomatic treatments are currently available for these diseases with mild or no efficacy. No treatment is currently available for slowing or ideally stopping the development of the disease. Therefore there remains a need in the art for new compounds and compositions useful in the treatment of tauopathies.

OBJECTIVES AND SUMMARY OF THE INVENTION

It is an objective of the present invention to inter alia provide agents for treating or diagnosing tauopathies such as Alzheimer's disease (AD) or progressive supranuclear palsy (PSP). Further, it is an objective of the present invention to provide inter alia methods of treating or diagnosing tauopathies such as Alzheimer's disease (AD) or progressive supranuclear palsy (PSP).

These and other objectives as they will become apparent from the ensuing description hereinafter are attained by the subject matter of the independent claims. Some of the specific aspects and embodiments thereof contemplated by the present disclosure form the subject matter of the dependent claims. Yet other aspects and embodiments thereof as contemplated by the present disclosure may be taken from the ensuing description.

In a first aspect, the present disclosure provides an isolated Tau-binding antibody or binding fragment thereof, wherein said Tau-binding antibody or binding fragment thereof comprises
a light chain variable region comprising a CDR1 selected from SEQ ID No.: 1 or sequences at least 90% identical thereto, a CDR2 selected from SEQ ID No.: 2 or sequences at least 90% identical thereto, and a CDR3 selected from SEQ ID No.: 3 or sequences at least 90% identical thereto; and/or
a heavy chain variable region comprising a CDR1 selected from SEQ ID No.: 4 or sequences at least 90% identical thereto, a CDR2 selected from SEQ ID No.: 5 or sequences at least 90% identical thereto, and a CDR3 selected from SEQ ID No.: 6 or sequences at least 90% identical thereto.

In a second aspect, the present disclosure provides an isolated Tau-binding antibody or binding fragment thereof, wherein said Tau-binding antibody or binding fragment thereof comprises
a light chain variable region comprising SEQ ID No.: 7 or sequences at least 80% identical thereto, and/or
a heavy chain variable region comprising SEQ ID No.: 8 or sequences at least 80% identical thereto.

In a third aspect, the present disclosure provides an isolated Tau-binding antibody or binding fragment thereof, wherein said Tau-binding antibody or binding fragment thereof comprises
a light chain variable region comprising SEQ ID No.: 9 or sequences at least 80% identical thereto, and/or
a heavy chain variable region comprising SEQ ID No.: 10 or sequences at least 80% identical thereto.

In a fourth aspect the present disclosure provides an isolated Tau-binding antibody or binding fragment thereof, wherein said Tau-binding antibody or binding fragment thereof comprises
a light chain variable region comprising SEQ ID No.: 13 or sequences at least 80% identical thereto, and/or
a heavy chain variable region comprising SEQ ID No.: 16 or sequences at least 80% identical thereto.

In a fifth aspect the present disclosure provides an isolated Tau-binding antibody or binding fragment thereof, wherein said Tau-binding antibody or binding fragment binds to a phosphorylated Tau fragment comprising amino acids 197 to 206 of SEQ ID NO: 55.

As an embodiment of the first and fifth aspect, the disclosure provides for antibodies or binding fragments thereof, which can be chimeric, humanized or fully human antibodies or binding fragments thereof.

As an embodiment of the second or third aspect, the disclosure provides for antibodies or binding fragments thereof, which can be chimeric antibodies or binding fragments thereof.

As an embodiment of the fourth aspect, the disclosure provides for antibodies or binding fragments thereof, which can be humanized antibodies or binding fragments thereof.

In a sixth aspect the present disclosure provides an isolated Tau-binding antibody or binding fragment thereof, wherein said Tau-binding antibody or binding fragment thereof competes for binding to Tau with a Tau-binding antibody or binding fragment thereof of any of the first to fourth aspects and the embodiments thereof.

In a seventh aspect the present disclosure provides an isolated Tau-binding antibody or binding fragment thereof, wherein said Tau-binding antibody or binding fragment thereof binds to substantially the same epitope of Tau as a Tau-binding antibody or binding fragment thereof of any of the first to fifth aspects and the embodiments thereof.

As an embodiment of the sixth and seventh aspect, the disclosure provides for monoclonal antibodies or binding fragments thereof, which are humanized antibodies or binding fragments thereof.

Antibodies and binding fragments thereof of the first to seventh aspects and the embodiments thereof are capable of binding to soluble forms of human Tau, paired helical filaments (PHF) of human Tau or to both soluble forms of human Tau and paired helical filaments (PHF) of human Tau that comprise a phosphorylated Tau region within amino acids 197 to 206 of SEQ ID NO: 55.

In an eighth aspect the present disclosure provides nucleic acid molecules comprising nucleic acid sequences such as DNA sequences coding for the heavy and/or light chain of an antibody or binding fragment of the first to seventh aspects and the embodiments thereof.

In a ninth aspect the present disclosure provides cloning or expression vectors comprising these aforementioned nucleic acid molecules.

In a tenth aspect the present disclosure provides host cells comprising these afore mentioned nucleic acid molecules, cloning vectors or expression vectors.

In an eleventh aspect the present disclosure provides methods of producing antibodies and binding fragments thereof of the first to seventh aspects and the embodiments thereof.

An twelfth aspect of the disclosure relates to the use of antibodies and binding fragments thereof of the first to seventh aspects and the embodiments thereof for treating tauopathies such as in particular AD and PSP.

Another aspect of the disclosure relates to the use of antibodies and binding fragments thereof of the first to seventh aspects and the embodiments thereof for diagnosing tauopathies such as in particular AD and PSP.

FIGURE LEGENDS

FIG. 1: Binding of AB1 having a rabbit VL sequence (VL_AB1) of SEQ ID No.: 7 and a rabbit VH sequence (VH_AB1) of SEQ ID No.: 8 to biotinylated T197 peptide versus binding to biotinylated peptides T174, T211, T230 and T396 in the ELISA assay of Experiment 2.3.

Figure 2:
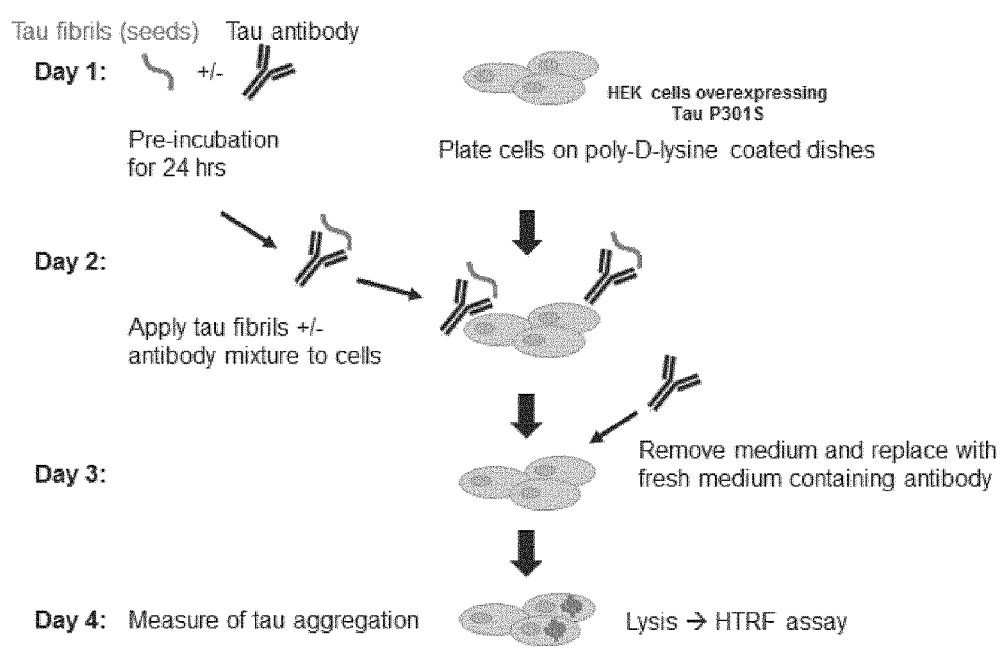

FIG. 2: Diagram illustrating the cellular aggregation assay of Experiment 3.1.

FIG. 3: Efficacy of Tau-binding antibodies having a light chain of SEQ ID No.: 17 and a heavy chain of SEQ ID No.:20 (A), and of a Tau-binding antibody having a light chain of SEQ ID No.: 17 and a heavy chain of SEQ ID No.:21 (B), or a negative control IgG4 antibody A33 (C) in a cellular Tau aggregation assay using human Tau pathological fibrils recovered from human PSP patients (PSP-PHF8) as seeds.

Figure 4:
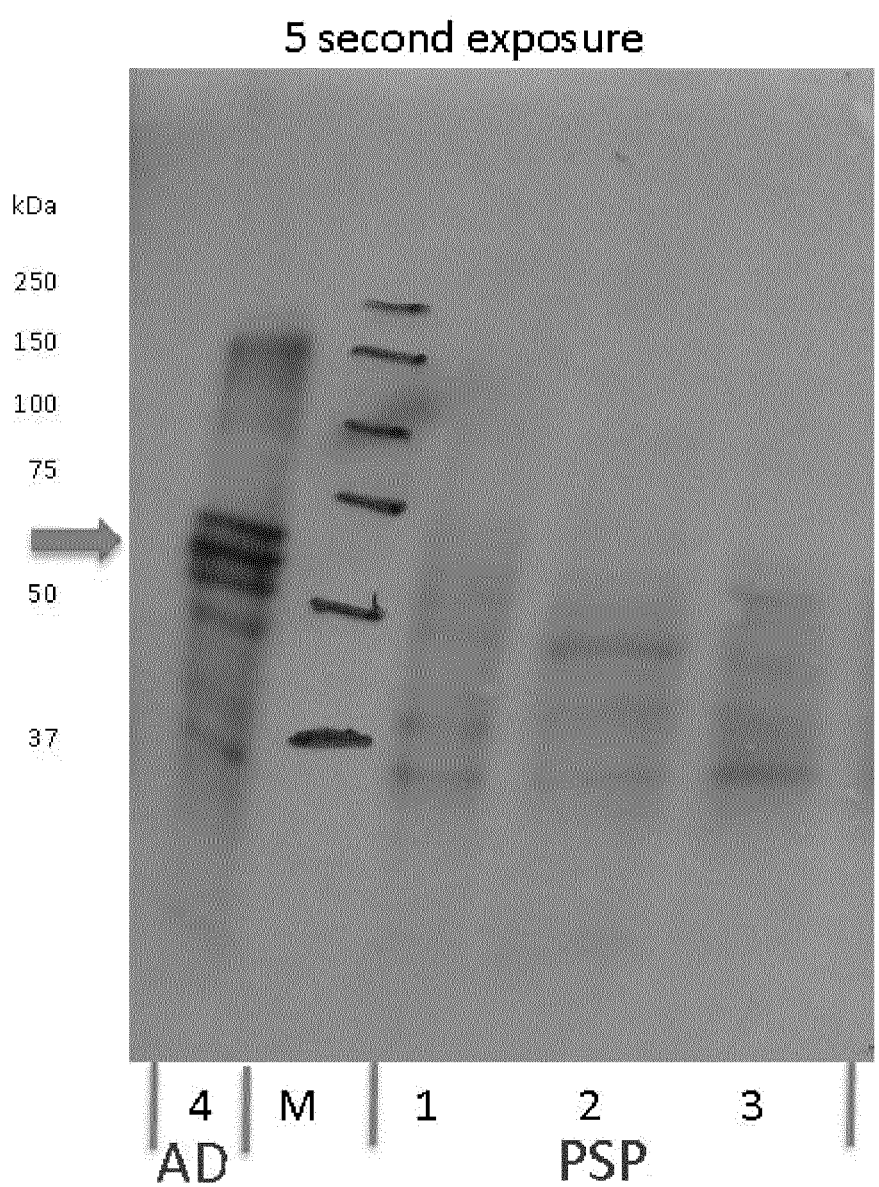

FIG. 4: Western blot showing binding properties of a Tau-binding antibody AB1 having a light chain of SEQ ID No.: 9 and the heavy chain of SEQ ID No.: 10, to Tau-containing lysates from human AD, or PSP.

FIG. 5: A) depicts the donor VL of AB1 (VL_AB1) of SEQ ID No.: 7 with CDRs 1 (SEQ ID No.: 1), 2 (SEQ ID No.: 2) and 3 (SEQ ID No.: 53) being underlined. B) depicts the VL sequence of the human acceptor region IGKV1-39 of SEQ ID No.: 44 with acceptor CDRs 1, 2, and 3 being underlined. C) depicts the CDR grafted sequence gVL4_AB1 of SEQ No.: 11 with CDRs 1 (SEQ ID No.: 1), 2 (SEQ ID No.: 2) and 3 (SEQ ID No.: 53) being underlined. D) depicts the CDR grafted sequence gVL9_AB1 of SEQ No.: 12 with CDRs 1 (SEQ ID No.: 1), 2 (SEQ ID No.: 2) and 3 (SEQ ID No.: 54) being underlined; CDR3 comprises a A91 mutation compared to VL_AB1.

FIG. 6: A) depicts the donor VH of AB1 (VH_AB1) of SEQ ID No.: 8 with CDRs 1 (SEQ ID No.: 4), 2 (SEQ ID No.: 5) and 3 (SEQ ID No.: 48) being underlined. B) depicts the VH sequence of the human acceptor region IGHV4-39 of SEQ ID No.: 45 with acceptor CDRs 1, 2, and 3 being underlined. C) depicts the CDR grafted sequence gVH41_AB1 of SEQ No.: 14 with CDRs 1 (SEQ ID No.: 4), 2 (SEQ ID No.: 5) and 3 (SEQ ID No.: 49) being underlined. Donor residues are shown in italic and bold: K71 and V78. Mutations in the framework are highlighted (E1). CDR3 comprises a N100Q substitution compared to VH_AB1 D) depicts the CDR grafted sequence gVH49_AB1 of SEQ No.: 15 with CDRs 1 (SEQ ID No.: 4), 2 (SEQ ID No.: 5) and 3 (SEQ ID No.: 50) being underlined. Donor residues are shown in italic and bold (K71 and V78). Mutations in the framework are highlighted (E1). CDR3 comprises a N100A substitution compared to VH_AB1.

Figure 7:
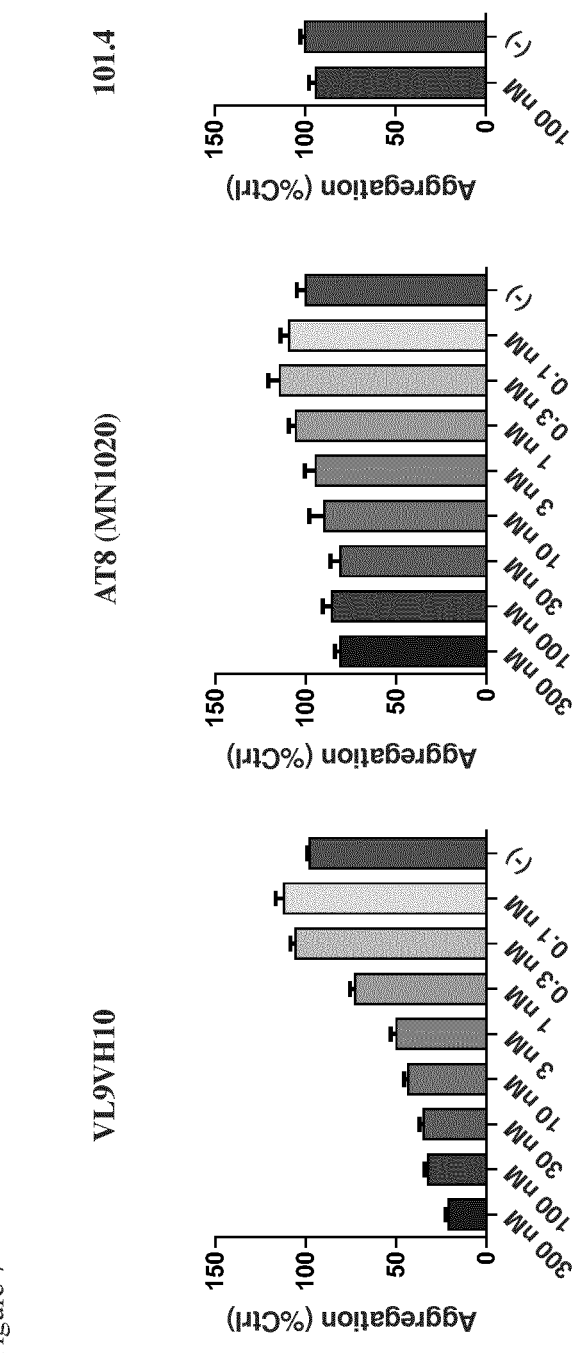

FIG. 7: Efficacy of Tau-binding antibodies having a light chain of SEQ ID No.: 9 and a heavy chain of SEQ ID No.:10, and of a Tau-binding antibody AT8 described in the literature as binding to an epitope comprising phosphorylated residues 202 and 205 of SEQ ID NO: 55, or a negative control antibody 101.4 in a cellular Tau aggregation assay using human Tau pathological fibrils recovered from human AD patients as seeds.

Figure 8:
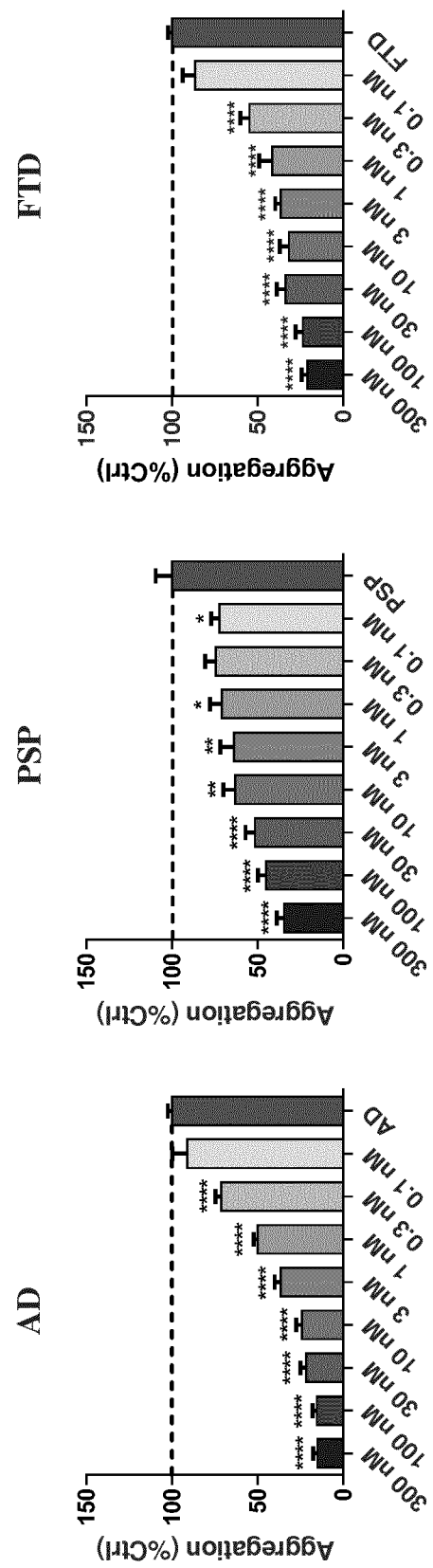

FIG. 8: Efficacy of Tau-binding antibodies having a light chain of SEQ ID NO: 17 and a heavy chain of SEQ ID NO:20 in a cellular Tau aggregation assay using human Tau pathological fibrils recovered from human AD patients, or human PSP patients or human FTD patients as seeds.

DETAILED DESCRIPTION OF THE INVENTION

The present disclosure as illustratively described in the following may suitably be practiced in the absence of any element or elements, limitation or limitations, not specifically disclosed herein.

The present disclosure will be described with respect to particular aspects and embodiments thereof and with reference to certain figures and examples but the invention is not limited thereby.

Technical terms are used by their common sense unless indicated otherwise. If a specific meaning is conveyed to certain terms, definitions of terms will be given in the following in the context of which the terms are used.

Where the term "comprising" is used in the present description and claims, it does not exclude other elements. For the purposes of the present disclosure, the term "consisting of" is considered to be a preferred embodiment of the term "comprising of". If hereinafter a group is defined to comprise at least a certain number of embodiments, this is also to be understood to disclose a group which preferably consists only of these embodiments.

For the purposes of the present disclosure, the term "obtained" is considered to be a preferred embodiment of the term "obtainable". If hereinafter e.g. an antibody is defined to be obtainable from a specific source, this is also to be understood to disclose an antibody which is obtained from this source.

Where an indefinite or definite article is used when referring to a singular noun, e.g. "a", "an" or "the", this includes a plural of that noun unless something else is specifically stated. The terms "about" or "approximately" denote an interval of accuracy that the person skilled in the art will understand to still ensure the technical effect of the feature in question. The term typically indicates deviation from the indicated numerical value of ±10%, and preferably of ±5%.

It is to be understood that any reference to a Tau-binding antibody or binding fragment thereof as a preferred embodiment of the various aspects contemplates monoclonal Tau-binding antibodies or binding fragments thereof.

For various aspects the present disclosure mentions antibodies and binding fragments thereof comprising CDRs and variable regions of the respective light chain and/or heavy chain regions. Antibodies or binding fragments thereof comprising just a variable light chain region or variable heavy chain region may be useful e.g. for methods of manufacturing or e.g. for screening for variable regions that can effectively associate with a corresponding other variable region. It is, however, to be understood that wherever reference is made to antibodies and binding fragments thereof comprising CDRs and variable regions of the respective light chain and/or heavy chain regions, this always contemplates as a preferred embodiment antibodies and binding fragments thereof comprising CDRs and variable regions of the respective light chain and heavy chain regions.

As used herein, the terms "treatment", "treating" and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. Treatment thus covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

A reference to a Tau-binding antibody or binding fragment thereof as "a therapeutically active agent" refers to the use of a Tau-binding antibody or binding fragment thereof in the treatment of a disease.

A "therapeutically effective amount" refers to the amount of a Tau-binding antibody or binding fragment thereof that, when administered to a mammal or other subject for treating a disease, is sufficient to effect such treatment for the disease. The therapeutically effective amount will vary depending on the Tau-binding antibody or binding fragment thereof, the disease and its severity and the age, weight, etc., of the subject to be treated.

A reference to a Tau-binding antibody or binding fragment thereof as "a diagnostically active agent" refers to the use of a Tau-binding antibody or binding fragment thereof in the diagnosis of a disease.

A "diagnostically effective amount" refers to the amount of a Tau-binding antibody or binding fragment thereof that, when used in a diagnostic test on a biological sample is sufficient to allow identification of a disease or of monitoring the amount of disease tissue as a means of monitoring the efficacy of therapeutic intervention.

The present application is based in part on the identification of an antibody designated AB1 that binds human Tau. As is customary in the field, Tau residue numbering in this text refers to Tau isoform 2 of SEQ ID No.: 55 (NCBI reference sequence: NP 005901.2). As will be laid out hereinafter AB1, which was isolated from an immunized rabbit, and recognizes a phosphorylated Tau region within amino acids 197 to 206 of SEQ ID No.: 55.

The examples establish that AB1 is capable of binding to paired helical filaments (PHF) of human Tau (see Example 2.4) and that AB1 was capable of detecting intraneuronal neurofibrillary tangles (NFT), extraneuronal NFT, neuritic plaque-like structures and neurophil threads in cryosections of human samples (see Example 3.2). It seems reasonable to assume that this behavior is at least in part mediated by the complementarity determining regions (CDRs) of the variable light chain region (VL) and variable heavy chain region (VH) of AB1.

Against this background, the present disclosure provides for Tau-binding antibodies or binding fragments thereof comprising the CDRs or specificity determining residues of the VL region of AB1 (SEQ ID No.: 7) and/or the CDRs of the VH region of AB1 (SEQ ID No.: 8).

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. However, according to Chothia (Chothia, C. and Lesk, A. M. J. Mol. Biol., 196, 901-917 (1987)) the loop equivalent to CDR-H1 extends from residue 26 to residue 32.

CDR1, CDR2, and CDR3 of VL of AB1 were thus identified to correspond to SEQ ID Nos.: 1, 2, and 53 respectively. CDR1, CDR2, and CDR3 of VH of AB1 were thus identified to correspond to SEQ ID Nos.: 4, 5, and 48 respectively. The effect of amino acid substitutions, additions and/or deletions to the CDRs can be readily tested by one skilled in the art, for example by using the methods described in the examples. In the originally identified CDR3 of VH (CDRH3), namely SEQ ID No.: 48, for example a potential asparagine deamidation site was identified and modified by replacing the asparagine residue by either glutamine, alanine, aspartic acid or serine. This lead to sequences SEQ ID No.: 49, 50, 51 and 52 respectively for CDRH3. For the sake of brevity the three sequences for CDRH3, namely SEQ ID Nos.: 48, 49, 50, 51 and 52 were combined as SEQ ID No.: 6. Similarly, in CDR3 of VL (CDRL3) a potential glutamine deamidation site was identified and modified by replacing the contiguous glycine with alanine. This lead to sequence SEQ ID NO: 54. For the sake of brevity both sequences for CDRL3, namely SEQ ID NO: 53 and 54 were combined as SEQ ID NO: 3.

It will be appreciated that further modifications such as substitutions, additions and/or deletions may be made to the CDRs without substantially changing e.g. the binding properties compared to AB1. This may be primarily achieved by e.g. replacing amino acids in the CDRs for similar amino acids. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);
lysine, arginine and histidine (amino acids having basic side chains);
aspartate and glutamate (amino acids having acidic side chains);
asparagine and glutamine (amino acids having amide side chains); and
cysteine and methionine (amino acids having sulphur-containing side chains).

Against this background the disclosure provides in one aspect for an isolated Tau-binding antibody or binding fragment thereof, wherein said Tau-binding antibody or binding fragment thereof comprises a light chain variable region comprising a CDR1 selected from SEQ ID No.: 1 or sequences at least 90% identical thereto, a CDR2 selected from SEQ ID No.: 2 or sequences at least 90% identical thereto, and a CDR3 selected from SEQ ID No.: 3 or sequences at least 90% identical thereto; and/or a heavy chain variable region comprising a CDR1 selected from SEQ ID No.: 4 or sequences at least 90% identical thereto, a CDR2 selected from SEQ ID No.: 5 or sequences at least 90% identical thereto, and/or a CDR3 selected from SEQ ID No.: 6 or sequences at least 90% identical thereto.

In a further aspect the disclosure provides an isolated Tau-binding antibody or binding fragment thereof, wherein said Tau-binding antibody or binding fragment thereof comprises a light chain comprising a CDR1 selected from SEQ ID No.: 1 or sequences at least 90% identical thereto, a CDR2 selected from SEQ ID No.: 2 or sequences at least 90% identical thereto, and a CDR3 selected from SEQ ID No.: 3 or sequences at least 90% identical thereto; and a heavy chain.

In a further aspect the disclosure provides an isolated Tau-binding antibody or binding fragment thereof, wherein said Tau-binding antibody or binding fragment thereof comprises a light chain; and a heavy chain variable region comprising a CDR1 selected from SEQ ID No.: 4 or sequences at least 90% identical thereto, a CDR2 selected from SEQ ID No.: 5 or sequences at least 90% identical thereto, and/or a CDR3 selected from SEQ ID No.: 6 or sequences at least 90% identical thereto.

"Identity", as used herein, indicates that at any particular position in the aligned sequences, the amino acid residue is identical between the sequences. Degrees of identity can be readily calculated e.g. using the BLAST™ software available from NCBI (Altschul, S. F. et al; 1990, J. Mol. Biol. 215:403-410; Gish, W & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. k. Madden, T. L. 1997, Genome Res. 7:649-656).

The identity of CDRL1, CDRL2, CDRL3, CDRH1, CDRH2, and CDRH3 to SEQ ID Nos.: 1, 2, 3, 4, 5, and 6 respectively may be at least 90%, but may also be higher such as at least 95%, 96%, 97%, 98% or 99% with an optional preference for higher identities. Positions of different identity may be selected according to similarity considerations.

In this context the disclosure specifically considers Tau-binding antibodies or binding fragments thereof comprising a VL with CDRL1, CDRL2, and CDRL3 of SEQ ID Nos.: 1, 2, 3 respectively and a VH with CDRH1, CDRH2, and CDRH3 of SEQ ID Nos: 4, 5, and 6 respectively. The disclosure also considers Tau-binding antibodies or binding fragments thereof comprising a VL with CDRL1, CDRL2, and CDRL3 of SEQ ID Nos.: 1, 2, 53 respectively and a VH with CDRH1, CDRH2, and CDRH3 of SEQ ID Nos: 4, 5, and 6 respectively, Tau-binding antibodies or binding fragments thereof comprising a VL with CDRL1, CDRL2, and CDRL3 of SEQ ID Nos.: 1, 2, 54 respectively and a VH with CDRH1, CDRH2, and CDRH3 of SEQ ID Nos: 4, 5, and 6 respectively, Tau-binding antibodies or binding fragments thereof comprising a VL with CDRL1, CDRL2, and CDRL3 of SEQ ID Nos.: 1, 2, 3 respectively and a VH with CDRH1, CDRH2, and CDRH3 of SEQ ID Nos: 4, 5, and 48 respectively, Tau-binding antibodies or binding fragments thereof comprising a VL with CDRL1, CDRL2, and CDRL3 of SEQ ID Nos.: 1, 2, 3 respectively and a VH with CDRH1, CDRH2, and CDRH3 of SEQ ID Nos: 4, 5, and 49 respectively, Tau-binding antibodies or binding fragments thereof comprising a VL with CDRL1, CDRL2, and CDRL3 of SEQ ID Nos.: 1, 2, 3 respectively and a VH with CDRH1, CDRH2, and CDRH3 of SEQ ID Nos: 4, 5, and 50 respectively, Tau-binding antibodies or binding fragments thereof comprising a VL with CDRL1, CDRL2, and CDRL3 of SEQ ID Nos.: 1, 2, 3 respectively and a VH with CDRH1, CDRH2, and CDRH3 of SEQ ID Nos: 4, 5, and 50 respectively, Tau-binding antibodies or binding fragments thereof comprising a VL with CDRL1, CDRL2, and CDRL3 of SEQ ID Nos.: 1, 2, 3 respectively and a VH with CDRH1, CDRH2, and CDRH3 of SEQ ID Nos: 4, 5, and 51 respectively, and Tau-binding antibodies or binding fragments thereof comprising a VL with CDRL1, CDRL2, and CDRL3 of SEQ ID Nos.: 1, 2, 3 respectively and a VH with CDRH1, CDRH2, and CDRH3 of SEQ ID Nos: 4, 5, and 52 respectively. Tau-binding antibodies or binding fragments thereof comprising a VL with CDRL1, CDRL2, and CDRL3 of SEQ ID Nos.: 1, 2, 53 respectively and a VH with CDRH1, CDRH2, and CDRH3 of SEQ ID Nos: 4, 5, and 48 respectively, Tau-binding antibodies or binding fragments thereof comprising a VL with CDRL1, CDRL2, and CDRL3 of SEQ ID Nos.: 1, 2, 53 respectively and a VH with CDRH1, CDRH2, and CDRH3 of SEQ ID Nos: 4, 5, and 49 respectively, Tau-binding antibodies or binding fragments thereof comprising a VL with CDRL1, CDRL2, and CDRL3 of SEQ ID Nos.: 1, 2, 53 respectively and a VH with CDRH1, CDRH2, and CDRH3 of SEQ ID Nos: 4, 5, and 50 respectively, Tau-binding antibodies or binding fragments thereof comprising a VL with CDRL1, CDRL2, and CDRL3 of SEQ ID Nos.: 1, 2, 53 respectively and a VH with CDRH1, CDRH2, and CDRH3 of SEQ ID Nos: 4, 5, and 51 respectively, and Tau-binding antibodies or binding fragments thereof comprising a VL with CDRL1, CDRL2, and CDRL3 of SEQ ID Nos.: 1, 2, 53 respectively and a VH with CDRH1, CDRH2, and CDRH3 of SEQ ID Nos: 4, 5, and 52 respectively; Tau-binding antibodies or binding fragments thereof comprising a VL with CDRL1, CDRL2, and CDRL3 of SEQ ID Nos.: 1, 2, 54 respectively and a VH with CDRH1, CDRH2, and CDRH3 of SEQ ID Nos: 4, 5, and 48 respectively, Tau-binding antibodies or binding fragments thereof comprising a VL with CDRL1, CDRL2, and CDRL3 of SEQ ID Nos.: 1, 2, 54 respectively and a VH with CDRH1, CDRH2, and CDRH3 of SEQ ID Nos: 4, 5, and 49 respectively, Tau-binding antibodies or binding fragments thereof comprising a VL with CDRL1, CDRL2, and CDRL3 of SEQ ID Nos.: 1, 2, 54 respectively and a VH with CDRH1, CDRH2, and CDRH3 of SEQ ID Nos: 4, 5, and 50 respectively, Tau-binding antibodies or binding fragments thereof comprising a VL with CDRL1, CDRL2, and CDRL3 of SEQ ID Nos.: 1, 2, 54 respectively and a VH with CDRH1, CDRH2, and CDRH3 of SEQ ID Nos: 4, 5, and 51 respectively, and Tau-binding antibodies or binding fragments thereof comprising a VL with CDRL1, CDRL2, and CDRL3 of SEQ ID Nos.: 1, 2, 54 respectively and a VH with CDRH1, CDRH2, and CDRH3 of SEQ ID Nos: 4, 5, and 52 respectively.

Tau-binding antibodies or binding fragments thereof as contemplated by said first aspect may comprise these CDRs embedded in framework regions of different origin. Thus, the CDRs may be comprised within the original framework regions of AB1, namely the rabbit VL region of SEQ ID No.: 7 and the rabbit VH region of SEQ ID No.: 8. However, the CDRs may also be embedded in framework regions of different species origin such a mice or human framework regions. Depending on the origin of framework regions and constant regions, which can be combined with such framework regions, one may obtain chimeric, murinised, or humanized Tau-binding antibodies or binding fragments thereof.

Chimeric Tau-binding antibodies or binding fragments thereof will comprise the CDRs within framework regions of non-human origin combined with constant regions from a different species, such as of murine or of human origin. Murinised Tau-binding antibodies or binding fragments thereof will comprise the CDRs within framework regions of murine origin combined together with constant regions of murine origin. Humanized Tau-binding antibodies or binding fragments thereof will comprise the CDRs within framework regions of human origin combined together with constant regions of human origin.

Against this background the disclosure provides in another aspect an isolated Tau-binding antibody or binding fragment thereof, wherein said Tau-binding antibody or binding fragment thereof comprises a light chain variable region comprising SEQ ID No.: 7 or sequences at least 80% identical thereto, and/or a heavy chain variable region comprising SEQ ID No.: 8 or sequences at least 80% identical thereto.

The identity of VL and VH to SEQ ID Nos.: 7 and 8 respectively may be at least 80%, but may also be higher such as at least 80%, 85%, 90%, 95%, 96%, 97%, 98% or 99% with an optional preference for higher identities. Positions of different identity may be selected according to similarity considerations. It will be appreciated that in term of identity there may be more flexibility for the framework regions vs. the CDRs.

In this context the disclosure specifically considers Tau-binding antibodies or binding fragments thereof comprising a VL of SEQ ID No.: 7 and a VH of SEQ ID No.: 8.

Humanized Tau-binding antibodies or binding fragments thereof are particularly contemplated by the present disclosure.

To this end the CDRs may be grafted onto human framework regions. It will be appreciated that identification of such humanized CDR-grafted Tau-binding antibody or binding fragment thereof may be achieved following established approaches of the art. When the CDRs or specificity determining residues are grafted, any appropriate acceptor human variable region framework sequence may be used having regard to the class/type of the donor antibody from which the CDRs are derived (see, e.g.; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519, 596 A1).

Also, in a CDR-grafted antibody variable region of the present invention, the framework regions need not have exactly the same sequence as those of the acceptor antibody. CDRs may thus be grafted with or without framework changes. Introducing framework changes on the basis of a comparison between the framework regions of the donor variable regions and the acceptor framework regions may allow retaining e.g. the affinity of an antibody which otherwise may be reduced as a consequence of humanization. For instance, unusual residues may be changed to more frequently-occurring residues for that acceptor chain class or type. Alternatively, selected residues in the acceptor framework regions may be changed so that they correspond to the residue found at the same position in the donor antibody (see Riechmann et al., 1998, Nature, 332, 323-324). Such changes should be kept to the minimum necessary to recover the affinity of the donor antibody. Residues for change may be selected using the protocol outlined by Adair et al. (1991) (Humanised antibodies. WO91/09967). In a CDR-grafted antibody of the present invention, the acceptor heavy and light chains do not necessarily need to be derived from the same antibody and may, if desired, comprise composite chains having framework regions derived from different chains.

Examples of human acceptor frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at: http://vbase.rare-ce.cam.ac.uk/, or see Worldwide Website: imgt.org). The present disclosure specifically considers to use the human V-region IGKV1-39 plus JK4 J-region of SEQ ID No.: 44 (IMGT, see Worldwide Website: imgt.org/) as an acceptor framework region for the light chain CDRs and the human V-region IGHV4-39 plus JH4 J-region SEQ ID No.: 45 (IMGT, see Worldwide Website: imgt.org/) as an acceptor framework region for the heavy chain CDRs. In SEQ ID No.: 45, positions 1, 73 and 80 may e.g. be considered for residue changes in the framework regions. The glutamine residue in position 1 may be changed to glutamate. The valine residue in position 73 may be changed to lysine. The phenylalanine at position 80 may be changed to valine. Other positions in SEQ ID No.: 45 for residue changes in the framework regions may be positions 39 and/or 75. For example, the isoleucine residue in position 39 of SEQ ID No: 45 may be changed to valine. The threonine residue in position 75 may be changed to serine. Positions in SEQ ID No.: 44 for residue changes in the framework regions may be position 2 and/or 63. For example, the isoleucine residue in position 2 of SEQ ID No.: 44 may be changed to valine. The serine residue in position 63 of SEQ ID No.: 44 may be changed to lysine.

Against this background the disclosure provides in another aspect an isolated Tau-binding antibody or binding fragment thereof, wherein said Tau-binding antibody or binding fragment thereof comprises
a light chain variable region comprising SEQ ID No.: 9 or sequences at least 80% identical thereto, and/or
a heavy chain variable region comprising SEQ ID No.: 10 or sequences at least 80% identical thereto.

The disclosure further provides in another aspect an isolated Tau-binding antibody or binding fragment thereof, wherein said Tau-binding antibody or binding fragment thereof comprises
a light chain variable region comprising SEQ ID No.: 13 or sequences at least 80% identical thereto, and/or
a heavy chain variable region comprising SEQ ID No.: 16 or sequences at least 80% identical thereto.

Such an isolated Tau-binding antibody or binding fragment thereof may comprise
a light chain variable region comprising SEQ ID No.: 13 or sequences at least 80% identical thereto, and/or
a heavy chain variable region comprising SEQ ID No.: 14, 15, or sequences at least 80% identical thereto.

Furthermore such an isolated Tau-binding antibody or binding fragment thereof may comprise
a light chain variable region comprising SEQ ID No.: 11, 12 or sequences at least 80% identical thereto, and/or
a heavy chain variable region comprising SEQ ID No.: 16 or sequences at least 80% identical thereto.

Such an isolated Tau-binding antibody or binding fragment thereof may comprise
a light chain variable region comprising SEQ ID No.: 11 or sequences at least 80% identical thereto, and/or
a heavy chain variable region comprising SEQ ID No.: 14, 15 or sequences at least 80% identical thereto.

Such an isolated Tau-binding antibody or binding fragment thereof may comprise
a light chain variable region comprising SEQ ID No.: 12 or sequences at least 80% identical thereto, and/or
a heavy chain variable region comprising SEQ ID No.: 14, 15 or sequences at least 80% identical thereto.

The identity of VL and VH to SEQ ID Nos.: 13 and 16 respectively may be at least 80%, but may also be higher such as at least 80%, 85%, 90%, 95%, 96%, 97%, 98% or 99% with an optional preference for higher identities. Positions of different identity may be selected according to similarity considerations. It will be appreciated that in term of identity there may be more flexibility for the framework regions vs. the CDRs.

In this context the application specifically considers Tau-binding antibodies or binding fragments thereof comprising a VL of SEQ ID No.: 11 and a VH of SEQ ID No.: 14, Tau-binding antibodies or binding fragments thereof comprising a VL of SEQ ID No.: 11 and a VH of SEQ ID No.: 15, Tau-binding antibodies or binding fragments thereof comprising a VL of SEQ ID No.: 12 and a VH of SEQ ID No.: 14, and Tau-binding antibodies or binding fragments thereof comprising a VL of SEQ ID No.: 12 and a VH of SEQ ID No.: 15.

Humanized CDR grafted Tau-binding antibodies or binding fragments thereof may comprise constant regions of human origin. Depending on the amino acid sequence of the constant region of their heavy chains, antibodies or immunoglobulins are divided into the classes: IgA, IgD, IgE, IgG and IgM, and several of these may be further divided into subclasses (subtypes), e.g. IgG1, IgG2, IgG3, and IgG4, IgA1, and IgA2. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. The present disclosure specifically considers humanized antibodies of the IgG1 and IgG4 subtype.

It will be appreciated that sequence amendments of these constant region domains may also be used. For example one or more amino acid, such as 1 or 2 amino acid substitutions, additions and/or deletions may also be made to the antibody constant domains without significantly altering the ability of the antibody to bind to Tau. IgG4 molecules in which the serine at position 241 has been changed to proline as described in Angal et al., Molecular Immunology, 1993, 30 (I), 105-108 may be used as well.

Antibody effector functions include ADCC and CDC. ADCC refers to antibody-dependent cellular cytotoxicity. In order to determine whether an antibody is in principle capable of mediating ADDC, ADCC may be measured in vitro by e.g. so-called $Cr^{51}$, Eu, and $S^{35}$-release assays. A target cell containing the antigen of interest, i.e. Tau may be labeled with these compounds. After binding of the therapeutic antibody, the cells are washed and effector cells expressing Fc receptors such as FcγRIII are co incubated with the antibody-labeled target cells and lysis of the target cells can be monitored by release of the labels. Another approach uses the so-called aCella TOX™ assay. CDC refers to complement-dependent cellular cytotoxicity. In order to determine whether an antibody is in principle capable of mediating CDC, CDC may be measured in vitro as described e.g. in Delobel A et al, Methods Mol Biol. (2013); 988:115-43 or Current Protocols in Immunology, Chapter 13 Complement (Print ISSN: 1934-3671).

Against this background the disclosure provides in another aspect an isolated Tau-binding antibody or binding fragment thereof, wherein said Tau-binding antibody or binding fragment thereof comprises a light chain comprising SEQ ID No.: 19 or sequences at least 70% identical thereto, and/or a heavy chain comprising SEQ ID No.: 22 or sequences at least 70% identical thereto.

Such an isolated Tau-binding antibody or binding fragment thereof may comprise a light chain comprising SEQ ID No.: 19 or sequences at least 70% identical thereto, and/or a heavy chain comprising SEQ ID No.: 20, 21 or sequences at least 80% identical thereto.

Such an isolated Tau-binding antibody or binding fragment thereof may comprise a light chain comprising SEQ ID No.: 17, 18 or sequences at least 70% identical thereto, and/or a heavy chain comprising SEQ ID No.: 22 or sequences at least 80% identical thereto.

Such an isolated Tau-binding antibody or binding fragment thereof may comprise a light chain comprising SEQ ID No.: 17, 18 or sequences at least 70% identical thereto, and/or a heavy chain comprising SEQ ID No.: 20, 21 or sequences at least 80% identical thereto.

The identity of the light chain and heavy chain to SEQ ID Nos.: 19 and 22 respectively may be at least 70%, but may also be higher such as at least 70%, 75%, 80%, 85%, 90%, 95%, 96%, 97%, 98% or 99% with an optional preference for higher identities. Positions of different identity may be selected according to similarity considerations. It will be appreciated that in terms of identity there may be more flexibility for the framework regions vs. the CDRs and even more flexibility for the constant regions.

In this context the application specifically considers Tau-binding antibodies or binding fragments thereof comprising a light chain of SEQ ID No.: 17 and a heavy chain of SEQ ID No.: 20, Tau-binding antibodies or binding fragments thereof comprising a light chain of SEQ ID No.: 17 and a heavy chain of SEQ ID No.: 21, Tau-binding antibodies or binding fragments thereof comprising a light chain of SEQ ID No.: 18 and a heavy chain of SEQ ID No.: 20, and Tau-binding antibodies or binding fragments thereof comprising a light chain of SEQ ID No.: 18 and a heavy chain of SEQ ID No.: 21.

Furthermore, the disclosure provides in another aspect an isolated Tau-binding antibody or binding fragment thereof, wherein said Tau-binding antibody or binding fragment thereof comprises a light chain comprising SEQ ID No.: 19 or sequences at least 70% identical thereto, and/or a heavy chain comprising SEQ ID No.: 25 or sequences at least 70% identical thereto.

Such an isolated Tau-binding antibody or binding fragment thereof may comprise a light chain comprising SEQ ID No.: 19 or sequences at least 70% identical thereto, and/or a heavy chain comprising SEQ ID No.: 23 or SEQ ID No.: 24 or sequences at least 70% identical thereto.

Such an isolated Tau-binding antibody or binding fragment thereof may comprise a light chain comprising SEQ ID No.: 19 or sequences at least 70% identical thereto, and/or a heavy chain comprising SEQ ID No.: 23 or SEQ ID No.: 24 or sequences at least 80% identical thereto.

Such an isolated Tau-binding antibody or binding fragment thereof may comprise a light chain comprising SEQ ID No.: 17, 18 or sequences at least 70% identical thereto, and/or a heavy chain comprising SEQ ID No.: 23 or SEQ ID No.: 24 or sequences at least 80% identical thereto.

In this context the application specifically considers Tau-binding antibodies or binding fragments thereof comprising a light chain of SEQ ID No.: 17 and a heavy chain of SEQ ID No.: 23, Tau-binding antibodies or binding fragments thereof comprising a light chain of SEQ ID No.: 17 and a heavy chain of SEQ ID No.: 24, Tau-binding antibodies or binding fragments thereof comprising a light chain of SEQ ID No.: 18 and a heavy chain of SEQ ID No.: 23, and Tau-binding antibodies or binding fragments thereof comprising a light chain of SEQ ID No.: 18 and a heavy chain of SEQ ID No.: 24.

The identity of the light chain and heavy chain to SEQ ID No.: 19 and SEQ ID Nos.: 23 or 24, respectively may be at least 70%, but may also be higher such as at least 70%, 75%, 80%, 85%, 90%, 95%, 96%, 97%, 98% or 99% with an optional preference for higher identities. Positions of different identity may be selected according to similarity considerations. It will be appreciated that in terms of identity there may be more flexibility for the framework regions vs. the CDRs and even more flexibility for the constant regions.

Also provided by the present disclosure is a specific region or epitope of human Tau which is bound by an antibody or binding fragment thereof provided by the present disclosure, in particular an antibody or binding fragment thereof comprising any one of CDR-H1 (SEQ ID No.:4), CDR-H2 (SEQ ID No.:5), CDR-H3 (SEQ ID No.:6), CDR-L1 (SEQ ID No.:1), CDR-L2 (SEQ ID No.:2) or CDR-L3 (SEQ ID No.:3), for example antibodies comprising the VL of SEQ ID No.: 7 and the VL of SEQ ID No.: 8.

Further provided by the present disclosure is a specific region or epitope of human Tau, in particular a phosphorylated Tau region within amino acids 197-206 of SEQ ID NO.: 55, which is bound by an antibody or binding fragment thereof provided in the present disclosure, in particular an antibody or binding fragment thereof comprising the VL of SEQ ID No.: 7 and the VH of SEQ ID No.: 8.

The Tau region within amino acids 197 to 206 of SEQ ID No.: 55 comprises four possible phosphorylation sites corresponding to serine residues at positions 198 (S198), 199 (S199), 202 (S202) and a threonine residue at position 205 (T205).

The term "a phosphorylated Tau region within amino acids 197-206 of SEQ ID NO.: 55" refers to a Tau region within amino acids 197 to 206 of SEQ ID No.: 55 comprising at least one phosphorylated residue selected from S198, S199, S202 and T205. As a skilled artisan would know phosphorylated residues may also be referred to for example as Ser($PO_3H_2$) or Thr($PO_3H_2$).

Binding of a Tau-binding antibody to this specific region or epitope of Tau can be identified by any suitable epitope mapping method known in the art in combination with any one of the antibodies provided by the present disclosure. Examples of such methods include screening peptides of varying lengths derived from SEQ ID No.: 55 for binding to the Tau-binding antibodies or binding fragments thereof of the present disclosure with the smallest fragment that can specifically bind to the antibody containing the sequence of the epitope recognized by the Tau-binding antibodies or binding fragments thereof. Given the existence of different Tau isoforms in the central nervous system, it is to be understood that any such isoform may be used in the methods detailed herein. In a specific example the longest isoform of Tau may be used, i.e. isoform 2 as defined in SEQ ID No.: 55. The Tau peptides of SEQ ID No.: 55 may be produced recombinantly, synthetically or by proteolytic digestion of the Tau polypeptide. Peptides that bind the antibody can be identified by, for example, Western Blot or mass spectrometric analysis. In another example, NMR spectroscopy or X-ray crystallography can be used to identify the epitope bound by a Tau-binding antibody or binding fragment thereof. Once identified, the epitopic fragment which binds an antibody of the present invention can be used, if required, as an immunogen to obtain additional antibodies which bind the same epitope. Furthermore, the epitopic fragment which binds an antibody of the present invention can be used to obtain proteins that bind to the same epitope and, if required, inhibit at least aggregation of Tau, such as protein or polypeptide compounds comprising more than 10 amino acids that are based on protein scaffolds e.g. from lipocalin ("anticalins"), fibronectin ("adnectins", trinectins), kunitz domains, C-type lectin, transferrin, gamma-crystalline, cysteine-nots, ankyrin repeats ("DARPins") or protein A, ("affibodies") as known in the art (Tomlinson, 2004; Mosavi et al., 2004; Gill and Damle, 2006; Nilsson and Tolmachev, 2007; Binz et al., 2004). Additionally, molecules that bind the same epitope include further organic molecules including peptides and cyclic peptides comprising not more than 10 amino acids as well as peptidomimetics. Peptidomimetics are compounds that are based on the amino acid sequences found at protein-protein interaction sites and are known in the art (Sillerud and Larson, 2005).

Against this background the disclosure provides in another aspect an isolated Tau-binding antibody or binding fragment thereof, wherein said Tau-binding antibody or binding fragment thereof binds to a phosphorylated Tau region within amino acids 197 to 206 of SEQ ID No.: 55.

Such antibodies can be chimeric, murinised, humanized or fully human monoclonal antibodies or can be used to obtain chimeric, murinised, humanized or fully human monoclonal antibodies.

In another aspect the disclosure provides an isolated Tau-binding antibody or binding fragment thereof, wherein said Tau-binding antibody or binding fragment thereof binds to a phosphorylated Tau region within amino acids 197 to 206 of SEQ ID No.: 55, wherein said phosphorylated Tau region comprises at least at least one phosphorylated residue selected from S198, S199, 5202 and T205.

In another aspect the disclosure provides an isolated Tau-binding antibody or binding fragment thereof, wherein said Tau-binding antibody or binding fragment thereof binds to a phosphorylated Tau region within amino acids 197 to 206 of SEQ ID No.: 55, wherein said phosphorylated Tau region comprises at least one phosphorylated residue selected from S198, and S199.

In another aspect the disclosure provides an isolated Tau-binding antibody or binding fragment thereof, wherein said Tau-binding antibody or binding fragment thereof binds to a phosphorylated Tau region within amino acids 197 to 206 of SEQ ID No.: 55, wherein said phosphorylated Tau region comprises at least one phosphorylated residue selected from S202 and T205.

In another aspect the disclosure provides an isolated Tau-binding antibody or binding fragment thereof, wherein said Tau-binding antibody or binding fragment thereof binds to a phosphorylated Tau region within amino acids 197 to 206 of SEQ ID No.: 55, wherein said phosphorylated Tau region comprises at least one phosphorylated residue comprising S198.

In another aspect the disclosure provides an isolated Tau-binding antibody or binding fragment thereof, wherein said Tau-binding antibody or binding fragment thereof binds to a phosphorylated Tau region within amino acids 197 to 206 of SEQ ID No.: 55, wherein said phosphorylated Tau region comprises at least one phosphorylated residue comprising S199.

In another aspect the disclosure provides an isolated Tau-binding antibody or binding fragment thereof, wherein said Tau-binding antibody or binding fragment thereof binds to a phosphorylated Tau region within amino acids 197 to 206 of SEQ ID No.: 55, wherein said phosphorylated Tau region comprises at least one phosphorylated residue comprising S202.

In another aspect the disclosure provides an isolated Tau-binding antibody or binding fragment thereof, wherein said Tau-binding antibody or binding fragment thereof binds to a phosphorylated Tau region within amino acids 197 to 206 of SEQ ID No.: 55, wherein said phosphorylated Tau region comprises at least one phosphorylated residue comprising T205.

In another aspect the disclosure provides an isolated Tau-binding antibody or binding fragment thereof, wherein said Tau-binding antibody or binding fragment thereof binds to a phosphorylated Tau region within amino acids 197 to 206 of SEQ ID No.: 55, wherein said phosphorylated Tau region comprises at least two phosphorylated residues selected from S198, S199, S202 and T205.

In another aspect the disclosure provides an isolated Tau-binding antibody or binding fragment thereof, wherein said Tau-binding antibody or binding fragment thereof binds to a phosphorylated Tau region within amino acids 197 to 206 of SEQ ID No.: 55, wherein said phosphorylated Tau region comprises at least two phosphorylated residues comprising S198 and S199.

In another aspect the disclosure provides an isolated Tau-binding antibody or binding fragment thereof, wherein said Tau-binding antibody or binding fragment thereof binds to a phosphorylated Tau region within amino acids 197 to 206 of SEQ ID No.: 55, wherein said phosphorylated Tau region comprises at least two phosphorylated residues comprising S199 and S202.

In another aspect the disclosure provides an isolated Tau-binding antibody or binding fragment thereof, wherein said Tau-binding antibody or binding fragment thereof binds to a phosphorylated Tau region within amino acids 197 to 206 of SEQ ID No.: 55, wherein said phosphorylated Tau region comprises at least two phosphorylated residues comprising S202 and T205.

In another aspect the disclosure provides an isolated Tau-binding antibody or binding fragment thereof, wherein said Tau-binding antibody or binding fragment thereof binds to a phosphorylated Tau region within amino acids 197 to 206 of SEQ ID No.: 55, wherein said phosphorylated Tau region comprises at least two phosphorylated residues comprising S198 and T205.

In another aspect the disclosure provides an isolated Tau-binding antibody or binding fragment thereof, wherein said Tau-binding antibody or binding fragment thereof binds to a phosphorylated Tau region within amino acids 197 to 206 of SEQ ID No.: 55, wherein said phosphorylated Tau region comprises at least two phosphorylated residues comprising S198 and S202.

In another aspect the disclosure provides an isolated Tau-binding antibody or binding fragment thereof, wherein said Tau-binding antibody or binding fragment thereof binds to a phosphorylated Tau region within amino acids 197 to 206 of SEQ ID No.: 55, wherein said phosphorylated Tau region comprises at least two phosphorylated residues comprising S199 and T205.

In another aspect the disclosure provides an isolated Tau-binding antibody or binding fragment thereof, wherein said Tau-binding antibody or binding fragment thereof binds to a phosphorylated Tau region within amino acids 197 to 206 of SEQ ID No.: 55, wherein said phosphorylated Tau region comprises at least three phosphorylated residues selected from S198, S199, S202 and T205.

In another aspect the disclosure provides an isolated Tau-binding antibody or binding fragment thereof, wherein said Tau-binding antibody or binding fragment thereof binds to a phosphorylated Tau region within amino acids 197 to 206 of SEQ ID No.: 55, wherein said phosphorylated Tau region comprises at least three phosphorylated residues comprising S198 and S199.

In another aspect the disclosure provides an isolated Tau-binding antibody or binding fragment thereof, wherein said Tau-binding antibody or binding fragment thereof binds to a phosphorylated Tau region within amino acids 197 to 206 of SEQ ID No.: 55, wherein said phosphorylated Tau region comprises at least three phosphorylated residues comprising S199 and S202.

In another aspect the disclosure provides an isolated Tau-binding antibody or binding fragment thereof, wherein said Tau-binding antibody or binding fragment thereof binds to a phosphorylated Tau region within amino acids 197 to 206 of SEQ ID No.: 55, wherein said phosphorylated Tau region comprises at least three phosphorylated residues comprising S202 and T205.

In another aspect the disclosure provides an isolated Tau-binding antibody or binding fragment thereof, wherein said Tau-binding antibody or binding fragment thereof binds to a phosphorylated Tau region within amino acids 197 to 206 of SEQ ID No.: 55, wherein said phosphorylated Tau region comprises at least three phosphorylated residues comprising S198 and T205.

In another aspect the disclosure provides an isolated Tau-binding antibody or binding fragment thereof, wherein said Tau-binding antibody or binding fragment thereof binds to a phosphorylated Tau region within amino acids 197 to 206 of SEQ ID No.: 55, wherein said phosphorylated Tau region comprises at least three phosphorylated residues comprising S198 and S202.

In another aspect the disclosure provides an isolated Tau-binding antibody or binding fragment thereof, wherein said Tau-binding antibody or binding fragment thereof binds to a phosphorylated Tau region within amino acids 197 to 206 of SEQ ID No.: 55, wherein said phosphorylated Tau region comprises at least three phosphorylated residues comprising S199 and T205.

In another aspect the disclosure provides an isolated Tau-binding antibody or binding fragment thereof, wherein said Tau-binding antibody or binding fragment thereof binds to a phosphorylated Tau region within amino acids 197 to 206 of SEQ ID No.: 55, wherein said phosphorylated Tau region comprises the following four phosphorylated residues S198, S199, S202 and T205.

Such antibodies can be chimeric, murinised, humanized or fully human monoclonal antibodies or can be used to obtain chimeric, murinised, humanized or fully human monoclonal antibodies.

In another aspect the present disclosure provides an isolated neutralizing Tau-binding antibody or binding fragment thereof, wherein said neutralizing Tau-binding antibody or binding fragment thereof binds a phosphorylated Tau region within amino acids 197 to 206 of SEQ ID No.: 35.

Such antibodies can be chimeric, murinised, humanized or fully human monoclonal antibodies or can be used to obtain chimeric, murinised, humanized or fully human monoclonal antibodies.

In another aspect the present disclosure provides an isolated Tau-binding antibody or binding fragment thereof, wherein said Tau-binding antibody or binding fragment thereof binds to substantially the same epitope of Tau as a Tau-binding antibody or binding fragment thereof described above. Binding to the epitope may be determined as described for epitope mapping using e.g. a Tau-binding antibody or binding fragment thereof comprising a VL of SEQ ID No.: 7 and a VH of SEQ ID No.: 8 as reference.

Such antibodies can be chimeric, murinised humanized or fully human monoclonal antibodies or can be used to obtain chimeric, murinised, humanized or fully human monoclonal antibodies.

In another aspect the present disclosure provides an isolated Tau-binding antibody or binding fragment thereof, wherein said Tau-binding antibody or binding fragment thereof competes for binding to Tau with a Tau-binding antibody described above.

In this context the disclosure specifically contemplates an isolated Tau-binding antibody or binding fragment thereof, wherein said Tau-binding antibody or binding fragment thereof competes for binding to Tau with a Tau-binding antibody or binding fragment thereof comprising a VL of SEQ ID No.: 7 and a VH of SEQ ID No.: 8.

Such antibodies can be chimeric, murinised, humanized or fully human monoclonal antibodies or can be used to obtain chimeric, murinised humanized or fully human monoclonal antibodies.

Competition for binding to Tau can be determined by a reduction in binding of the antibody or binding fragment thereof to Tau by at least about 50%, or at least about 70%, or at least about 80%, or at least about 90%, or at least about 95%, or at least about 99% or about 100% in the presence of the reference antibody or binding fragment thereof which may comprise a VL of SEQ ID No.: 7 and a VH of SEQ ID No.: 8, or a VL of SEQ ID No.: 9 and a VH of SEQ ID No.: 10. Binding may be measured using surface Plasmon resonance using BIAcore® equipment, various fluorescence detection technologies (e.g. Fluorescence correlation spectroscopy, fluorescence cross-correlation, Fluorescence Lifetime measurements etc.) or various types of radioimmunoassays or other assays used to follow antibody binding to a target molecule.

The term "Tau-binding antibody or binding fragment thereof" means that the antibody or binding fragments thereof binds specifically to Tau by way of its variable regions, i.e. binds the Tau antigen with greater affinity than other antigens which are not homologues of Tau. The "Tau-binding antibody or binding fragment thereof" binds to Tau b way of its variable regions with at least twice, at least five times, at least 10, 20, 100, $10^3$, $10^4$, $10^5$ or at least $10^6$ times the affinity than other antigens which are not homologues of Tau. It will be understood that Tau-binding antibodies and binding fragments thereof may nevertheless also interact with other proteins (for example, *S. aureus* protein A or other antibodies in ELISA techniques) through interactions with sequences outside the variable region of the Tau-binding antibodies and binding fragments thereof. Such latter binding properties which are mediated by sequences outside the variable regions of the Tau-binding antibodies and binding fragments thereof and in particular by the constant regions of the Tau-binding antibodies and binding fragments thereof are not meant to be encompassed by the term "Tau-binding antibody or binding fragment thereof". Screening assays to determine binding specificity of an antibody are well known and routinely practiced in the art. Tau-binding antibodies or binding fragments thereof may have an equilibrium dissociation constant ($K_D$) for the affinity of the binding of the antibody (or the binding fragment thereof) to its antigen in the nanomolar range. Thus the $K_D$ may be below about $1*10^{-6}$, e.g. about below $5*10^{-7}$ such as about $2*10^{-7}$ or lower and can be measured using e.g. surface plasmon resonance and the BIAcore device as described in the examples.

As mentioned above, the present disclosure provides Tau-binding antibodies or binding fragments thereof. A full-length antibody includes a constant domain and a variable region. The constant region may not need to be present in its full length in an antigen binding fragment of an antibody. It is, however, to be understood that wherever the application considers the use of antibodies mediating ADCC and/or CDC, a binding fragment must comprise a constant region of sufficient length to be still capable of mediating ADCC and/or CDC.

As mentioned above, the present disclosure also refers to human Tau-binding antibodies or binding fragments thereof, which can be generated as an alternative to humanization. For example, transgenic animals (e.g., mice) are known in the art that are capable, upon immunization, of producing a full repertoire of human antibodies in the absence of production of endogenous murine antibodies. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies with specificity against a particular antigen upon immunization of the transgenic animal carrying the human germ-line immunoglobulin genes with said antigen. Technologies for producing such transgenic animals and technologies for isolating and producing the human antibodies from such transgenic animals are known in the art (Lonberg, 2005; Green, 1999; Kellermann and Green, 2002; Nicholson et al., 1999). Alternatively, in the transgenic animal; e.g. mouse, only the immunoglobulin genes coding for the variable regions of the mouse antibody are replaced with corresponding human variable immunoglobulin gene sequences. The mouse germline immunoglobulin genes coding for the antibody constant regions remain unchanged. In this way, the antibody effector functions in the immune system of the transgenic mouse and consequently the B cell development are essentially unchanged, which may lead to an improved antibody response upon antigenic challenge in vivo. Once the genes coding for a particular antibody of interest have been isolated from such transgenic animals the genes coding for the constant regions can be replaced with human constant region genes in order to obtain a fully human antibody. Other methods for obtaining human antibodies antibody fragments in vitro are based on display technologies such as phage display or ribosome display technology, wherein recombinant DNA libraries are used that are either generated at least in part artificially or from immunoglobulin variable (V) domain gene repertoires of donors. Phage and ribosome display technologies for generating human antibodies are well known in the art (Winter et al., 1994; Hoogenboom, 2002; Kretzschmar and von Ruden, 2002; Groves and Osbourn, 2005; Dufner et al., 2006).

Human antibodies may also be generated from isolated human B cells that are ex vivo immunized with an antigen of interest and subsequently fused to generate hybridomas which can then be screened for the optimal human antibody (Grasso et al., 2004; Li et al., 2006). The term "neutralizing Tau-binding antibody" as used herein refers to an antibody that binds to and inhibits at least one biological activity of Tau. In a particular embodiment a "neutralizing Tau-binding antibody" as used herein refers to an antibody that binds and inhibits Tau aggregation in an in vitro assay, such as for example in an in vitro assay such as described in experiment 3.1 below.

The term 'antibody' as used herein generally relates to intact (whole, full-length) antibodies i.e. comprising the elements of two heavy chains and two light chains. The antibody may comprise further additional binding domains, for example as per the molecule DVD-Ig as disclosed in WO 2007/024715, or the so-called (FabFv)2Fc described in WO2011/030107. Thus antibody as employed herein includes bi, tri or tetra-valent full length antibodies.

Binding fragments of antibodies include single chain antibodies (i.e. a full length heavy chain and light chain); Fab, modified Fab, Fab', modified Fab', F(ab')$_2$, Fv, Fab-Fv, Fab-dsFv, Fab-scFv, Fab-scFc, disulphide stabilized Fab-scFv, single domain antibodies (e.g. VH or VL or VHH), scFv, scFv-scFc, dsscFv, dsscFv-scFc, bi, tri or tetra-valent antibodies, Bis-scFv, diabodies, tribodies, triabodies, tetrabodies, domain antibodies(dAbs), such as sdAbs, VHH and VNAR fragments, and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). The Fab-Fv format was first disclosed in WO2009/040562 and the disulphide stabilised versions thereof, the Fab-dsFv was first disclosed in WO2010/035012. A disulphide stabilized form of Fab-scFv was described in WO2013/068571. Antibody formats comprising scFc formats were first described in WO2008/012543. Other antibody fragments for use in the present invention include the Fab and Fab' fragments described in International patent applications WO2005/003169, WO2005/003170 and WO2005/003171.

Multi-valent antibodies may comprise multiple specificities e.g. bispecific or may be monospecific (see for example WO92/22583 and WO05/113605). One such example of the latter is a Tri-Fab (or TFM) as described in WO92/22583.

In one embodiment there is provided a Fab fragment.

In one embodiment there is provided a Fab' fragment.

A typical Fab' molecule comprises a heavy and a light chain pair in which the heavy chain comprises a variable region VH, a constant domain CH1 and a natural or modified hinge region and the light chain comprises a variable region VL and a constant domain CL.

In one embodiment there is provided a dimer of a Fab' according to the present disclosure to create a F(ab')2 for example dimerisation may be through the hinge.

In one embodiment the antibody or binding fragment thereof comprises a binding domain. A binding domain will generally comprise 6 CDRs, three from a heavy chain and three from a light chain. In one embodiment the CDRs are in a framework and together form a variable region. Thus in one embodiment an antibody or binding fragment comprises a binding domain specific for antigen comprising a light chain variable region and a heavy chain variable region.

It will be appreciated that the affinity of Tau-binding antibodies or binding fragments thereof provided by the present disclosure may be altered using suitable methods known in the art. The present disclosure therefore also relates to variants of the antibody molecules of the present invention, which have an improved affinity for Tau. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

The Tau-binding antibodies and binding fragments thereof may thus also encompass any of the e.g. foregoing specifically mentioned amino acid sequences of the light or heavy chains with one or more conservative substitutions (e.g., 1, 2, 3, 4, 5, 6, 7, 8, 9, 10, 11, 12, 13, 14, or 15 conservative substitutions). One can determine the positions of an amino acid sequence that are candidates for conservative substitutions, and one can select synthetic and naturally-occurring amino acids that effect conservative substitutions for any particular amino acids. Consideration for selecting conservative substitutions include the context in which any particular amino acid substitution is made, the hydrophobicity or polarity of the side-chain, the general size of the side chain, and the pK value of side-chains with acidic or basic character under physiological conditions. For example, lysine, arginine, and histidine are often suitably substituted for each other. As is known in the art, this is because all three amino acids have basic side chains, whereas the pK value for the side-chains of lysine and arginine are much closer to each other (about 10 and 12) than to histidine (about 6). Similarly, glycine, alanine, valine, leucine, and isoleucine are often suitably substituted for each other, with the proviso that glycine is frequently not suitably substituted for the other members of the group. Other groups of amino acids frequently suitably substituted for each other include, but are not limited to, the group consisting of glutamic and aspartic acids; the group consisting of phenylalanine, tyrosine, and tryptophan; and the group consisting of serine, threonine, and, optionally, tyrosine.

The Tau-binding antibodies and binding fragments thereof as they are mentioned in the context of the present invention may encompass derivatives of the exemplary antibodies, fragments and sequences disclosed herein. "Derivatives" include Tau-binding antibodies and binding fragments thereof, which have been chemically modified. Examples of chemical modification include covalent attachment of one or more polymers, such as water soluble polymers, N-linked, or O-linked carbohydrates, sugars, phosphates, and/or other such molecules such as detectable labels such as fluorophores.

If desired a Tau-binding antibody or binding fragment thereof for use in the present invention may thus be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al, 1999, Pharmacology and Therapeutics, 83, 67-123). These techniques for conjugating effector molecules may include site specific conjugation or non-site specific or random conjugation. Particular chemical procedures include, for example, those described in WO 93/06231, WO 92/22583, WO 89/00195, WO 89/01476 and WO 03/031581. Alternatively, where the effector molecule is a protein or polypeptide the linkage may be achieved using recombinant DNA procedures, for example as described in WO 86/01533 and EP0392745. Alternatively, a particular attachment site for the effector molecule may be engineered into the antibody or antigen binding fragment thereof of the invention, for example as described in WO 2008/038024. Furthermore a coupling agent may be used to link the effector molecule to the antibody or antigen binding fragment thereof of the invention, for example as described in WO 2005/113605. It will be understood by the skilled artisan that the above recited possibilities may be used by themselves or in combination.

The term effector molecule as used herein includes, for example, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy. The effector molecule as used herein also includes therapeutic agents such as chemotherapeutic agents, therapeutic polypeptides, nanoparticles, liposomes or therapeutic nucleic acids.

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, *Pseudomonas* exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-I), interleukin-2 (IL-2), granulocyte macrophage colony stimulating factor (GM-CSF), granulocyte colony stimulating factor (G-CSF), nerve growth factor (NGF) or other growth factor and immunoglobulins, or other protein or polypeptide compounds comprising more than 10 amino acids that are based on protein scaffolds e.g. from lipocalin ("anticalins"), fibronectin ("adnectins", trinectins), kunitz domains, C-type lectin, transferrin, gamma-crystalline, cysteine-nots, ankyrin repeats ("DARPins"), Fyn SH3 domains ("fynomers") or protein A ("affibodies") as known in the art (Tomlinson, 2004; Mosavi et al., 2004; Gill and Damle, 2006; Nilsson and Tolmachev, 2007; Binz et al., 2004; Silacci et al. 2014).

Other effector molecules include peptides and proteins that enhance or facilitate blood-brain barrier penetration. For example, WO2010/043047, WO2010/063122, WO2010/063123 or WO2011/041897 describe peptide or polypeptides that may act as a vector capable of transporting a therapeutic molecule across the blood-brain barrier and method of conjugating them to a therapeutic molecule. Peptides and proteins of interest in the context of blood-brain barrier penetration include, but are not limited to, peptides and proteins that bind to a blood brain barrier receptor such as transferrin receptor, glucose receptor, insulin receptor, insulin-like growth factor receptor, low density lipoprotein receptor-related protein 8, low density lipoprotein receptor-related protein 1 and heparin-binding epidermal growth factor-like growth factor. Alternatively the effector molecule is an antibody fragment such as a domain antibody, camelid antibody or shark derived antibody (VNAR) that specifically binds to one of the above blood-brain barrier receptors.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals such as may be used in positron emission tomography or single-photon emission computed tomography, and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{124}$I, $^{125}$I, $^{131}$I, $^{111}$In, $^{99}$Tc, $^{89}$Zr, $^{90}$Y, $^{64}$Cu, $^{68}$Ga and $^{18}$F. A particular type of effector molecules suitable as detectable substances useful for diagnosis include electron-deficient tetrazines and trans-cyclooctene (TCO) as described in Wyffels et al. 2014, Nuclear Medicine and biology 41 (2014):513-523, where a Tau-binding antibody of the invention linked to tetrazine may be administered and allowed to reach maximum uptake and sufficient clearance from non target sites, followed by subsequent administration of TCO or an optimized TCO analog labeled with a suitable radioactive nuclide, such that the TCO will covalently bind the tetrazine on the Tau-binding antibody of the invention, and allow its detection for example by positron emission tomography or single-photon emission computed tomography.

In one embodiment there is provided a Tau-binding Fab, Fab', or scFv linked to a radioactive nuclide or to tetrazine. Linkages to a radioactive nuclide or to tetrazine may be made via attachment through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. No. 5,219,996; U.S. Pat. No. 5,667,425; WO98/25971, WO2008/038024). In one example the Tau-binding antibody or binding fragment thereof of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. In one embodiment if the radionuclide is a metal ion such as $^{111}$In, $^{99}$Tc, $^{89}$Zr, $^{90}$Y, $^{64}$Cu, or $^{68}$Ga this may be bound by a macrocycle chelator for example as described by Turner et al. (Br. J. Cancer, 1994, 70:35-41; *Comparative biodistribution of indium-111-labelled macrocycle chimeric B72.3 antibody conjugates in tumour-bearing mice*) whereby the latter is in turn covalently linked to the aforementioned amino acid side-chain or terminal amino acid functional group or groups of the antibody or antibody fragment. In a further embodiment the latter macrocycle chelate with bound radionuclide may be the effector molecule described in WO05/113605 which is part of a cross linker that links two or more anti-Tau antibodies or fragments thereof.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, and albumin binding proteins or albumin binding compounds such as those described in WO05/117984.

Where such an effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Specific naturally occurring polymers include lactose, amylose, dextran, glycogen or derivatives thereof.

In one embodiment the effector molecule is albumin or a fragment thereof, such as human serum albumin or a fragment thereof.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as the brain or extend circulating half-life (for review see Chapman, 2002, Advanced Drug Delivery Reviews, 54, 531-545). Thus, for example, where the product is intended to leave the circulation and penetrate tissue.

Suitable polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is a Tau-binding antibody or binding fragment thereof and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. No. 5,219,996; U.S. Pat. No. 5,667,425; WO98/25971, WO2008/038024). In one example the Tau-binding antibody or binding fragment thereof of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In another aspect, the present disclosure provides nucleic acid molecules comprising nucleic acid sequences encoding for Tau-binding antibodies and binding fragments thereof, to nucleic acid molecules comprising nucleic acid sequences encoding for the variable light and/or heavy chains thereof and to nucleic acid molecules comprising nucleic acid sequences encoding for the CDR1, CDR2 and/or CDR3 of the variable light and/or heavy chains thereof.

By way of example, the VL of AB1 (SEQ ID No.: 7) may be encoded by SEQ ID No.: 26). The VH of AB1 (SEQ ID No.: 8) may be encoded by SEQ ID No.: 27).

The humanized VL of SEQ ID No.: 11 may be encoded by SEQ ID No.: 30. The humanized VL of SEQ ID No.: 12 may be encoded by SEQ ID No.: 31. The humanized VH of SEQ ID No.: 14 may be encoded by SEQ ID No.: 32 and the humanized VH of SEQ ID No.: 15 may be encoded by SEQ ID No.: 33.

The humanized light chain of SEQ ID No.: 17 may be encoded by SEQ ID No.: 34 The humanized light chain of SEQ ID No.: 18 may be encoded by SEQ ID No.: 35 The humanized heavy chain of SEQ ID No.: 20 may be encoded by SEQ ID No.: 36 and the humanized heavy chain of SEQ ID No.: 21 may be encoded by SEQ ID No.: 37. The humanized heavy chain of SEQ ID No.: 23 may be encoded by SEQ ID No.: 38 and the humanized heavy chain of SEQ ID No.: 24 may be encoded by SEQ ID No.: 39.

The Tau-binding antibodies and binding fragments thereof may be encoded by a single nucleic acid (e.g., a single nucleic acid comprising nucleotide sequences that encode the light and heavy chain polypeptides of the antibody), or by two or more separate nucleic acids, each of which encode a different part of the antibody or antibody fragment. In this regard, the disclosure provides one or more nucleic acids that encode any of the forgoing antibodies, or binding fragments. The nucleic acid molecules may be DNA, cDNA, RNA and the like.

For example, DNA sequences coding for part or all of the antibody heavy and light chains may be synthesized as desired from the determined DNA sequences or on the basis of the corresponding amino acid sequences. DNA coding for acceptor framework sequences is widely available to those skilled in the art and can be readily synthesized on the basis of their known amino acid sequences.

Standard techniques of molecular biology may be used to prepare DNA sequences coding for the antibody molecule of the present invention. Desired DNA sequences may be synthesized completely or in part using oligonucleotide synthesis techniques. Site-directed mutagenesis and polymerase chain reaction (PCR) techniques may be used as appropriate.

Preferably, the encoding nucleic acid sequences are operatively linked to expression control sequences allowing expression in prokaryotic or eukaryotic cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript.

Additional regulatory elements may include transcriptional as well as translational enhancers, and/or naturally associated or heterologous promoter regions.

The present disclosure in a further aspect thus provides cloning or expression vectors comprising such nucleic acid sequences encoding for Tau-binding antibodies and binding fragments thereof.

A "vector" is any molecule or composition that has the ability to carry a nucleic acid sequence into a suitable host cell where e.g. synthesis of the encoded polypeptide can take place. Typically and preferably, a vector is a nucleic acid that has been engineered, using recombinant DNA techniques that are known in the art, to incorporate a desired nucleic acid sequence (e.g., a nucleic acid of the invention). Expression vectors typically contain one or more of the following components (if they are not already provided by the nucleic acid molecules): a promoter, one or more enhancer sequences, an origin of replication, a transcriptional termination sequence, a complete intron sequence containing a donor and acceptor splice site, a leader sequence for secretion, a ribosome binding site, a polyadenylation sequence, a polylinker region for inserting the nucleic acid encoding the polypeptide to be expressed, and a selectable marker element.

Vectors are typically selected to be functional in the host cell in which the vector will be used (the vector is compatible with the host cell machinery such that amplification of the gene and/or expression of the gene can occur).

The present disclosure in a further aspect thus provides host cells comprising cloning or expression vectors as described above and/or nucleic acid sequences encoding for Tau-binding antibodies and binding fragments thereof as described above.

The host cell can be any type of cell capable of being transformed with the nucleic acid or vector so as to produce a Tau-binding antibody or binding fragment thereof encoded thereby. The host cell comprising the nucleic acid or vector can be used to produce the Tau-binding antibody or binding fragment thereof, or a portion thereof (e.g., a heavy chain sequence, or a light chain sequence encoded by the nucleic acid or vector). After introducing the nucleic acid or vector into the cell, the cell is cultured under conditions suitable for expression of the encoded sequence. The antibody, antigen binding fragment, or portion of the antibody then can be isolated from the cell.

The host cells may be prokaryotic host cells (such as *E. coli*) or eukaryotic host cells (such as a yeast cell, an insect cell, or a vertebrate cell). The host cell, when cultured under appropriate conditions, expresses an antibody or binding fragment thereof which can subsequently be collected from the culture medium (if the host cell secretes it into the medium) or directly from the host cell producing it (if it is not secreted). Selection of an appropriate host cell will depend upon various factors, such as desired expression levels, polypeptide modifications that are desirable or necessary for activity, such as glycosylation or phosphorylation, and ease of folding into a biologically active molecule. Selection of the host cell will depend in part on whether the antibody or binding fragment thereof is to be post-transcriptionally modified (e.g., glycosylated and/or phosphorylated). If so, yeast, insect, or mammalian host cells are preferable.

Suitable mammalian host cells include CHO, myeloma or hybridoma cells. Suitable types of Chinese Hamster Ovary (CHO cells) for use in the present invention may include CHO and CHO-K1 cells including dhfr- CHO cells, such as CHO-DG44 cells and CHODXB11 cells and which may be used with a DHFR selectable marker or CHOKI-SV cells which may be used with a glutamine synthetase selectable marker. Many are available from the American Type Culture Collection (ATCC), Manassas, Va. Examples include mammalian cells, such as Chinese hamster ovary cells (CHO) (ATCC No. CCL61), human embryonic kidney (HEK) 293 or 293T cells (ATCC No. CRL1573), 3T3 cells (ATCC No. CCL92), or PER.C6 cells. Other cell types of use in expressing antibodies include lymphocytic cell lines, e.g. NSO myeloma cells and SP2 cells, COS cells.

Another aspect of the present disclosure provides a process for the production of a Tau-binding antibody or binding fragment thereof comprising culturing a host cell containing e.g. a vector under conditions suitable for leading to expression of a Tau-binding antibody or binding fragment thereof from e.g. DNA encoding the Tau-binding antibody or binding fragment thereof, and isolating the antibody molecule.

The Tau-binding antibody or binding fragment thereof may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The Tau-binding antibody or binding fragment thereof antibodies and fragments according to the present disclosure are expressed at good levels from host cells. Thus the properties of the antibodies and/or fragments are conducive to commercial processing.

Thus there is provided a process for culturing a host cell and expressing the Tau-binding antibody or binding fragment thereof, isolating the latter and optionally purifying the same to provide an isolated Tau-binding antibody or binding fragment thereof. In one embodiment the process further comprises the step of conjugating an effector molecule to the isolated antibody or fragment, for example conjugating to a PEG polymer in particular as described herein.

The Tau-binding antibody or binding fragment thereof can be formulated in compositions, especially pharmaceutical or diagnostic compositions. Pharmaceutical compositions comprise a therapeutically or prophylactically effective amount of a Tau-binding antibody or binding fragment thereof in admixture with a suitable carrier, e.g., a pharmaceutically acceptable agent. Diagnostic compositions comprise a diagnostically effective amount of a Tau-binding antibody or binding fragment thereof in admixture with a suitable carrier, e.g., a diagnostically acceptable agent.

Pharmaceutically acceptable agents for use in the present pharmaceutical compositions include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

The composition can be in liquid form or in a lyophilized or freeze-dried form and may include one or more lyoprotectants, excipients, surfactants, high molecular weight structural additives and/or bulking agents (see for example U.S. Pat. Nos. 6,685,940, 6,566,329, and 6,372,716).

Compositions can be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, or intralesional routes. A parenteral formulation typically will be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980, which is incorporated herein by reference.

Pharmaceutical compositions described herein can be formulated for controlled or sustained delivery in a manner that provides local concentration of the product (e.g., bolus, depot effect) and/or increased stability or half-life in a particular local environment. The compositions can include the formulation of antibodies, binding fragments, nucleic acids, or vectors of the invention with particulate preparations of polymeric compounds such as polylactic acid, polyglycolic acid, etc., as well as agents such as a biodegradable matrix, injectable microspheres, microcapsular particles, microcapsules, bioerodible particle beads, liposomes, and implantable delivery devices that provide for the controlled or sustained release of the active agent which can then be delivered as a depot injection.

Alternatively or additionally, the compositions can be administered locally via implantation into the affected area of a membrane, sponge, or other appropriate material on to which an antibody, binding fragment, nucleic acid, or vector of the invention has been absorbed or encapsulated. Where an implantation device is used, the device can be implanted into any suitable tissue or organ, and delivery of an antibody, binding fragment, nucleic acid, or vector of the invention can be directly through the device via bolus, or via continuous administration, or via catheter using continuous infusion.

A pharmaceutical composition comprising a Tau-binding antibody or binding fragment thereof can be formulated for inhalation, such as for example, as a dry powder. Inhalation solutions also can be formulated in a liquefied propellant for aerosol delivery. In yet another formulation, solutions may be nebulized.

One aspect of the present disclosure relates to the use of Tau-binding antibodies and binding fragments thereof as a therapeutically active agent in the treatment of diseases.

Another aspect of the present disclosure relates to the use of Tau-binding antibodies and binding fragments thereof in the treatment of tauopathies. Tauopathies which have been described to contain Tau inclusions (Clavaguera et al. Brain Pathology 23 (2013) 342-349) include Alzheimer disease (AD); Amyotrophic lateral sclerosis/parkinsonism-dementia complex; Argyrophilic grain disease; Chronic traumatic encephalopathy; Corticobasal degeneration; Diffuse neurofibrillary tangles with calcification; Down syndrome; Familial British dementia; Familial Danish dementia; Frontotemporal dementia and parkinsonism linked to chromosome 17 caused by MAPT mutations; Gerstmann-Sträussler-Scheinker disease; Guadeloupean parkinsonism; Myotonic dystrophy; Neurodegeneration with brain iron accumulation; Niemann-Pick disease, type C; Non-Guamanian motor neuron disease with neurofibrillary tangles; Pick disease; Postencephalitic parkinsonism; Prion protein cerebral amyloid angiopathy; Progressive subcortical gliosis; Progressive supranuclear palsy (PSP); SLC9A6-related mental retardation; Subacute sclerosing panencephalitis; Tangle-only dementia; and White matter tauopathy with globular glial inclusions.

Another aspect of the present disclosure thus relates to the use of Tau-binding antibodies and binding fragments thereof in the treatment of Alzheimer's disease and/or progressive supranuclear palsy.

Correspondingly, the present disclosure also relates to methods of treating tauopathies, in particular Alzheimer's disease and/or progressive supranuclear palsy, by administering a therapeutically active amount of a Tau-binding antibody or binding fragment thereof to a subject in need thereof.

The present disclosure also relates to the use of a Tau-binding antibody or binding fragment thereof in the manufacture of a medicament for the treatment of tauopathies, in particular Alzheimer's disease and/or progressive supranuclear palsy.

In another aspect of the present disclosure the Tau-binding antibody or binding fragment thereof may be used either alone or in combination with other agents in a therapy. For instance, the Tau-binding antibody or binding fragment thereof may be co-administered with at least one additional therapeutic agent. In certain aspects, an additional therapeutic agent is a therapeutic agent affective to treat the same or different disorder as the Tau-binding antibody or binding fragment thereof is being used to treat. Exemplary additional therapeutic agents include, but are not limited to: cholinesterase inhibitors (such as donepezil, galantamine, rovastigmine, and tacrine), NMDA receptor antagonists (such as memantine), amyloid beta peptide aggregation inhibitors, antioxidants, gamma-secretase modulators, nerve growth factor (NGF) mimics or NGF gene therapy, PPARγ agonists, HMS-CoA reductase inhibitors (statins), ampakines, calcium channel blockers, GABA receptor antagonists, glycogen synthase kinase inhibitors, intravenous immunoglobulin, muscarinic receptor agonists, nicotinic receptor modulators, active or passive amyloid beta peptide immunization, phosphodiesterase inhibitors, serotonin receptor antagonists and anti-amyloid beta peptide antibodies or further anti-tau antibodies. Additional exemplary neurological drugs may be selected from a growth hormone or neurotrophic factor; examples include but are not limited to brain-derived neurotrophic factor (BDNF), nerve growth factor (NGF), neurotrophin-4/5, fibroblast growth factor (FGF)-2 and other FGFs, neurotrophin (NT)-3, erythropoietin (EPO), hepatocyte growth factor (HGF), epidermal growth factor (EGF), transforming growth factor (TGF)-alha, TGF-beta, vascular endothelial growth factor (VEGF), interleukin-1 receptor antagonist (IL-lra), ciliary neurotrophic factor (CNTF), glial-derived neurotrophic factor (GDNF), neurturin, platelet-derived growth factor (PDGF), heregulin, neuregulin, artemin, persephin, interleukins, glial cell line derived neurotrophic factor (GFR), granulocyte-colony stimulating factor (CSF), granulocyte-macrophage-CSF, netrins, cardiotrophin-1, hedgehogs, leukemia inhibitory factor (LIF), midkine, pleiotrophin, bone morphogenetic proteins (BMPs), netrins, saposins, semaphorins, and stem cell factor (SCF). In certain embodiments, the at least one additional therapeutic agent is selected for its ability to mitigate one or more side effects of the neurological drug. Such combination therapies noted above encompass combined administration (where two or more therapeutic agents are included in the same or separate formulations), and separate administration, in which case, administration of the Tau-binding antibody or binding fragment thereof can occur prior to, simultaneously, and/or following, administration of the additional therapeutic agent and/or adjuvant. Tau-binding antibodies or binding fragments thereof can also be used in combination with other interventional therapies such as, but not limited to, radiation therapy, behavioral therapy, or other therapies known in the art and appropriate for the neurological disorder to be treated or prevented.

Another aspect of the present disclosure relates to the use of Tau-binding antibodies and binding fragments thereof as a diagnostically active agent.

One aspect of the present disclosure also relates to the use of Tau-binding antibodies and binding fragments thereof in the diagnosis of tauopathies, in particular of Alzheimer's disease and/or progressive supranuclear palsy.

Such diagnostic testing may preferably be performed on biological samples. A "biological sample" encompasses a variety of sample types obtained from an individual and can be used in a diagnostic or monitoring assay. The definition encompasses cerebrospinal fluid, blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, blood fractions such as plasma and serum, and the like.

Diagnostic testing may preferably be performed on biological samples which are not in contact with the human or animal body. Such diagnostic testing is also referred to as in vitro testing.

In vitro diagnostic testing may rely on an in vitro method of detecting Tau in a biological sample which has been obtained from an individual comprising the steps of i) contacting the biological sample with a Tau-binding antibody or binding fragment thereof as described herein; and ii) detecting binding of the Tau-binding antibody or binding fragment thereof as described herein to Tau. By comparing the detected Tau level with a suitable control, one can then diagnose the presence or likely occurrence of a tauopathy such as Alzheimer's disease and/or progressive supranuclear palsy. Such a detection method can thus be used to determine whether a subject has, or is at risk of developing, a tauopathy including determining the stage (severity) of a tauopathy.

The present disclosure thus provides an in vitro method of diagnosing a tauopathy such as Alzheimer's disease and/or progressive supranuclear palsy in a subject comprising the steps of i) assessing the level or state of Tau in a biological sample obtained from the subject by using a Tau-binding antibody or binding fragment thereof as described herein; and ii) comparing the level or state of Tau to a reference, a standard, or a normal control value that indicates the level or state of Tau in normal control subjects. A significant difference between the level and/or state of Tau polypeptide in the biological sample and the normal control value indicates that the individual has a tauopathy such as Alzheimer's disease and/or progressive supranuclear palsy.

With respect to these various aspects and embodiments which have been described herein, the present disclosure contemplates inter alia:

1. An isolated Tau-binding antibody or binding fragment thereof, wherein said Tau-binding antibody or binding fragment thereof comprises
a light chain variable region comprising a CDR1 selected from SEQ ID No.: 1 or sequences at least 90% identical thereto, a CDR2 selected from SEQ ID No.: 2 or sequences at least 90% identical thereto, and a CDR3 selected from SEQ ID No.: 3 or sequences at least 90% identical thereto; and/or
a heavy chain variable region comprising a CDR1 selected from SEQ ID No.: 4 or sequences at least 90% identical thereto, a CDR2 selected from SEQ ID No.: 5 or sequences at least 90% identical thereto, and/or a CDR3 selected from SEQ ID No.: 6 or sequences at least 0% identical thereto.

2. A Tau-binding antibody or binding fragment thereof of embodiment 1, wherein said Tau-binding antibody or binding fragment thereof comprises
a light chain variable region comprising a CDR1 selected from SEQ ID No.: 1, a CDR2 selected from SEQ ID No.: 2, and a CDR3 selected from SEQ ID No.: 3; and
a heavy chain variable region comprising a CDR1 selected from SEQ ID No.: 4, a CDR2 selected from SEQ ID No.: 5, and/or a CDR3 selected from SEQ ID No.: 6.

3. A Tau-binding antibody or binding fragment thereof of embodiment 1, or 2, wherein $X_1$ of SEQ ID No.: 3 is A.

4. A Tau-binding antibody or binding fragment thereof of embodiment 1, or 2, wherein $X_1$ of SEQ ID No.: 3 is G.

5. A Tau-binding antibody or binding fragment thereof of embodiment 1, or 2, wherein $X_2$ of SEQ ID No.: 6 is A.

6. A Tau-binding antibody or binding fragment thereof of embodiment 1, or 2, wherein $X_2$ of SEQ ID No.: 6 is Q.

7. A Tau-binding antibody or binding fragment thereof of embodiment 1, or 2, wherein $X_2$ of SEQ ID No.: 6 is N.

8. A Tau-binding antibody or binding fragment thereof of embodiment 1, or 2, wherein $X_2$ of SEQ ID No.: 6 is D.

9. A Tau-binding antibody or binding fragment thereof of embodiment 1, or 2, wherein $X_2$ of SEQ ID No.: 6 is S.

10. A Tau-binding antibody or binding fragment thereof of any of embodiments 1, 2, 3, 4, 5, 6, 7, 8 or 9, wherein said Tau-binding antibody or binding fragment thereof is a monoclonal antibody.

11. A Tau-binding antibody or binding fragment thereof of embodiment 10, wherein said Tau-binding antibody or binding fragment thereof is a chimeric, humanized or fully human antibody.

12. A Tau-binding antibody or binding fragment thereof of embodiment 11, wherein said Tau-binding antibody or binding fragment thereof is a humanized antibody of the IgG1 or IgG4 subtype.

13. A Tau-binding antibody or binding fragment thereof of any of embodiments 1, 2, 3, 4, 5, 6, 7, 8, 9, 10, 11 or 12, wherein said Tau-binding antibody or binding fragment thereof binds to a phosphorylated Tau region within amino acids 197-206 of SEQ ID No.: 55.

14. A Tau-binding antibody or binding fragment thereof of any of embodiments 1, 2, 3, 4, 5, 6, 7, 8, 9, 10, 11, 12 or 13, wherein said Tau-binding antibody or binding fragment binds to soluble forms of human Tau, paired helical filaments (PHF) of human Tau or to both soluble forms of human Tau and paired helical filaments (PHF) of human Tau.

15. An isolated Tau-binding antibody or binding fragment thereof, wherein said Tau-binding antibody or binding fragment thereof comprises
a light chain variable region comprising SEQ ID No.: 7 or sequences at least 80% identical thereto, and/or
a heavy chain variable region comprising SEQ ID No.: 8 or sequences at least 80% identical thereto.

16. A Tau-binding antibody or binding fragment thereof of embodiment 15, wherein said Tau-binding antibody or binding fragment thereof comprises
a light chain variable region comprising SEQ ID No.: 7, and
a heavy chain variable region comprising SEQ ID No.: 8.

17. A Tau-binding antibody or binding fragment thereof of embodiment 15, or 16, wherein $X_1$ of SEQ ID No.: 7 is A.

18. A Tau-binding antibody or binding fragment thereof of embodiment 15, or 16, wherein $X_1$ of SEQ ID No.: 7 is G.

19. A Tau-binding antibody or binding fragment thereof of embodiment 15, or 16, wherein $X_2$ of SEQ ID No.: 8 is A.

20. A Tau-binding antibody or binding fragment thereof of embodiment 15, or 16, wherein $X_2$ of SEQ ID No.: 8 is Q.

21. A Tau-binding antibody or binding fragment thereof of embodiment 15, or 16, wherein $X_2$ of SEQ ID No.: 8 is N.

22. A Tau-binding antibody or binding fragment thereof of embodiment 15, or 16, wherein $X_2$ of SEQ ID No.: 8 is D.

23. A Tau-binding antibody or binding fragment thereof of embodiment 15, or 16, wherein $X_2$ of SEQ ID No.: S.

24. A Tau-binding antibody or binding fragment thereof of any of embodiments 15, 16, 17, 18, 19, 20, 21, 22 or 23, wherein said Tau-binding antibody or binding fragment thereof is a monoclonal antibody.

25. A Tau-binding antibody or binding fragment thereof of embodiment 24, wherein said Tau-binding antibody or binding fragment thereof is a chimeric antibody.

26. A Tau-binding antibody or binding fragment thereof of any of embodiments 15, 16, 17, 18, 19, 20, 21, 22, 23, 24 or 25, wherein said Tau-binding antibody or binding fragment thereof binds to a phosphorylated Tau region within amino acids 197 to 206 of SEQ ID No.: 55.

27. A Tau-binding antibody or binding fragment thereof of any of embodiments 15, 16, 17, 18, 19, 20, 21, 22, 23, 24, 25 or 26, wherein said Tau-binding antibody or binding fragment binds to soluble forms of human Tau, paired helical filaments (PHF) of human tau or to both soluble forms of human Tau and paired helical filaments (PHF) of human tau.

28. An isolated Tau-binding antibody or binding fragment thereof, wherein said Tau-binding antibody or binding fragment thereof comprises
a light chain variable region comprising SEQ ID No.: 9 or sequences at least 80% identical thereto, and/or
a heavy chain variable region comprising SEQ ID No.: 10 or sequences at least 80% identical thereto.

29. An isolated Tau-binding antibody or binding fragment thereof, wherein said Tau-binding antibody or binding fragment thereof comprises
a light chain variable region comprising SEQ ID No.: 13 or sequences at least 80% identical thereto, and/or
a heavy chain variable region comprising SEQ ID No.: 16 or sequences at least 80% identical thereto.

30. A Tau-binding antibody or binding fragment thereof of embodiment 29, wherein said Tau-binding antibody or binding fragment thereof comprises
a light chain variable region comprising SEQ ID No.: 13, and
a heavy chain variable region comprising SEQ ID No.: 16.

31. A Tau-binding antibody or binding fragment thereof of embodiment 29, or 30, wherein $X_1$ of SEQ ID No.: 13 is A.

32. A Tau-binding antibody or binding fragment thereof of embodiment 29, or 30, wherein $X_1$ of SEQ ID No.: 13 is G.

33. A Tau-binding antibody or binding fragment thereof of embodiment 29, or 30, wherein $X_2$ of SEQ ID No.: 16 is A.

34. A Tau-binding antibody or binding fragment thereof of embodiment 29, or 30, wherein $X_2$ of SEQ ID No.: 16 is Q.

35. A Tau-binding antibody or binding fragment thereof of embodiment 29, or 30, wherein $X_2$ of SEQ ID No.: 16 is N.

36. A Tau-binding antibody or binding fragment thereof of embodiment 29, or 30, wherein $X_2$ of SEQ ID No.: 16 is D.

37. A Tau-binding antibody or binding fragment thereof of embodiment 29, or 30, wherein $X_2$ of SEQ ID No.: 16 is S.

38. A Tau-binding antibody or binding fragment thereof of embodiment 29, wherein the heavy chain variable region comprises SEQ ID No.: 14 or 15.

39. A Tau-binding antibody or binding fragment thereof of embodiment 29, wherein the light chain variable region comprises SEQ ID No.: 11 or 12.

40. A Tau-binding antibody or binding fragment thereof of any of embodiments 29, 30, 31, 32, 33, 34, 35, 36, 37, 38, or 39, wherein said Tau-binding antibody or binding fragment thereof is a monoclonal antibody.

41. A Tau-binding antibody or binding fragment thereof of embodiment 40, wherein said Tau-binding antibody or binding fragment thereof is a humanized antibody.

42. A Tau-binding antibody or binding fragment thereof of embodiment 41, wherein said Tau-binding antibody or binding fragment thereof is of the IgG1 or IgG4 subtype.

43. A Tau-binding antibody or binding fragment thereof of any of embodiments 29, 30, 31, 32, 33, 34, 35, 36, 37, 38, 39, 40, 41 or 42, wherein said Tau-binding antibody or binding fragment thereof binds to a phosphorylated Tau region within amino acids 197-206 of SEQ ID No.: 55.

44. A Tau-binding antibody or binding fragment thereof of any of embodiments 29, 30, 31, 32, 33, 34, 35, 36, 37, 38, 39, 40, 41, 42 or 43, wherein said Tau-binding antibody or binding fragment binds to soluble forms of human Tau, paired helical filaments (PHF) of human Tau or to both soluble forms of human Tau and paired helical filaments (PHF) of human Tau.

45. An isolated Tau-binding antibody or binding fragment thereof, wherein said Tau-binding antibody or binding fragment thereof comprises
a light chain comprising SEQ ID No.: 19 or sequences at least 70% identical thereto, and/or
a heavy chain comprising SEQ ID No.: 22 or sequences at least 70% identical thereto.

46. A Tau-binding antibody or binding fragment thereof of embodiment 45, wherein said Tau-binding antibody or binding fragment thereof comprises
a light chain comprising SEQ ID No.: 19, and
a heavy chain comprising SEQ ID No.: 22.
47. A Tau-binding antibody or binding fragment thereof of embodiment 45, or 46, wherein $X_1$ of SEQ ID No.: 19 is A.
48. A Tau-binding antibody or binding fragment thereof of embodiment 45, or 46, wherein $X_1$ of SEQ ID No.: 19 is G.
49. A Tau-binding antibody or binding fragment thereof of embodiment 45, or 46, wherein $X_2$ of SEQ ID No.: 22 is A.
50. A Tau-binding antibody or binding fragment thereof of embodiment 45, or 46, wherein $X_2$ of SEQ ID No.: 22 is Q.
51. A Tau-binding antibody or binding fragment thereof of embodiment 45, or 46, wherein $X_2$ of SEQ ID No.: 22 is N.
52. A Tau-binding antibody or binding fragment thereof of embodiment 45, or 46, wherein $X_2$ of SEQ ID No.: 22 is D.
53. A Tau-binding antibody or binding fragment thereof of embodiment 45, or 46, wherein $X_2$ of SEQ ID No.: 22 is S.
54. A Tau-binding antibody or binding fragment thereof of embodiment 45, wherein the heavy chain variable region comprises SEQ ID No.: 14 or 15.
55. A Tau-binding antibody or binding fragment thereof of embodiment 45, wherein the light chain variable region comprises SEQ ID No.: 11 or 12.
56. A Tau-binding antibody or binding fragment thereof of any of embodiments 45, 46, 47, 48, 49, 50, 51, 52, 53, 54 or 55, wherein said Tau-binding antibody or binding fragment thereof is a monoclonal humanized antibody.
57. A Tau-binding antibody or binding fragment thereof of embodiment 56, wherein said Tau-binding antibody or binding fragment thereof is of the IgG1 or IgG4 subtype.
58. A Tau-binding antibody or binding fragment thereof of any of embodiments 45, 46, 47, 48, 49, 50, 51, 52, 53, 54, 55, 56 or 57, wherein said Tau-binding antibody or binding fragment thereof binds to a phosphorylated Tau region comprising within amino acids 197-206 of SEQ ID No.: 55.
59. A Tau-binding antibody or binding fragment thereof of any of embodiments 45, 46, 47, 48, 49, 50, 51, 52, 53, 54, 55, 56, 57 or 58, wherein said Tau-binding antibody or binding fragment binds to soluble forms of human Tau, paired helical filaments (PHF) of human Tau or to both soluble forms of human Tau and paired helical filaments (PHF) of human Tau.
60. An isolated Tau-binding antibody or binding fragment thereof, wherein said Tau-binding antibody or binding fragment binds to a phosphorylated Tau region comprising within amino acids 197-206 of SEQ ID No.: 55.
61. A Tau-binding antibody or binding fragment thereof of embodiment 60, wherein said Tau-binding antibody or binding fragment thereof is a monoclonal antibody.
62. A Tau-binding antibody or binding fragment thereof of embodiment 60 or 61, wherein said Tau-binding antibody or binding fragment thereof is a chimeric, humanized or fully human antibody.
63. A Tau-binding antibody or binding fragment thereof of embodiment 62, wherein said Tau-binding antibody or binding fragment thereof is a monoclonal humanized antibody or binding fragment thereof of the IgG1 or IgG4 subtype.
64. A Tau-binding antibody or binding fragment thereof of any of embodiments 60, 61, 62, or 63, wherein said Tau-binding antibody or binding fragment binds to soluble forms of human Tau, paired helical filaments (PHF) of human Tau or to both soluble forms of human Tau and paired helical filaments (PHF) of human Tau.
65. An isolated Tau-binding antibody or binding fragment thereof, wherein said Tau-binding antibody or binding fragment thereof competes for binding to Tau with a Tau-binding antibody or binding fragment thereof of any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64.
66. A Tau-binding antibody or binding fragment thereof of embodiment 65, wherein said Tau-binding antibody or binding fragment thereof competes for binding to Tau with a Tau-binding antibody or binding fragment comprising
a light chain variable region comprising SEQ ID No.: 11 or 12, and
a heavy chain variable region comprising SEQ ID No.: 14 or 15.
67. An isolated Tau-binding antibody or binding fragment thereof, wherein said Tau-binding antibody or binding fragment thereof binds to substantially the same epitope of Tau as a Tau-binding antibody or binding fragment thereof of any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66 or 67.
68. A Tau-binding antibody or binding fragment thereof of embodiment 67, wherein said Tau-binding antibody or binding fragment thereof binds to substantially the same epitope of Tau as a Tau-binding antibody or binding fragment a Tau-binding antibody or binding fragment comprising
a light chain variable region comprising SEQ ID No.: 11 or 12, and
a heavy chain variable region comprising SEQ ID No.: 14 or 15.
69. An isolated Tau-binding antibody or binding fragment thereof of any of embodiments 65, 66, 67, or 68, wherein said Tau-binding antibody or binding fragment thereof is a monoclonal antibody.
70. A Tau-binding antibody or binding fragment thereof of embodiment 69, wherein said Tau-binding antibody or binding fragment thereof is a chimeric, humanized or fully human antibody.
71. A Tau-binding antibody or binding fragment thereof of embodiment 70, wherein said Tau-binding antibody or binding fragment thereof is a humanized antibody of the IgG1 or IgG4 subtype.
72. A Tau-binding antibody or binding fragment thereof of any of embodiments 65, 66, 67, 68, 69, 70, or 71, wherein said Tau-binding antibody or binding fragment thereof binds to a phosphorylated Tau region amino acids 197-206 of SEQ ID No.: 55.
73. A Tau-binding antibody or binding fragment thereof of any of embodiments 65, 66, 67, 68, 69, 70, 71, or 72, wherein said Tau-binding antibody or binding fragment binds to soluble forms of human Tau, paired helical filaments (PHF) of human Tau or to both soluble forms of human Tau and paired helical filaments (PHF) of human Tau.

74. An isolated Tau-binding antibody or binding fragment thereof of any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72 or 73 wherein said Tau-binding antibody or binding fragment thereof is a Fab, Fab', a F(ab')$_2$, a Fd and a Fv, a scFv, a Fab-Fv, Fab-scFv, Fab-dsFv, Fab-scFc, scFv-scFc, dsscFv, dsscFv-scFc, a diabody, a triabody, a tetrabody, a linear antibody, or a VHH containing antibody.

75. An isolated nucleic acid molecule encoding the light and/or heavy chain of a Tau-binding antibody or binding fragment thereof of any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, or 74.

76. A cloning or expression vector comprising one or more nucleic acid sequences of embodiment 75.

77. A host cell comprising one or more nucleic acid sequences of embodiment 75 or one or more cloning or expression vectors of embodiment 76.

78. A host cell of embodiment 77 which is not a human embryonic stem cell.

79. A method of producing a Tau-binding antibody or binding fragment thereof of any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63 64, 65, 66, 67, 68, 69, 70, 71, 72, 73 or 74 comprising at least the steps of
    a) culturing a host cell of embodiment 77 or 78, and
    b) isolating said Tau-binding antibody or binding fragment thereof.

80. An isolated Tau-binding antibody or binding fragment thereof of any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73 or 74 for use as a therapeutically active agent.

81. An isolated Tau-binding antibody or binding fragment thereof of any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73 or 74 for use in treating a tauopathy.

82. An isolated Tau-binding antibody or binding fragment thereof for use of embodiment 81, wherein said tauopathy is Alzheimer's disease.

83. An isolated Tau-binding antibody or binding fragment thereof for use of embodiment 81, wherein said tauopathy is progressive supranuclear palsy.

84. A method of treating a tauopathy comprising the step of administering a Tau-binding antibody or binding fragment thereof of any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73 or 74 to a subject in need thereof 85. A method of embodiment 84, wherein said tauopathy is Alzheimer's disease.

86. A method of embodiment 85, wherein said tauopathy is progressive supranuclear palsy.

87. An isolated Tau-binding antibody or binding fragment thereof of any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73 or 74 for use as a diagnostic agent.

88. An isolated Tau-binding antibody or binding fragment thereof of any of embodiments 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73 or 74 for use in diagnosing a tauopathy.

89. An isolated Tau-binding antibody or binding fragment thereof for use of embodiment 88, wherein said tauopathy is Alzheimer's disease.

90. An isolated Tau-binding antibody or binding fragment thereof for use of embodiment 88, wherein said tauopathy is progressive supranuclear palsy.

The invention is now described with respect to some examples which are however not be construed as limiting.

EXPERIMENTS

Experiment 1—Generation of Tau-Binding Antibodies 1.1 Tau Peptide Design and Production Peptides and immunogens were supplied by Peptide Protein Research Ltd., Bishop's Waltham, U.K., and were synthesized by Fmoc solid phase peptide chemistry according to the method of Atherton and Sheppard. (Ref: Atherton, E.; Sheppard, R. C. (1989). Solid Phase peptide synthesis: a practical approach. Oxford, England: IRL Press). Peptides containing phosphoserine (pSer), phosphothreonine (pThr), 3-nitrotyrosine (nTyr) and N-ε-acetyl lysine (aLys) were synthesised using the Fmoc-protected precursors Fmoc-Ser (PO(OBzl)OH)—OH, Fmoc-Thr(PO(OBzl)OH)—OH, Fmoc-Tyr(3-NO$_2$)—OH and Fmoc-Lys(Ac)—OH.

A peptide was designed and used to produce Tau-binding antibodies that would recognize all Tau isoforms that are post-translationally modified with phospho serine (pSer), phosphothreonine (pThr) and/or with nitroso-tyrosine (nTyr); it represents residues 197 to 206 as aligned to Tau isoform 2 (SEQ ID NO: 55, Uniprot code: P10636-8, NCBI ref: NP 005901.2):

```
N-acetyl-nTyr pSer pSer Pro Cys* pSer Pro Gly pThr
Pro-amide (peptide designated T197, and defined in
SEQ ID NO: 56).
```

N and C peptide termini were capped with acetyl and amide groups respectively and cys* signifies that the cysteine side chain thiol group is the point of conjugation for linkage to carrier protein or biotin for the preparation of immunogens or assay reagent respectively, as detailed below. The assay reagent for monitoring antisera titres was prepared by reacting equal masses of maleiimido-PEG-biotin and peptide. Three different immunogens were prepared by reaction of the peptide with the following carrier proteins that had been substituted with maleimide groups on ε-amino lysine side chains: keyhole limpet haemocyanin (KLH), bove serum albumin (BSA) and ovalbulmin (OVA).

1.2 Immunization 2 female New Zealand White rabbits (>2 kg) were immunised sub-cutaneously with 500 μg total peptide mix (T197 & T211) emulsified in an equal volume of complete Freund's adjuvant (CFA) by vigorously mixing with a syringe. Peptides were designed conjugated to KLH, OVA and BSA and were immunised alternately. Rabbits were given 2 booster injections at 21 day intervals using incomplete Freund's adjuvant (IFA) with bleeds taken, from the ear, 14 days post immunisation. Termination occurred 14 days after the final boost with single cell suspensions of spleen, bone marrow and peripheral blood mononuclear cells prepared and frozen in 10% DMSO/FCS at −80° C.

1.3 B Cell Culture

B cell cultures were prepared using a method similar to that described by Zubler et al. (1985). Briefly, PBMC-derived B cells from immunized rabbits were cultured at a density of approximately 3000 cells per well in bar-coded 96-well tissue culture plates with 200μ/well RPMI 1640 medium (Gibco BRL) supplemented with 10% FCS (PAA laboratories ltd), 2% HEPES (Sigma Aldrich), 1% L-Glutamine (Gibco BRL), 1% penicillin/streptomycin solution (Gibco BRL), 0.1% β-mercaptoethanol (Gibco BRL), 3% activated splenocyte culture supernatant and gamma-irradiated mutant EL4 murine thymoma cells ($5 \times 10^4$/well) for seven days at 37° C. in an atmosphere of 5% $CO_2$. In total, approximately $1.2 \times 10^7$ B cells were sampled.

1.4 Primary Screening

The presence of T197 peptide-specific antibodies in B cell culture supernatants was determined using a homogeneous fluorescence-based binding assay using Superavidin™ beads (Bangs Laboratories) coated with biotinylated T197 peptide as a source of target antigen. Screening involved the transfer of 10 ul of supernatant from barcoded 96-well tissue culture plates into barcoded 384-well black-walled assay plates containing T197 immobilised on beads (10 ul/well) using a Matrix Platemate liquid handler. Binding was revealed with a goat anti-rabbit IgG Fcγ-specific Cy-5 conjugate (Jackson). Plates were read on an Applied Biosystems 8200 cellular detection system.

1.5 Secondary Screening

Following primary screening, positive supernatants were consolidated on 96-well bar-coded master plates using an Aviso Onyx hit-picking robot and B cells in cell culture plates frozen at −800 C. Master plates were then screened in an ELISA assay on T197 peptide and also on streptavidin only. This was done in order to determine peptide specificity for each well, and to exclude false positive wells showing binding non-specifically to the Superavidin beads. The ELISA assay involved capture of biotinylated T197 onto 384-well Maxisorp plates (ThermoScientific/Nunc) coated with streptavidin in a carbonate coating buffer ($dH_2O$+ 0.16% $Na_2CO_3$+0.3% $NaHCO_3$). Plates were blocked with 1% w/v PEG/PBS and then incubated with 10 ul/well of B cell culture supernatant (diluted 1:1 with blocking buffer.) Secondary HRP-conjugated goat anti-rabbit IgG fc antibody (Stratech Scientific Ltd/Jackson ImmunoResearch) was added to plates, followed by visualization of binding with TMB substrate (3,3',5,5'-Tetramethylbenzidine, from EMD Millipore; 10 μl/well). The optical density was measured at 630 nM using BioTek Synergy 2 microplate reader. The primary binding assay identified 880 hits and following ELISA screening, 406 of those were shown to bind specifically to T197. B cell supernatants demonstrating specificity to the T197 were selected for further analysis by Biacore to identify those with the best affinity.

1.6 Variable Region Recovery

To allow recovery of antibody variable region genes from a selection of wells of interest, a deconvolution step had to be performed to enable identification of the antigen-specific B cells in a given well that contained a heterogeneous population of B cells. This was achieved using the Fluorescent foci method (Clargo et al., 2014). Briefly, Immunoglobulin-secreting B cells from a positive well were mixed with streptavidin beads (New England Biolabs) coated with biotinylated T197 peptide and a 1:1200 final dilution of a goat anti-rabbit Fcγ fragment-specific FITC conjugate (Jackson). After static incubation at 37° C. for 1 hour, antigen-specific B cells could be identified due to the presence of a fluorescent halo surrounding that B cell. A number of these individual B cell clones, identified using an Olympus microscope, were then picked with an Eppendorf micromanipulator and deposited into a PCR tube.

Antibody variable region genes were recovered from single cells by reverse transcription (RT)-PCR using heavy and light chain variable region-specific primers. Two rounds of PCR were performed on an Aviso Onyx liquid handling robot, with the nested 2° PCR incorporating restriction sites at the 3' and 5' ends allowing cloning of the variable region into a rabbit IgG (VH) or rabbit kappa (VL) mammalian expression vector. Anti-T197 antibody genes from 31 different wells were successfully cloned into expression vectors. Heavy and light chain constructs were co-transfected into HEK-293 cells using Fectin 293 (Invitrogen) and recombinant antibody expressed in 125 ml Erlenmeyer flask in a volume of 30 ml. After 5-7 days expression, supernatants were harvested and purified using affinity chromatography.

Experiment 2—Further Screening of Identified Antibodies 2.1 Tau Production in *E. coli*

Genes encoding the different Tau isoforms were generated synthetically and codon optimised for expression in *E. coli*. Standard molecular biology techniques were used to subclone into a modified pET32 vector engineered to produce Tau with an N-terminal 6His-TEV tag.

*E. coli* BL 21 (DE3) cells were transformed with the above vector, and the protein was expressed using standard techniques.

*E. coli* cells were then recovered by centrifugation, lysed and Tau protein captured from the soluble fraction by affinity chromatography using NiNTA (Qiagen). The 6His tag was removed using TEV protease followed by a second NiNTA chromatography step. Purified Tau was buffer exchanged into suitable buffers dependent on application. Samples generated for immunisations had endotoxin removed using Proteus NoEndo™ columns (Vivaproducts).

Generation of isotopically labelled Tau for nuclear magnetic resonance (NMR) studies: Protein expression was performed as described above except that minimal media was used for the incorporation of $^{15}N$, $^{13}C$ and $^2H$ into the protein. *E. coli* cell pellets were lysed and Tau protein was purified using a NiNTA (Qiagen) affinity chromatography step, the 6His tag was removed with TEV protease and Tau protein was then purified by Gel Filtration using a Superdex 200 unit (GE-Healthcare).

2.2 Tau Production in HEK293

A genes encoding Tau isoform 2 was generated synthetically using the wild-type DNA sequence. Standard molecular biology techniques were used to sub-clone it into expression vector pMV-10HisTEV (containing a CMV promotor) engineered to produce Tau with an N-terminal 10His-TEV tag.

The resulting vector was transfected using the Expi293™ Expression System (Invitrogen) following manufacturer's protocols. This system uses Expi293F human cells derived from the HEK293 cell line.

Tau protein accumulated in the culture media from where it was recovered using the immobilised metal ion affinity chromatography Ni Sepharose Excel (GE Healthcare). The 10His tag was then removed using TEV protease before reapplying to the Ni Sepharose column and collecting cleaved Tau in the flow through. Purified Tau was buffer exchanged into suitable buffers dependent on application.

2.3 Preparation of PHF Tau Fibrils from Human Brain Samples

Paired helical filament (PHF)-Tau protein was purified from brain samples from donors with Alzheimer's disease (AD) or progressive supranuclear palsy (PSP) or frontotemporal dementia (FTD) according to the protocol published by Ksiezak-Reding and Wall (Neurobiology of Aging 15, 11-19, 1994). Fractions 8 (equivalent to crude PHF-Tau before sucrose gradient centrifugation in this reference) and 11 (equivalent to fraction A2, SDS soluble PHF as described in this reference) which have been previously described to be enriched in PHF-Tau were recovered and used for the BIAcore assay and the cellular assay of Experiment 3.

2.4 ELISA Screening

Purified antibody was then subject to further screening by ELISA and by Biacore to confirm activity of the recombinant antibody and to select the highest affinity and most specific antibody. The ELISA assay again involved capture of biotinylated T197 onto 384-well Maxisorp plates (ThermoScientific/Nunc) coated with streptavidin in carbonate coating buffer (dH2O+0.16% Na2CO3+0.3% NaHCO$_3$). Separate plates were also coated with different Tau peptides mapping to alternative regions of the Tau molecule to check for specificity of binding only to the T197 sequence. Plates were blocked with 1% w/v PEG/PBS and then incubated with several dilutions of purified transient supernatant. Secondary HRP-conjugated goat anti-rabbit IgG fc antibody (Stratech Scientific Ltd/Jackson ImmunoResearch) was added to plates, followed by visualisation of binding with TMB substrate (3,3',5,5'-Tetramethylbenzidine, from EMD Millipore; 10 μl/well). The optical density was measured at 630 nM using BioTek Synergy 2 microplate reader. Data for the selected antibody, AB1 with rabbit VL of SEQ ID No.: 7 and rabbit VH of SEQ ID No.: 8, is shown in FIG. 1. As can be seen AB1 shows highly selective binding to only T197 and not to four peptides corresponding to other regions of the Tau molecule:

```
T174
                                    (SEQ ID No.: 62)
N-acetyl-C*K pT PPAPK pT P P amide;

T211
                                    (SEQ ID No.: 63)
N-acetyl-R pT P pS L P pT P C* amide;

T230
                                    (SEQ ID No.: 57)
N-acetyl-R pT P P K pS P pS SC* amide;
and T396
                                    (SEQ ID No.: 64)
N-acetyl-C*pS P V V pS G D pT pS amide;
```

*position of biotin conjugation.

2.5 BIAcore Screening

Selected rabbit anti-Tau IgG antibody clones were transiently expressed, purified and analysed using the SPR Biacore T200 platform. The antibodies were first captured onto a CM5 sensor chip using immobilized goat F(ab')2 anti-rabbit Fc gamma reagent. Flow cells 2, 3 and 4 showed immobilization levels between 5600-6100 RU while blocked flow cell 1 (dextran only) served as a reference. The purified IgGs were diluted to 0.5 μg/ml in HBS-EP+ buffer from GE Healthcare and captured on the chip with a flow rate of 10 μl/min. Each capture step was followed by 180 s analyte injections with a peptide/streptavidin complex, buffer controls and the dephosphorylated peptide/streptavidin complex. Peptides were dephosphorylated by using 10 μl of a 10004 peptide solution in HBS-EP+ containing 3 mM EDTA and 1% DMSO, diluting it 1:10 in HBS-N buffer (GE Healthcare) containing 0.3 mM EDTA and saturating the EDTA with 2 μl of 0.5M MgCl2. 2 μl of a 1:10 dilution (in HBS-N) of Calf Intestinal Alkaline Phosphatase (NEB, Cat# M0290S) was added and incubated at 37° C. for one hour, then stored at 4° C. The phosphatase reaction was inhibited by adding 1 μl of 0.5M EDTA to the mixture. The solution was used for the preparation of the dephosphorylated peptide/streptavidin complex. For the rabbit antibody with a VL region of SEQ ID No.: 7 and VH of SEQ ID No.: 8, the peptide T230 from the Tau region 230-238 with the amino acid sequence of SEQ ID No.: 57 was used as a negative control. Data were fitted with a bivalent analyte model.

Table 1 shows affinity values measured for this antibody when bound to the T197 and T230 phosphorylated and dephosphorylated peptide/streptavidin complexes.

TABLE 1

| Tau peptide | Binding (RU) | Ka (1/Ms) | Kd (1/s) | KD (nM) |
|---|---|---|---|---|
| T197 | 61 | 9.2E+05 | 2.6E−03 | 3 |
| T197 dephos. | 1 | No significant binding | | |
| T230 | 0 | No significant binding | | |
| T230 dephos. | 0 | No significant binding | | |

Selected monoclonal Fab fragments (mFab) were prepared from murinised mAB1 antibody with light chain of SEQ ID No.: 58 and heavy chain of SEQ ID No.: 59 using the Pierce Ficin cleavage kit (Cat. No. 44980, Thermo Scientific) according to the protocol of the manufacturer. Absorption at 280 nm was used to determine the concentration of the Fab stock solutions for the Biacore analysis. An insoluble Tau protein preparation from Alzheimer's disease patients (AD-PHF, fraction 11), the HEK-derived Tau isoform-2 monomers (amino acids 1-441), and the isoform-2 monomers expressed in E. coli were amine immobilized onto the CM5 chip, and binding of anti-Tau mFabs was measured with the Biacore T200 instrument. The buffer HBS-EP from GE Healthcare was used for immobilizations apart from the AD-PHF for which 10 mM acetic acid (pH3.0) was used. The HBS-EP+ buffer was supplemented with 300 mM NaCl and 1.25% CM-Dextran (Sigma) and used as the assay buffer. While flow cell (Fc) 1 was used as a reference, the following RU values were obtained for Fc2-4: 44 RU with 5 ug/ml E. coli Tau, 56 RU with 5 ug/m HEK Tau, and 500 RU with a 1:20 diluted solution of the AD-PHF material. Two 60 s cycles of 10 mM Glycine (pH1.7) were used for regeneration. Flow rates of 10 ul/min were used for immobilization and regeneration while a 30 ul/min flow rate was used for analyte binding. For AD-PHF, multiple manual injections were applied to reach 500 RU, including EDC/NHS and EtoA capping. Five start-up cycles and 12 cycles per mFab sample or buffer control were applied, using 90 uls analyte injections for either 180 s or 300 s for dissociation. 11 1:3 dilutions of a 600 nM solution plus buffer were used for each mFab.

regenerated at the end of each cycle by two 20 µl injections of 1.5 M guanidine in phosphate buffered saline.

TABLE 3

| | Peptide | | | | | | | | | | % inhibition | |
|---|---|---|---|---|---|---|---|---|---|---|---|---|
| | Tau sequence | | | | | | | | | | | |
| ID | 197 | 198 | 199 | 200 | 201 | 202 | 203 | 204 | 205 | 206 | HEK iso-2 | PHF |
| T197  | nY | pS | pS | P | G | pS | P | G | pT | P | 54 | 100 |
| T197B | Y  | S  | S  | P | G | S  | P | G | T  | P | n.s. | n.s. |
| T197C | Y  | pS | pS | P | G | pS | P | G | pT | P | 49 | 101 |
| T197E | nY | pS | S  | P | G | pS | P | G | pT | P | 52 | 102 |
| T197F | nY | pS | pS | P | G | S  | P | G | pT | P | 30 | 36 |
| T197G | nY | pS | pS | P | G | pS | P | G | T  | P | n.s. | n.s. |
| T197H | nY | pS | pS | P | G |    |   |   |    |   | n.s. | n.s. |
| T197I |    |    |    |   | G | pS | P | G | pT | P | 55 | 101 |

Key: nY is nitro tyrosine, pS is phospho-serine; pT is phospho-threonine; n.s. not significant at 95% confidence level.

TABLE 2

Binding of mFab from mAB1 and control antibody 101.4 to monomeric Tau isoform-2 expressed in E. coli, mammalian HEK293 cells and isolated Tau PHF fibrils from Alzheimer's disease patients.

| Sample | | Rmax (RU) | ka (1/Ms) | kd (1/s) | KD (M)* |
|---|---|---|---|---|---|
| 101.4 (isotype control) | E. coli iso-2 | | No significant binding | | |
| | HEK iso-2 | | No significant binding | | |
| | AD-PHF | | No significant binding | | |
| mAB1 | E. coli iso-2 | | No significant binding | | |
| | HEK iso-2 | | No significant binding | | |
| | AD-PHF | 5 | 7.96E+04 | 4.70E−02 | 5.90E−07 |

2.6 Epitope Mapping by BIAcore

Recombinant Tau isoform-2 monomer (amino acids 1-441), expressed and purified from HEK cells, and insoluble Tau protein in the form of a paired helical filament preparation isolated from Alzheimer's disease patient brain (AD-PHF), were amine immobilized onto the CM5 chip using a Biacore 3000 instrument and HBS-EP (GE Healthcare) as running buffer. The former were amine coupled to flow cells 2 and 4 respectively following activation of the carboxymethyl dextran surface these and reference flow cells by injection of 70 µl of a fresh mixture of 50 mM N-hydroxysuccimide and 200 mM 1-ethyl-3-(3-dimethyl-aminopropyl)-carbodiimide at a flow rate of 10 µl/min. Immobilization of tau monomer was achieved by injecting 160 µl at 50 µg/ml in 10 mM acetate pH 5.0 buffer, whereas AD-PHF was immobilized by injecting twenty 160 µl aliquots at 2 µg/ml in 10 mM acetic acid (pH3.0). Test and control flow cell surfaces were deactivated with a 50 µl pulse of 1 M ethanolamine. HCl pH 8.5.

Epitope mapping was carried out by pre-incubating solutions of a Tau-binding humanised antibody having the light chain of SEQ ID NO: 17 and the heavy chain of SEQ ID NO: 20 (L17H20) and test peptide or buffer controls, prepared in running buffer at 200 nM and 5000 nM respectively. These were tested separately in a series of sensorgram cycles at a constant flow rate of 10 µl/min by injecting 50 µl, over reference, tau monomer and AD-PHF flow cells. Response units of antibody binding were recorded at report points taken 15 sec after the end of each injection as the difference between values of test and reference flow cells. The chip was Antibody reactivity to a given test peptide was evident by the level of percentage inhibition of antibody binding to either immobilized tau monomer or to AD-PHF relative to that of the average antibody binding value calculated for control cycles.

Test peptides were prepared and analysed based on the peptide containing residues 196 to 206 of Tau protein (SEQ ID NO: 65), and the role of postranslation modification with phosphor serine, phosphor threonine and/or nitroso tyrosine was analyzed as defined in table 3.

Based on this analysis it is concluded that the minimal epitope is the phosphorylated Tau region defined by amino acids 201 to 206 of SEQ ID NO: 55, (corresponding to the motif Gly pSer Pro Gly pThr Pro), and that this epitope has an absolute requirement for the presence of phosphor-Threonine at position 205 of SEQ ID NO: 55, and phospho-Serine at position 202 of SEQ ID NO: 55.

Experiment 3—Further Characterization of Identified Antibodies 3.1 Cellular Assay
Preparation of Crude Soluble and Insoluble Fractions from Tau Transgenic Mice to Induce Tau Aggregation For these experiments transgenic mice expressing human Tau P301S (Allen et al., 2002 J. Neurosci. 22(21):9340-51, and P301L (Lewis et al., 2000 Nat Genet. (4):402-5.; Gotz J, et al., 2001 J Biol Chem. 276(1):529-34) were used.

Crude soluble and insoluble fractions were prepared from the brain of P301S and P301L Tau transgenic mice by differential centrifugation. Briefly, brain tissues from P301S (spinal cord and brainstem) and P301L (midbrain and brainstem) Tau transgenic mice were homogenized in ice-cold TBS (Fisher Scientific) using the hand-held homogenizer Pellet Pestle Motor (Kontes) in 1.5 ml microcentrifuge tubes on ice. Then, homogenates (H) were centrifuged at 4,000 g for 10 min at 4° C. to remove tissue debris. Resulting supernatants (S0) were centrifuged at 20,000 g for 20 min at 4° C. to provide supernatants corresponding to the crude soluble fraction (51). The remaining pellets (P1) were resuspended in 1 ml of 1% sarkosyl solution prepared in TBS, incubated for 1 h at room temperature, and then centrifuged at 100,000 g for 1 h at 4° C. The supernatants (S2) were discarded. The pellets (P2) were washed with 5 ml ice-cold TBS, and then resuspended in TBS to provide the crude insoluble fraction (P2').

Preparation of HEK-293-F Cells Expressing Human Tau with P301S Mutation

HEK-293-F cells (Life Technologies) were transfected with the pcDNA3.1(+) vector expressing human Tau isoform 2 with a P301S mutation, using 293fectin (Life Technologies) according to manufacturer's instructions. Aliquots of transfected cells were stored in liquid nitrogen.

Induction of Tau Aggregation

FIG. 2 illustrates the different steps of the cellular aggregation assay used to characterize the activity of Tau therapeutic antibodies. On day 1, HEK-293-F cells expressing human Tau isoform 2 with P301S mutation (P301S-tau) were defrosted at 37° C. and diluted in 293 Expression medium (Life Technologies) containing 10% fetal bovine serum and 1% Penicillin-Streptomycin (FFBS). Cells were counted using an automatic cell counter (Vi-CELL XR, Beckman Coulter), and then plated in poly-D-lysine pre-coated 96-well plates (Greiner Bio-One) at a density of 25,000 live cells per well. Cells were maintained at 37° C. in 5% $CO_2$. The same day, sonicated human insoluble Tau from patients with Alzheimer's disease (AD-PHF, fraction 8) or progressive supranuclear palsy (PSP-PHF, fraction 8) or frontotemporal dementia (FTD-PHF) or brain fractions from P301S or P301L transgenic mice brains, (used as seeds to induce Tau aggregation), were incubated with or without anti-Tau antibodies in FFBS medium at 4° C. with gentle agitation overnight. AD-PHF, fraction 8 was used at 80 ng/µl and 60 ng/µl for AD and PSP samples, respectively; soluble brain fraction from transgenic mice P301S and P301L were used at 0.1 µg/µl t 1.2 µg/µl, respectively. On day 2, seeds or seed/antibody mixtures were applied to cells for 24 h. On day 3, the culture medium was replaced with fresh FFBS medium containing antibody, and cells were maintained in culture for an additional 24 h. On day 4, Tau aggregation was measured using a Tau aggregation assay kit (Cisbio) based on homogenous time-resolved fluorescence energy transfer (HTRF), according to manufacturer's instructions. Fluorescence was measured with SpectraMax Paradigm (Molecular Devices). Aggregation was reported as percent aggregation relative to control (−) which corresponds to the maximal aggregation response induced by exogenous fibrils or fractions in the absence of the antibody.

The effect of AB1 and other Tau-binding antibodies of the prior art on induced Tau aggregation were tested. The prior art antibodies were IPN002 of WO2014/028777A2, PT3 of WO2013/096380A2, mAb2.10.3 of WO2010/142423A2, and HJ8.5 of WO 2014/008404.

The results of this assay are summarized in Table 3 and FIG. 3.

Table 4 summarizes the potency ($IC_{50}$) and maximal efficacy ($I_{max}$ at 300 nM) of AB1 having a murinised VL of SEQ ID NO: 9 and a murinised VH of SEQ ID NO.: 10 (VL9VH10), of a Tau-binding antibody having the light chain of SEQ ID No.: 17 and the heavy chain of SEQ ID No.:23 (L17H23), a Tau-binding antibody having a the light chain of SEQ ID No.: 17 and the heavy chain of SEQ ID No.:24 (L17H24), a Tau-binding antibody having a the light chain of SEQ ID No.: 17 and the heavy chain of SEQ ID No.:20 (L17H20), a Tau-binding antibody having the light chain of SEQ ID No.: 17 and the heavy chain of SEQ ID No.:21 (L17H21), and competitor antibodies against a range of Tau seed from various brain extracts. Whereas FIG. 3 shows the efficacy of a Tau-binding antibody having the light chain of SEQ ID No.: 17 and the heavy chain of SEQ ID No.:20 (L17H20), and of a Tau-binding antibody having a the light chain of SEQ ID No.: 17 and the heavy chain of SEQ ID No.:21 (L17H21) in a cellular aggregation assay using human Tau pathological fibrils from human PSP patients.

TABLE 4

| | Experiment 3.1 | | | | |
|---|---|---|---|---|---|
| mAB | Tg mice (P301S) $IC_{50}/I_{max}$ | Tg mice (P301L) $IC_{50}/I_{max}$ | Human AD samples $IC_{50}/I_{max}$ | Human PSP samples | Human FTD samples |
| VL9VH10 | $IC_{50}$: 8 nM $I_{max}$: 62% | $IC_{50}$: 9 nM $I_{max}$: 81% | $IC_{50}$: 10 nM $I_{max}$: 79% | $IC_{50}$: ND $I_{max}$: 54% | $IC_{50}$: 1 nM $I_{max}$: 81% |
| L17H23 IgG1 | Not tested | Not tested | Not tested | $IC_{50}$: ND $I_{max}$: 49% | Not tested |
| L17H24 IgG1 | Not tested | Not tested | Not tested | $IC_{50}$: ND $I_{max}$: 47% | Not tested |
| L17H20 IgG4 | Not tested | Not tested | $IC_{50}$: 2 nM $I_{max}$: 85% | $IC_{50}$: 42 nM $I_{max}$: 65% | $IC_{50}$: 1 nM $I_{max}$: 79% |
| L17H21 IgG4 | Not tested | Not tested | Not tested | $IC_{50}$: 66 nM $I_{max}$: 47% | Not tested |
| IPN002 | $IC_{50}$: ND $I_{max}$: 22% | $IC_{50}$: 122 nM $I_{max}$: 73% | $IC_{50}$: ND $I_{max}$: 19% | $IC_{50}$: 207 nM $I_{max}$: 64% | $IC_{50}$: ND $I_{max}$: 50% |
| PT3 | $IC_{50}$: 350 nM $I_{max}$: 56% | $IC_{50}$: 26 nM $I_{max}$: 69% | $IC_{50}$: 32 nM $I_{max}$: 69% | $IC_{50}$: 47 nM $I_{max}$: 55% | $IC_{50}$: 1 nM $I_{max}$: 80% |
| Mab2.10.3 | $IC_{50}$: ND $I_{max}$: 35% | $IC_{50}$: ND $I_{max}$: 29% | $IC_{50}$: ND $I_{max}$: 16% | $IC_{50}$: ND $I_{max}$: 28%(*) | $IC_{50}$: ND $I_{max}$: 30% |
| AT8 (MN1020) | Not tested | Not tested | $IC_{50}$: ND $I_{max}$: 19% | $IC_{50}$: ND $I_{max}$: 25% | $IC_{50}$: ND $I_{max}$: 36 |
| HJ8.5 | $IC_{50}$: ND $I_{max}$: 43% | Not tested | $IC_{50}$: ND $I_{max}$: 46% | $IC_{50}$: 73 nM $I_{max}$: 79% | $IC_{50}$: ND $I_{max}$: 67% |

ND: Not determined.
(*)maximal efficacy at 100 nM

Further experiments were performed in the cellular assay to determine the activity of AB1 having a murinised VL of SEQ ID NO: 9 and a murinised VH of SEQ ID NO.: 10 (VL9VH10) using Tau seed from P301L (n=2), AD (n=3) and PSP (n=3), providing final $IC_{50}$ values of 15 nM, 27 nM and 70 nM, respectively; and $I_{max}$ values of 79%, 68% and 57%, respectively.

3.2 Histological Analysis

AB1 having a rabbit VL of SEQ ID NO: 7 and a rabbit VH of SEQ ID NO.:8, humanized AB1 having a VL of SEQ ID No.: 11 and VH of SEQ ID No.: 14 (VL11VH14) or a VL of SEQ ID No.: 11 and VH of SEQ ID No.: 15 (VL11VH15) and the antibodies IPN002, PT3 and Mab2.10.3 of the prior art were assayed and optimal concentration determined using cryosections of human hippocampus from a donor with Alzheimer's disease that had previously been shown to contain pathological Tau structures using AT8 immunostaining (such as described in Braak & Braak, 1995, Neurobiol Aging; 16(3):271-8, and Porzig et al., 2007 Biochem Biophys Res Commun; 358(2):644-9). AB1 and all prior art antibodies exhibited specific and concentration-dependent immunoreactivity, apart from 101.4 (negative control antibody). From these data a single, optimal concentration of antibody was selected and used to screen a panel of six human brain samples. Three samples originated from donors with Alzheimer's disease or from very elderly donors that exhibited high levels of Tau pathology (positive Tau pathology detected using AT8 immunostaining), and three from donors without Tau pathology (negative Tau pathology detected using AT8 immunostaining).

AB1, VL11VH14, VL11VH15, PT3 and Mab2.10.3 showed a similar pattern of immunostaining in the AT8 positive samples. Specific immunostaining of neurofibrillary tangles (intraneuronal NFT), cytoplasmic Tau, neuritic plaque-like structures and neuropil threads was observed within the hippocampus and temporal cortex of the positive Tau pathology samples. However much lower immunostaining was detected in the AT8 negative tissues. This result suggests that these antibodies preferentially recognize pathological Tau in comparison to non-pathological Tau.

IPN002 provided a similar signal in both positive and negative Tau pathology samples.

3.3 Western Blot

Western blots performed using a chemiluminescent read out: lysates prepared from AD, PSP humans was loaded onto 10% polyacrylamide gels (20 µg protein per lane). Proteins were separated by SDS-PAGE (sodium dodecyl sulfate Polyacrylamide gel electrophoresis) and electrotransferred on to PVDF (Polyvinylidene fluoride) membrane. Membranes were blocked in 4% BSA (bovine serum albumin (in TBST: 50 mM Tris, 150 mM NaCl, 0.05% Tween 20, pH adjusted with HCl to pH 7.6). Membranes were incubated overnight at 4° C. with primary antibody or non-immune IgG control antibody, rinsed in TBST, incubated with secondary antibody for 1 hour (mouse anti-biotin), rinsed in TBST, incubated with tertiary antibody for 1 hour (anti-mouse IgG-peroxidase), rinsed in TBST, and developed using ECL (enhanced chemiluminescence).

mAB1 having a murinised VL of SEQ ID No: 9 and a murinised VH of SEQ ID No.: 10 binds to pathological Tau from samples of human AD, but weakly to PSP. See FIG. 4.

Experiment 4—Humanization of Identified Antibodies

AB1 with VL of SEQ ID No.: 7 and VH of SEQ ID No.: 8 was humanised by grafting the CDRs from the rabbit antibody V-region onto human germline antibody V-region frameworks. In order to recover the activity of the antibody, a number of framework residues from the rabbit V-regions were also retained in the humanised sequence. These residues were selected using the protocol outlined by Adair et al. (1991) (Humanised antibodies. WO91/09967). Alignments of the rabbit antibody (donor) V-region sequences with the human germline (acceptor) V-region sequences are shown in FIGS. 5 and 6, together with the designed humanised sequences. The CDRs grafted from the donor to the acceptor sequence are as defined by Kabat (Kabat et al., 1987), with the exception of CDR-H1 where the combined Chothia/Kabat definition is used (see Adair et al., 1991 Humanised antibodies. WO91/09967).

Human V-region IGKV1-39 plus JK4 J-region (IMGT, see Worldwide Website: imgt.org/) was chosen as the acceptor for antibody AB1 light chain CDRs. The light chain framework residues in grafts gL4 and gL9 are all from the human germline gene. CDRL3 was mutated in graft gL9 to modify a potential deamidation site. Human V-region IGHV4-39 plus JH4 J-region (IMGT, see Worldwide Website: imgt.org/) was chosen as the acceptor for the heavy chain CDRs of antibody AB1. In common with many rabbit antibodies, the VH gene of antibody AB1 is shorter than the selected human acceptor. When aligned with the human acceptor sequence, framework 1 of the VH region of antibody AB1 lacks the N-terminal residue, which is retained in the humanised antibody (FIG. 6). Framework 3 of the AB1 rabbit VH region also lacks two residues (75 and 76) in the loop between beta sheet strands D and E: in grafts gH41 and gH49 the gap is filled with the corresponding residues (Lysine 75, K75; Asparagine 76, N76) from the selected human acceptor sequence (FIG. 6). The heavy chain framework residues in grafts gH41 and gH49 are all from the human germline gene, with the exception of one or more residues from the group comprising residues 71 and 78 (Kabat numbering), where the donor residues Lysine (K71) and Valine (V78) were retained, respectively. Retention of residues K71 and V78 was essential for full potency of the humanised antibody. The Glutamine residue at position 1 of the human framework was replaced with Glutamic acid (E1) to afford the expression and purification of a homogeneous product: the conversion of Glutamine to pyroGlutamate at the N-terminus of antibodies and antibody fragments is widely reported. CDRH3 was mutated in grafts gH41 and gH49, to modify a potential deamidation site.

Genes encoding a number of variant heavy and light chain V-region sequences for each antibody were designed and constructed by an automated synthesis approach by DNA2.0 Inc. Further variants of heavy and light chain V-regions were created by modifying the VH and VK genes by oligonucleotide-directed mutagenesis, including, in some cases, mutations within CDRs to modify potential deamidation sites. For transient expression, the humanised light chain V-region genes were cloned into the UCB human light chain expression vector pMhCK, which contains DNA encoding the human Kappa chain constant region (Km3 allotype). The humanised heavy chain V-region genes were cloned into the UCB human gamma-4 heavy chain expression vector pMhγ4P FL, which contains DNA encoding the human gamma-4 heavy chain constant region with the hinge stabilising mutation S241P (Angal et al., Mol Immunol. 1993, 30(1):105-8). Alternatively, the humanised VH genes were cloned into the UCB gamma-1 heavy chain expression vector pMhγ1FL, which contains DNA encoding the human gamma-1 constant region (G1m17, 1 allotype). In order to assess the monovalent binding kinetics of the humanised antibodies, the humanised VH genes were also cloned into the UCB human Fab-HIS expression vector pMhFab10HIS, which contains DNA encoding the human gamma-1 CH1-hinge domain with a C-terminal tag of ten Histidine residues: the histidine tag facilitates purification of the expressed Fabs by affinity chromatography. Co-transfection of the resulting heavy and light chain vectors into HEK293 suspension cells was achieved using 293 Fectin (12347-019 Invitrogen), and gave expression of the humanised, recombinant antibodies in either the human IgG4P, IgG1 or Fab-HIS formats.

The variant humanised antibody chains, and combinations thereof, were expressed and assessed for their potency relative to the parent antibody, their biophysical properties and suitability for downstream processing.

For stable expression of the humanized recombinant antibodies in mammalian cells, the humanized light chain V-region gene was joined to a DNA sequence encoding the human C-Kappa constant region (Km3 allotype), to create a contiguous light chain gene. The humanized heavy chain genes were joined to DNA encoding either the human gamma-4P heavy chain constant region, or the human gamma-1 heavy chain constant region (G1m17, 1 allotype), to create contiguous heavy chain genes. Heavy and light chain genes were cloned into a mammalian expression vector.

The invention claimed is:

1. An isolated monoclonal Tau-binding antibody or binding fragment thereof, wherein said Tau-binding antibody or binding fragment thereof comprises:
   a light chain variable region comprising SEQ ID NO: 1 (CDR1), SEQ ID NO: 2 (CDR2) and SEQ ID NO: 3 (CDR3); and
   a heavy chain variable region comprising SEQ ID NO: 4 (CDR1), SEQ ID NO: 5 (CDR2) and SEQ ID NO: 6 (CDR3).

2. The isolated monoclonal Tau-binding antibody or binding fragment thereof of claim 1, wherein said Tan-binding antibody or binding fragment thereof comprises:
   a light chain variable region comprising SEQ ID NO: 13, and
   a heavy chain variable region comprising SEQ ID NO: 16.

3. The isolated monoclonal Tau-binding antibody or binding fragment thereof of claim 1, wherein the light chain variable region comprises SEQ ID NO: 11 or 12.

4. The isolated monoclonal Tau-binding antibody or binding fragment thereof of claim 1, wherein the heavy chain variable region comprises SEQ ID NO: 14 or 15.

5. The isolated monoclonal Tau-binding antibody or binding fragment thereof of claim 1, wherein said Tau-binding antibody or binding fragment thereof comprises:
   a light chain comprising SEQ ID NO: 11 or 12- or sequences at least-80% identical thereto, and
   a heavy chain comprising SEQ ID NO: 14 or 15.

6. The isolated monoclonal Tau-binding antibody or binding fragment thereof of claim 1, wherein said Tau-binding antibody or binding fragment thereof is a monoclonal humanized antibody.

7. An isolated nucleic acid molecule encoding the light and/or heavy chain of a Tau-binding antibody or binding fragment thereof of claim 1.

8. A cloning or expression vector comprising one or more nucleic acid molecule according to of claim 7.

9. A host cell comprising one or more nucleic acid molecule according to claim 7 or a cloning or expression vector comprising one or more of said nucleic acid molecules.

10. A method of producing a Tau-binding antibody or binding fragment thereof comprising at least the steps of:
    a) culturing a host cell of claim 9, and
    b) isolating said Tau-binding antibody or binding fragment thereof.

11. A method of treating a tauopathy comprising administering Tau-binding antibody or binding fragment thereof of claim 1 to a subject having a tauopathy.

12. The method of claim 11, wherein said tauopathy is Alzheimer's disease or progressive supranuclear palsy.

13. A method of diagnosing a tauopathy comprising contacting a biological sample with a monoclonal Tau-binding antibody or binding fragment thereof of claim 1 and detecting the binding of said antibody to said Tau protein.

14. The method of claim 13, wherein said tauopathy is Alzheimer's disease or progressive supranuclear palsy.

15. The isolated nucleic acid molecule of claim 7, said nucleic acid molecule encoding a light chain variable region comprising SEQ ID NO: 11.

16. The isolated nucleic acid molecule of claim 7, said nucleic acid molecule encoding a light chain variable region comprising SEQ ID NO: 12.

17. The isolated nucleic acid molecule of claim 7, said nucleic acid molecule encoding a heavy chain variable region comprising SEQ ID NO: 14.

18. The isolated nucleic acid molecule of claim 7, said nucleic acid molecule encoding comprising SEQ ID NO: 15.

19. The isolated nucleic acid molecule of claim 7, said nucleic acid molecule encoding a light chain comprising SEQ ID NO: 11 and a heavy chain comprising SEQ ID NO: 14.

20. The isolated nucleic acid molecule of claim 7, said nucleic acid molecule encoding a light chain comprising SEQ ID NO: 11 and a heavy chain comprising SEQ ID NO: 15.

21. The isolated nucleic acid molecule of claim 7, said nucleic acid molecule encoding a light chain comprising SEQ ID NO: 12 and a heavy chain comprising SEQ ID NO: 14.

22. The isolated nucleic acid molecule of claim 7, said nucleic acid molecule encoding a light chain comprising SEQ ID NO: 12 and a heavy chain comprising SEQ ID NO: 15.

23. The isolated monoclonal Tau-binding antibody or binding fragment thereof of claim 1, wherein the light chain variable region comprises SEQ ID NO: 11.

24. The isolated monoclonal Tau-binding antibody or binding fragment thereof of claim 1, wherein the light chain variable region comprises SEQ ID NO: 12.

25. The isolated monoclonal Tau-binding antibody or binding fragment thereof of claim 1, wherein the heavy chain variable region comprises SEQ ID NO: 14.

26. The isolated monoclonal Tau-binding antibody or binding fragment thereof of claim 1, wherein the heavy chain variable region comprises SEQ ID NO: 15.

27. The isolated monoclonal Tau-binding antibody or binding fragment thereof of claim 1, wherein said Tau-binding antibody or binding fragment thereof comprises:
   a light chain comprising SEQ ID NO: 11 and
   a heavy chain comprising SEQ ID NO: 14.

28. The isolated monoclonal Tau-binding antibody or binding fragment thereof of claim 1, wherein said Tau-binding antibody or binding fragment thereof comprises:
   a light chain comprising SEQ ID NO: 11 and
   a heavy chain comprising SEQ ID NO: 15.

29. The isolated monoclonal Tau-binding antibody or binding fragment thereof of claim 1, wherein said Tau-binding antibody or binding fragment thereof comprises:
   a light chain comprising SEQ ID NO: 12 and
   a heavy chain comprising SEQ ID NO: 14.

30. The isolated monoclonal Tau-binding antibody or binding fragment thereof of claim 1, wherein said Tau-binding antibody or binding fragment thereof comprises:
   a light chain comprising SEQ ID NO: 12 and
   a heavy chain comprising SEQ ID NO: 15.

31. The cloning or expression vector of claim 8, said cloning or expression vector comprising a nucleic acid molecule encoding a light chain variable region comprising SEQ ID NO: 11.

32. The cloning or expression vector of claim 8, said cloning or expression vector comprising a nucleic acid molecule encoding a light chain variable region comprising SEQ ID NO: 12.

33. The cloning or expression vector of claim 8, said cloning or expression vector comprising a encoding a heavy chain variable region comprising SEQ ID NO: 14.

34. The cloning or expression vector of claim 8, said cloning or expression vector comprising a nucleic acid molecule encoding a heavy chain variable region comprising SEQ ID NO: 15.

35. The cloning or expression vector of claim 8, said cloning or expression vector comprising a nucleic acid molecule encoding a light chain comprising SEQ ID NO: 11 and a heavy chain comprising SEQ ID NO: 14.

36. The cloning or expression vector of claim 8, said cloning or expression vector comprising a nucleic acid molecule encoding a light chain comprising SEQ ID NO: 11 and a heavy chain comprising SEQ ID NO: 15.

37. The cloning or expression vector of claim 8, said cloning or expression vector comprising a nucleic acid molecule encoding a light chain comprising SEQ ID NO: 12 and a heavy chain comprising SEQ ID NO: 14.

38. The cloning or expression vector of claim 8, said cloning or expression vector comprising a nucleic acid molecule encoding a light chain comprising SEQ ID NO: 12 and a heavy chain comprising SEQ ID NO: 15.

* * * * *

UNITED STATES PATENT AND TRADEMARK OFFICE
CERTIFICATE OF CORRECTION

PATENT NO. : 10,344,081 B2  Page 1 of 2
APPLICATION NO. : 15/742070
DATED : July 9, 2019
INVENTOR(S) : Kerry Louise Tyson et al.

It is certified that error appears in the above-identified patent and that said Letters Patent is hereby corrected as shown below:

In the Specification

Column 11,
Line 50, "http://vbase.rare.ce.cam.ac.uk/," should read --http://vbase.mrc.ce.cam.ac.uk/,--.

Column 15,
Line 24, "5202" should read --S202--.

Column 16,
Line 18, "5202" should read --S202--.

Column 38,
Line 48, "Fmoc-Thr(PO(OBzI)OH)-OH," should read --Fmoc-Thr(PO(OBzl)OH)-OH,--.

Column 42,
Line 15, "10004" should read --100μM--.

Column 44,
Line 64, "(51)." should read --(S1).--.

In the Claims

Column 111,
Line 44, "Tan-binding" should read --Tau-binding--.
Lines 58-59, "12- or sequences at least-80% identical thereto, and" should read --12 and--.

Column 112,
Line 33, "to of claim" should read --to claim--.
Line 63, "encoding comprising" should read --encoding a heavy chain variable region comprising--.

Signed and Sealed this
Fifth Day of May, 2020

Andrei Iancu
*Director of the United States Patent and Trademark Office*

Column 114,
Line 15, "comprising a encoding" should read --comprising a nucleic acid molecule encoding--.